(12) United States Patent
Li et al.

(10) Patent No.: US 11,761,044 B2
(45) Date of Patent: Sep. 19, 2023

(54) METHOD FOR EVALUATING WHETHER AN INDIVIDUAL WITH CANCER IS SUITABLE FOR TREATMENT WITH A CDK INHIBITOR

(71) Applicant: Chang Gung University, Taoyuan (TW)

(72) Inventors: Hsin-Pai Li, Taoyuan (TW); Cheng-Lung Hsu, Taoyuan (TW)

(73) Assignees: CHANELUN IVERSITY, Taoyuan (TW); CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 1105 days.

(21) Appl. No.: 16/451,942

(22) Filed: Jun. 25, 2019

(65) Prior Publication Data

US 2020/0010902 A1 Jan. 9, 2020

(30) Foreign Application Priority Data

Jul. 4, 2018 (TW) .................. 107123190

(51) Int. Cl.
| | |
|---|---|
| *C12Q 1/68* | (2018.01) |
| *C12Q 1/6886* | (2018.01) |
| *G16H 50/30* | (2018.01) |
| *G16B 20/10* | (2019.01) |
| *G16B 40/10* | (2019.01) |

(52) U.S. Cl.
CPC .......... *C12Q 1/6886* (2013.01); *G16B 20/10* (2019.02); *G16B 40/10* (2019.02); *G16H 50/30* (2018.01); *C12Q 2600/106* (2013.01); *C12Q 2600/156* (2013.01)

(58) Field of Classification Search
None
See application file for complete search history.

(56) References Cited

U.S. PATENT DOCUMENTS

2017/0067116 A1  3/2017  Slamon et al.

FOREIGN PATENT DOCUMENTS

WO  WO-2015/134674 A1  9/2015

OTHER PUBLICATIONS

Zhang et al; Molecular Cancer Research, 15(12); Dec. 2017; pp. 1722-1732.*
Kong et al; Clincal Cancer Research, 23(22); Nov. 2017; pp. 6946-6957.*
Whale et al; Nucleic Acids Research; vol. 40, e82, pp. 1-9; 2012.*
Ma et al., "Abstract 3773: Preclinical evaluation of the CDK4/6 inhibitor LEE011 in nasopharyngeal carcinoma (NPC) cell lines," Cancer Res (2016) No. 76, 4 pages.
Cao, Ya, "EBV based cancer prevention and therapy in nasopharyngeal carcinoma," Precision Oncology, (2017), 5 pages.
Zhang et al., "Identification of aberrant cell cycle regulation in Epstein-Barr virus-associated nasopharyngeal carcinoma by cDNA microarray and gene set enrichment analysis," Acta Biochim Biophys Sin (2009), vol. 41, Issue 5, 15 pages.
Hsu et al., "Integrated genomic analyses in PDX model reveal a cyclin-dependent kinase inhibitor Palbociclib as a novel candidate drug for nasopharyngeal carcinoma," Journal of Experimental & Clinical Research (2018) 37:233, 15 pages.

* cited by examiner

*Primary Examiner* — Jehanne S Sitton
(74) *Attorney, Agent, or Firm* — MUNCY, GEISSLER, OLDS & LOWE, P.C.

(57) ABSTRACT

The disclosure provides a method for evaluating whether an individual with cancer is suitable for being administered with anti-cancer drugs. Wherein the anti-cancer drug is a CDK inhibitor. The method includes the following steps: (1) detecting a copy number of a first gene and a copy number of a second gene from an in vitro sample of the individual with the cancer to obtain a copy number variation (CNV) of the first gene and a copy number variation (CNV) of the second gene; (2) calculating a copy number variation ratio (CNV ratio) between the copy number variation (CNV) of the first gene and the copy number variation (CNV) of the second gene, wherein the first gene encodes a cyclin and the second gene encodes a cyclin dependent kinase inhibitor (CDKN); and (3) determining whether the individual with the cancer is suitable for being administered with the CDK inhibitor according to the CNV ratio.

5 Claims, 41 Drawing Sheets
(4 of 41 Drawing Sheet(s) Filed in Color)
Specification includes a Sequence Listing.

FIG. 3A

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: CCND1-Forward primer

<400> SEQUENCE: 1
tctaagcaca gacagcacca                                           20

<210> SEQ ID NO 2
<211> LENGTH: 20
<212> TYPE: DNA
<213> ORGANISM: Artificial Sequence
<220> FEATURE:
<223> OTHER INFORMATION: CCND1-Reverse primer

<400> SEQUENCE: 2
atcagaaccg cacacagaaa                                           20

<210> SEQ ID NO 3
<211> LENGTH: 23
<212> TYPE: DNA
<213> ORGANISM: Artificial Sequence
<220> FEATURE:
<223> OTHER INFORMATION: CDKN2A-Forward primer

<400> SEQUENCE: 3
aggaacttag gaaataatga gcc                                       23

<210> SEQ ID NO 4
<211> LENGTH: 20
<212> TYPE: DNA
<213> ORGANISM: Artificial Sequence
<220> FEATURE:
<223> OTHER INFORMATION: CDKN2A-Reverse primer

<400> SEQUENCE: 4
caggagtagg gagaggagaa                                           20

<210> SEQ ID NO 5
<211> LENGTH: 21
<212> TYPE: DNA
<213> ORGANISM: Artificial Sequence
<220> FEATURE:
<223> OTHER INFORMATION: RAD52 - Forward primer

<400> SEQUENCE: 5
tactacctca atgatgggac c                                         21

<210> SEQ ID NO 6
<211> LENGTH: 24
<212> TYPE: DNA
<213> ORGANISM: Artificial Sequence
<220> FEATURE:
<223> OTHER INFORMATION: RAD52 - Reverse primer

<400> SEQUENCE: 6
aggactaatc tccaaataaa ctac                                      24
```

METHOD FOR EVALUATING WHETHER AN INDIVIDUAL WITH CANCER IS SUITABLE FOR TREATMENT WITH A CDK INHIBITOR

BACKGROUND OF THE INVENTION

Field of Invention

This Non-provisional application claims priority under 35 U.S.C. § 119(a) on Patent Application No(s). 107123190 filed in Taiwan, Republic of China on Jul. 4, 2018, the entire contents of which are hereby incorporated by reference.

This disclosure relates to a technical field of a biomarker which is related to a copy number variation in plasma, and more particularly to a use of the biomarker of the copy number variation in plasma for a medical-drug guide of nasopharynx cancer and other cancers.

Related Art

It is known that the chromosomes of normal human somatic cells are diploid. The copy number of other allelic genes should be two except for the genes on the sex chromosomes. However, the copy number of some genes in cancer cells may be amplified (copy number is greater than 2) or deleted (deletion) (copy number is less than 2).

The important features of cancer cells are that they are constantly growing and unregulated. One of the reasons is that the gene copy number variation (CNV) that regulates the cell cycle. The genes of cancer cells often have CNV mutations such as the amplification of the cyclin D1 (CCND1) gene which promoting cell growth and the deletion of the cyclin dependent kinase inhibitor 2A/p16 (CDKN2A/p16) gene which inhibiting cell growth. It is known that cell-free DNA (cfDNA) of cancer cells can be detected in the peripheral blood of cancer patients. The cell-free DNA of cancer cells often carries mutations of specific DNA, and thus can be used as a marker for identifying cancers.

In addition, CDK inhibitors are currently approved as target drugs which are mainly used for treating metastatic breast cancer. These drugs are used in metastatic breast cancer patients to inhibit the growth of cancer cells. However, these drugs do not have the effect of inhibiting the growth of cancer cells in every cancer patient.

Accordingly, it is an urgent need to provide a method for the evaluation of accurate personal medication recommendations of CDK inhibitor drugs which can accurate and rapid screening the patients who are suitable for being administered with such cancer target drugs. Therefore, how to screen patients who are suitable for being administered with this drug through an in vitro sample of a cancer patient before the administration of the CDK inhibitor to avoid the limitation of treatment effect, time or money of the patient has become one of the important objectives.

SUMMARY OF THE INVENTION

In view of the foregoing objectives, the purpose of the invention is to develop a method for evaluating whether a patient with a cancer is suitable for being administered with target drug, a method for treating a patient and a use of a biomarker in an in vitro sample of an individual with cancer for manufacturing a diagnosis combination. The method of the invention is used for detecting an in vitro sample of a patient with cancer and thus detecting a copy number variation (CNV) of the CCND1 gene and a copy number variation (CNV) of the CDKN2A gene, respectively. And calculating a copy number variation ratio (CNV ratio) between the copy number variation (CNV) of the CCND1 gene and the copy number variation (CNV) of the CDKN2A gene. The CNV ratio is used for evaluating whether the regulation of cell cycle in the cancer cell is normal which is used for evaluating whether a target drug of cancer which is approved (such as cell cycle inhibitors) is suitable for being administered for this patient.

To achieve the above objective, the invention provides a method for evaluating whether an individual with a cancer is suitable for being administered with an anti-cancer drug, wherein the anti-cancer drug is a CDK inhibitor, the method includes steps of: detecting a copy number of a first gene and a copy number of a second gene from an in vitro sample of the individual with the cancer to obtain a copy number variation (CNV) of the first gene and a copy number variation (CNV) of the second gene; calculating a copy number variation ratio (CNV ratio) between the copy number variation (CNV) of the first gene and the copy number variation (CNV) of the second gene, wherein the first gene encodes a cyclin and the second gene encodes a cyclin dependent kinase inhibitor (CDKN); and determining whether the individual with the cancer is suitable for being administered with the CDK inhibitor according to the CNV ratio.

In addition, the invention also provides a method for treating an individual with a cancer, the method includes steps of: a step of evaluating whether the individual with the cancer is suitable for being administered with an anti-cancer drug, wherein the step of evaluating comprises: detecting a copy number of a first gene and a copy number of a second gene from an in vitro sample of the individual with the cancer to obtain a copy number variation (CNV) of the first gene and a copy number variation (CNV) of the second gene; calculating a copy number variation ratio (CNV ratio) between the copy number variation (CNV) of the first gene and the copy number variation (CNV) of the second gene, wherein the first gene encodes a cyclin and the second gene encodes a cyclin dependent kinase inhibitor (CDKN); and determining whether the individual with the cancer is suitable for being administered with the CDK inhibitor according to the CNV ratio; and a step of administering an effective amount of the CDK inhibitor when the individual with the cancer is determined to be suitable for being administered with the CDK inhibitor.

In addition, the invention also provides a use of a biomarker in an in vitro sample of an individual with a cancer for manufacturing a diagnosis combination, wherein the diagnosis combination is used for evaluating a possibility, and determining whether the individual with the cancer is suitable for being administered with an anti-cancer drug according to the possibility, the anti-cancer drug is a CDK inhibitor, wherein the biomarker includes a first gene and a second gene, the first gene encodes a cyclin and the second gene encodes a cyclin dependent kinase inhibitor (CDKN), a copy number of the first gene and a copy number of the second gene are detected to obtain a copy number variation (CNV) of the first gene and a copy number variation (CNV) of the second gene, a copy number variation ratio (CNV ratio) between the copy number variation (CNV) of the first gene and the copy number variation (CNV) of the second gene is calculated, and whether the individual with the cancer is suitable for being administered with CDK inhibitor is determined according to the CNV ratio.

In one embodiment, the cancer is breast cancer, esophageal squamous-cell carcinoma (ESCC), hepatic carcinoma (HCC), pulmonary adenocarcinoma, melanoma, colon cancer, prostate cancer, ovary cancer, kidney cancer or leukemia.

In one embodiment, the cyclin is a G1 phase cyclin.

In one embodiment, the cyclin is Cyclin D.

In one embodiment, the first gene is CCND1.

In one embodiment, the cyclin dependent kinase inhibitor is a G1 phase cyclin dependent kinase inhibitor or an S phase cyclin dependent kinase inhibitor.

In one embodiment, the second gene is CDKN2A or CDKN2B.

In one embodiment, the first gene is CCND1 and the second gene is CDKN2A.

In one embodiment, the anti-cancer drug is a CDK 4/6 inhibitor.

In one embodiment, the anti-cancer drug is palbociclib, ribociclib or abemaciclib.

In one embodiment, the individual with the cancer is determined to be suitable for being administered with the anti-cancer drug when the CNV ratio is above 4.

In one embodiment, the copy number of the first gene and the copy number of the second gene are detected by quantitative PCR (Q-PCR) in vitro.

In one embodiment, the in vitro sample is a cancer tissue sample or a blood sample.

In one embodiment, the in vitro sample is a cell-free DNA (cfDNA) in the blood sample.

In one embodiment, the cancer is nasopharynx cancer (NPC) and the method further includes a step of detecting an amount of Epstein-Barr virus (EB virus) from the in vitro sample of the individual with the cancer, and determining whether the individual with the cancer is suitable for being administered with the anti-cancer drug according to the CNV ratio and the amount of EB virus.

In one embodiment, the first gene is CCND1.

In one embodiment, the second gene is CDKN2A or CDKN2B.

In one embodiment, the first gene is CCND1 and the second gene is CDKN2A.

In one embodiment, the anti-cancer drug is a CDK 4/6 inhibitor.

In one embodiment, the anti-cancer drug is palbociclib, ribociclib or abemaciclib.

In one embodiment, the individual with the cancer is determined to be suitable for being administered with the anti-cancer drug when the CNV ratio is above 4 and the amount of EB virus is above 5000 copies/ml.

In one embodiment, the in vitro sample is a cancer tissue sample or a blood sample.

In one embodiment, the in vitro sample is a cell-free DNA (cfDNA) in the blood sample.

As mentioned above, the efficacy of this invention is to provide a method for evaluating whether a patient with cancer is suitable for being administered with target drugs, a method for treating a patient and a use of a biomarker in an in vitro sample of an individual with cancer for manufacturing a diagnosis combination. This invention extracts an in vitro sample of a patient, and then analysis the CNV ratio of the CCND1 gene and the CDKN2A gene of the in vitro sample by a simple and rapid genetic analysis method. And the CNV ratio is used for accurate personal medication recommendations of cancer target drugs. Due to the cancer target drugs are very expensive, the doctors can select a suitable patient (such as high CNV ratio) by the method of this invention, and the CNV ratio could be a support for medication recommendation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will become more fully understood from the detailed description and accompanying drawings, which are given for illustration only, and thus are not limitative of the present invention, and wherein:

FIG. 2A shows somatic mutations (including non-synonymous missense and splice site mutations) of the five NPC-PDX tumors which identified from sequencing data. Each bar represents the number of base substitutions. FIG. 2B shows the percentage of each base substitution for the 282 SNVs.

FIGS. 3A-3D show genetic alterations in NPC-PDX tumors. FIG. 3A: Copy number variations (CNV) of NPC-PDX tumors versus corresponding patient's peripheral blood mononuclear cells (PBMC). Genome-wide CNV alterations in four paired PDX tumor samples (ST, LN, LG and LV). CCND1 CNV gain (the arrow points to the lower left) and CDKN2A CNV loss (the arrow points to the upper left) are indicated. FIG. 3B: HE and EB virus-encoded small RNA (EBER) staining of parental NPC tumor with bone metastasis and its derived NPC-PDX. FIG. 3C shows CNV profile comparisons of NPC FFPE-Bone and PDX-Bone based on WES. FIG. 3D shows CNV profile comparisons of NPC FFPE-Bone and PDX-Bone based on ultra-deep sequencing of cancer panel-409 (genes associated with or without copy number alteration are indicated in different colors or in grey, respectively). Observed copy number for each evaluated position is shown on the y-axis as a log 2 scale. Correlation plots with Pearson's correlation coefficient, r, indicating similarities between two CNV profiles.

FIG. 4C shows correlation plots with Pearson's correlation coefficient r.

FIG. 5A: The expression fold change of candidate genes (CCND1, CDKN2A and CDKN2B) are indicated based on the cDNA microarray data of five PDX tissues, and C666-1 (EBV-positive NPC cells) and NP69 (immortalized normal nasopharyngeal cells, as control) cell lines. FIG. 5B: Agarose gel electrophoresis of RT-PCR products of CCND1 in PBMC, two NPC cell lines and five PDXs (GAPDH serves as an internal control). Cyclin D1 IHC staining in NPC no. 13 patient, with NPC primary site, NPC metastatic to bone, and PDX-Bone tumor is shown in FIG. 5C. Cyclin D1 IHC staining in NPC no. 2 patient, with NPC metastatic to lymph node, and PDX-LN tumor is shown in FIG. 5D.

FIG. 6A shows drug sensitivity tests in C666.1 cells. FIGS. 6B-6D show drug sensitivity tests in PDX-C666.1 xenograft. FIG. 6B shows tumor volume of drug sensitivity tests in PDX-C666.1 xenograft. FIG. 6C shows tumor weight (g) of drug sensitivity tests in PDX-C666.1 xenograft. FIG. 6D shows mice body weight of drug sensitivity tests in PDX-C666.1 xenograft. Abbreviation, GSK, GSK126; DEC, decitabine; GEM, gemcitabine; PAL, palbociclib. FIG. 6E shows flow cytometry analysis of C666.1 cells in the presence of PAL (0, 0.1, 0.5 and 1 μM).

FIGS. 7A-7F: PDX-Bone (NPC13-F4 corresponds to patient no. 13 derived bone metastatic NPC tumor was transplanted in NOD/SCID mice at 4th passage. (FIGS. 7A-7B) Mice gross tumor, (FIG. 7C) tumor volume, (FIG. 7D) tumor weight, (FIG. 7E) mice body weight change, and (FIG. 7F) cyclin D1 IHC and EBER staining in control (DMSO) and GEM and PAL treatment. FIGS. 7G-7H: PDX-LN (NPC02-F11 corresponds to patient no. 2 derived lymph node metastatic NPC tumor was transplanted in NOD/SCID mice at 11th passage), (FIG. 7G) tumor volume, (FIG. 7H) tumor weight. Abbreviation: GSK, GSK126; DEC, decitabine; GEM, gemcitabine; PAL, palbociclib.

(FIG. 8B) tumor weight; and (FIG. 8C) mice body weight change in the presence of DMSO (control), DEC (reduced dose) and PAL. Abbreviation: DEC, decitabine; PAL, palbociclib.

FIG. 9A: RNA expression of nine cell cycle-related genes in NPC PDX-B exposed to five drug treatments based on original normalized (RPKM) RNA seq data (upper), fold change normalization with DMSO control (middle), RT-PCR validation fold change normalized with internal control GAPDH in DMSO (lower). FIG. 9B: Western blot of the nine cell cycle-related proteins after DMSO (control), GEM, PAL and GEM+PAL treatment in NPC PDX-B tissues. FIG. 9C: Western blot of the nine cell cycle-related proteins in C666-1 cells treated with different concentrations of GEM (0.1, 1, and 10 μM) and PAL (0.1, 1, and 5 μM) after 48 h.

FIG. 10A: The CNV of CCND1, CDKN2A and RAD52 in 24 NPC plasma with low EBV DNA load (<5,000 copies/ml) based on the Q-PCR results. FIG. 10B: Correlation plot between the CNV of CCND1, CDKN2A and RAD52 versus log EBV DNA load (low copy) in 24 NPC plasma. Pearson's correlation coefficient, r, and exponential regression trend lines are indicated. FIG. 10C: Overall survival in 81 metastatic NPC patients with EBV copy cut off (5000 copies/ml and 10000 copies/ml) in plasma (2002-2016). Clinical characteristics of metastatic NPC patients with FFPE tissue cyclin D1 immnunohistochemical staining (2002-2016) was summarized in Table 5 (which is listed as followed).

FIG. 11A: CNV of CCND1, CDKN2A and RAD52 in 22 NPC plasma with high EBV DNA load (>5,000 copies/ml) based on Q-PCR results. FIG. 11B: Correlation plot between CNV of CCND1, CDKN2A and RAD52 and log EBV DNA load in 22 NPC plasma samples. FIG. 11C: Correlation between CNV of the CCND1/ CDKN2A ratio and log EBV load in 22 NPC plasma. Pearson's correlation coefficient, r, and equations of regression are indicated.

FIG. 12A: Cyclin D1 expression in a liver and a lung metastasized NPC patients. The Kaplan-Meier survival curves of the NPC patients classified by the (FIG. 12B) intensity and (FIG. 12C) percentage of positive cells in cyclin D1 IHC staining. A 46 year-old NPC patient with T4N2M0 (stage IVa), also a hepatitis B virus carrier, received concurrent chemoradiotherapy (CCRT) for local disease control. Liver metastasis (cyclin D1 staining, in FIG. 12A) was detected nine months later and five different lines of palliative chemotherapy prescribed. Finally, the patient received palbociclib (PAL) as salvage treatment at Johns Hopkins Medicine, Singapore. FIG. 12D: Plasma EBV DNA load reflecting the clinical treatment response of the patient was decreased after treatment with PAL. FIG. 12E: Whole-body tumor scan before and after PAL treatment at 2-month intervals revealed stable disease.

DETAILED DESCRIPTION OF THE INVENTION

Figure 1A:
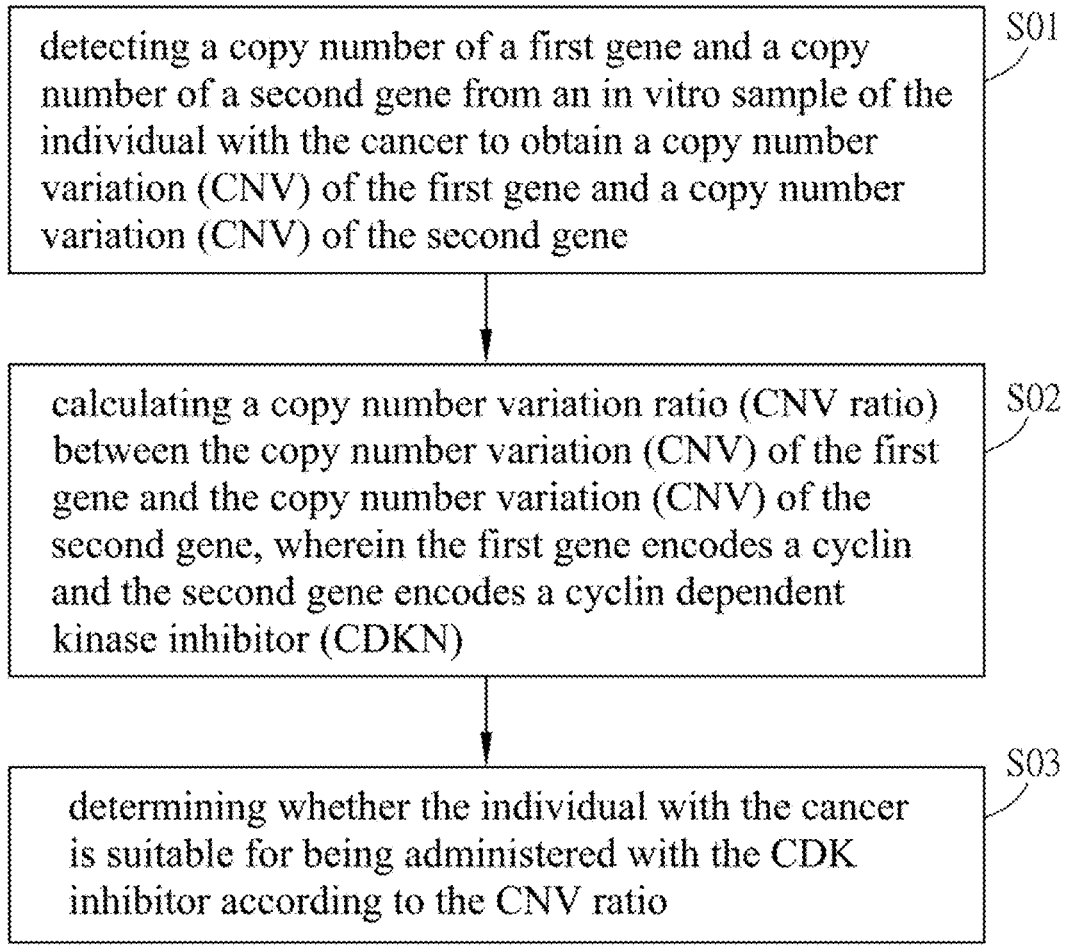
FIG. 1A is a flow chart showing the first embodiment of the method for evaluating whether an individual with a cancer is suitable for being administered with an anti-cancer drug of this invention.

The embodiments of the invention will be apparent from the following detailed description, which proceeds with reference to the accompanying drawings, wherein the same references relate to the same elements.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary. The recitation of ranges of values herein is merely intended to serve as a shorthand method of referring individually to each separate value falling within the range. Unless otherwise indicated herein, each individual value with a range is incorporated into the specification as if it were individually recited herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims. No language in the specification should be construed as indicating any non-claimed element essential to the practice of the invention.

The following discussion provides many example embodiments of the inventive subject matter such as a method for evaluating whether an individual with a cancer is suitable for being administered with a CDK inhibitor by detecting the copy number of genes from an in vitro sample of the individual with the cancer. It should be appreciated that although these embodiments list single or combination of cancer, the copy numbers of specific genes and CDK inhibitors, the inventive subject matter is considered to include all possible combinations of the disclosed elements such as a CDK inhibitor which has same or similar effect compared with the listed CDK inhibitor. In addition, the selection of the CDK inhibitor can be changed according to the age of the patient, the species of cancer, the stage of cancer and the overall health status.

The terms "individual with cancer" and "patient" refer to an individual who has cancer. The species of cancer include, but not limited to, breast cancer, esophageal squamous-cell carcinoma (ESCC), hepatic carcinoma (HCC), pulmonary adenocarcinoma, melanoma, colon cancer, prostate cancer, ovary cancer, kidney cancer or leukemia. The terms "individual" and "patient" can be used interchangeably and may refer to a human or non-human mammal or a bird. Non-human mammals include, for example, livestock and pets, such as ovine, porcine, canine, feline and murine mammals. In certain embodiments, the patient is human.

The terms "anti-cancer drug" and "cancer target drug" can be used interchangeably and may refer to a drug for treating an individual with cancer. The species of "anti-cancer drug" include, but not limited to, CDK inhibitor, palbociclib, ribociclib, abemaciclib, Gemcitabine, decitabine or GSK-12.

The term "in vitro sample" refers to a biomaterial (such as but not limited to cells, tissue, organs and so on) which is isolated from an organism. For example, "in vitro sample" can be the cell which is isolated from an organism, and then the cell is primarily cultured for later use. Or the primary cell can be cultured to be a cell line and being stored appropriately for later use.

The term "copy number" refers to a number of a gene in a genome. For example, it is known that the chromosomes of normal human somatic cells are diploid. Therefore, the copy number of allelic genes should be two. While, the copy number of genes on the sex chromosomes should be one.

The term "copy number variation (CNV)" refers to a variance of a gene in a genome which has a mutation. The mutations include, but not limited to, insertion, deletion and so on. For example, it is known that the chromosomes of normal human somatic cells are diploid. And, the copy number of allelic genes should be two. If the gene has a delete mutation, the copy number will be less than two. And the difference between the original copy number and the copy number after deletion is copy number variation.

The term "cell-free DNA (cfDNA)" refers to the DNA is free out of the cell and without cells. "cell-free DNA" is widely found in samples of animals, plants and humans. The samples include, but not limited to, serum, plasma, cerebrospinal fluid, urine, sputum or feces.

The term "encode" refers to DNA sequence could be transcribed to be RNA, and then be translated to be protein. Thus, "gene encodes a protein" refers to a gene which has a gene sequence that could be translated to a protein.

The method for evaluating whether an individual with a cancer is suitable for being administered with an anti-cancer drug of this invention could detecting a copy number of a first gene and a copy number of a second gene from an in vitro sample of the individual with the cancer to obtain a copy number variation (CNV) of the first gene and a copy number variation (CNV) of the second gene, and calculating a copy number variation ratio (CNV ratio) between the copy number variation (CNV) of the first gene and the copy number variation (CNV) of the second gene, and thus determining whether the individual with the cancer is suitable for being administered with the CDK inhibitor according to the CNV ratio. The method for evaluating whether an individual with a cancer is suitable for being administered with an anti-cancer drug of this invention will be described in detail according to the following embodiments.

Please refer to FIG. 1A, FIG. 1A is a flow chart showing the first embodiment of the method for evaluating whether an individual with a cancer is suitable for being administered with an anti-cancer drug of this invention. In this embodiment, the anti-cancer drug is a CDK inhibitor. The method includes the following steps. Step S01: detecting a copy number of a first gene and a copy number of a second gene from an in vitro sample of the individual with the cancer to obtain a copy number variation (CNV) of the first gene and a copy number variation (CNV) of the second gene. Step S02: calculating a copy number variation ratio (CNV ratio) between the copy number variation (CNV) of the first gene and the copy number variation (CNV) of the second gene, wherein the first gene encodes a cyclin and the second gene encodes a cyclin dependent kinase inhibitor (CDKN). And step S03: determining whether the individual with the cancer is suitable for being administered with the CDK inhibitor according to the CNV ratio. In this embodiment, the anti-cancer drug is a CDK 4/6 inhibitor which includes, but not limited to palbociclib, ribociclib or abemaciclib.

In this embodiment, step S01 is to detect a copy number of a first gene and a copy number of a second gene from an in vitro sample of the individual with the cancer to obtain a copy number variation (CNV) of the first gene and a copy number variation (CNV) of the second gene. For example, a copy number of a first gene and a copy number of a second gene are detected from an in vitro sample by Q-PCR. In particular, an in vitro sample could be detected by the methods include, but not limited to PCR, NGS or any other methods which is used to detect the copy number of genes and is known to those of ordinary skill in the art. The cancer of the individual with a cancer is breast cancer, esophageal squamous-cell carcinoma (ESCC), hepatic carcinoma (HCC), pulmonary adenocarcinoma, melanoma, colon cancer, prostate cancer, ovary cancer, kidney cancer or leukemia. In particular, the species of cancer are embodiments for illustration and does not pose a limitation of the invention. In this embodiment, the individual with a cancer is a human. In this embodiment, in vitro sample is a cancer tissue sample or a blood sample, such as but not limited to a cell-free DNA (cfDNA) in the blood sample. For example, cancer tissue sample includes, but not limited to lymph, saliva, biopsy or any cancer tissue sample known to those of ordinary skill in the art.

In this embodiment, step S02 is to calculate a copy number variation ratio (CNV ratio) between the copy number variation (CNV) of the first gene and the copy number variation (CNV) of the second gene, wherein the first gene encodes a cyclin and the second gene encodes a cyclin dependent kinase inhibitor (CDKN). For example, the cyclin is a G1 phase cyclin which includes but not limited to Cyclin D. The cyclin dependent kinase inhibitor is a G1 phase cyclin dependent kinase inhibitor or an S phase cyclin dependent kinase inhibitor. In this embodiment, the first gene is CCND1 and the second gene is CDKN2A or CDKN2B. In other embodiment, the first gene is CCND1 and the second gene is CDKN2A.

In this embodiment, step S03 is to determine whether the individual with the cancer is suitable for being administered with the CDK inhibitor according to the CNV ratio. For example, step S03 is determined according to the copy number variation ratio (CNV ratio) of step S02. The individual with the cancer is determined to be suitable for being administered with the anti-cancer drug when the CNV ratio is above 4. Herein, the evaluation of the copy number variation ratio (CNV ratio) could be different according the species of the anti-cancer drugs, the species or subspecies of the individual with the cancer. This embodiment herein is intended merely to better illuminate the invention and does not pose a limitation of the invention.

Figure 1B:
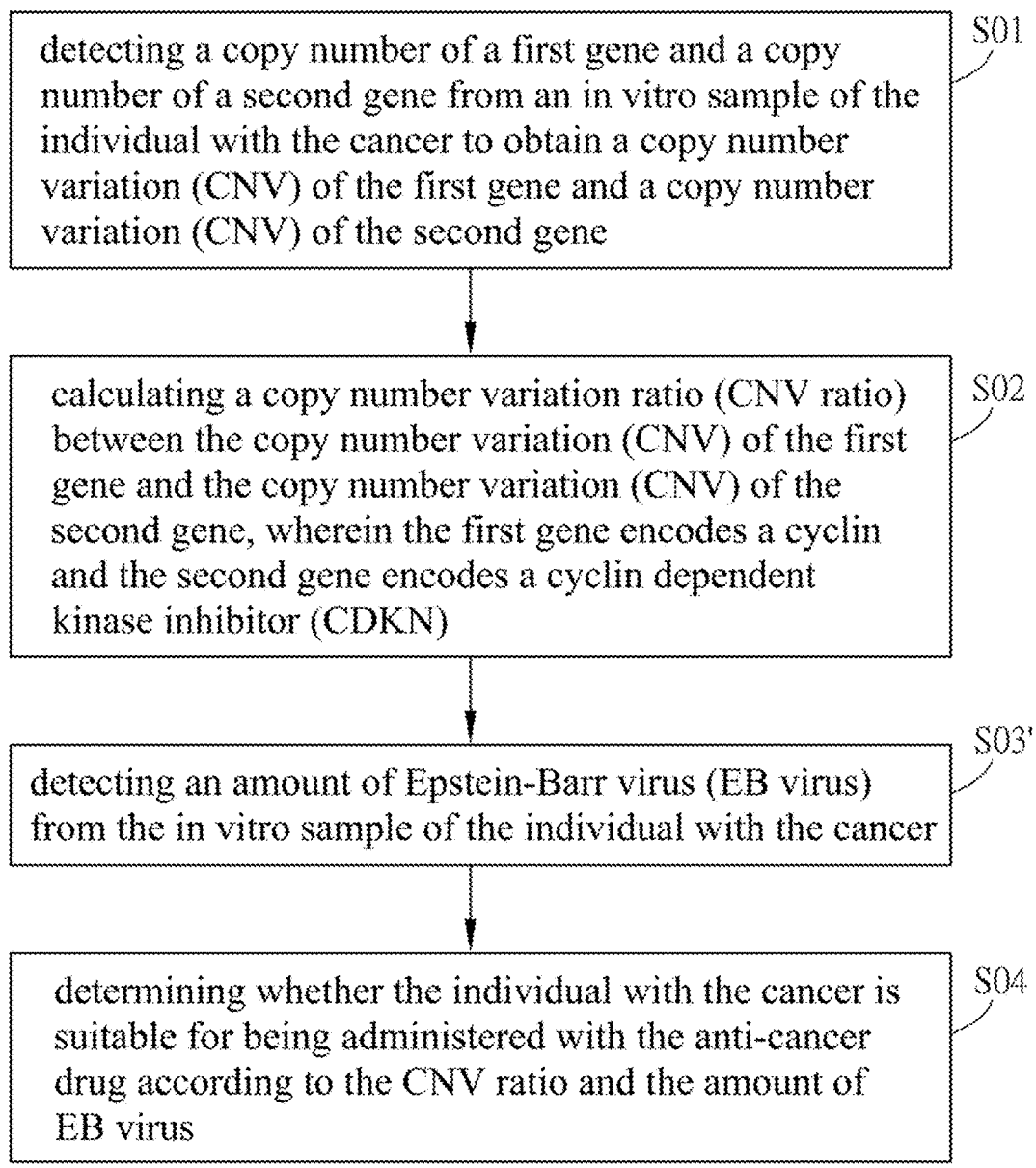
FIG. 1B is a flow chart showing the second embodiment of the method for evaluating whether an individual with a cancer is suitable for being administered with an anti-cancer drug of this invention.

Please refer to FIG. 1B, FIG. 1B is a flow chart showing the second embodiment of the method for evaluating whether an individual with a cancer is suitable for being administered with an anti-cancer drug of this invention. In this embodiment, the cancer is nasopharynx cancer (NPC) and the method includes step 01 and step 02. Step 01 and step 02 are substantially the same as those in the previous embodiment and are therefore omitted here. In this embodiment, the method further includes the following steps. Step S03': detecting an amount of Epstein-Barr virus (EB virus) from the in vitro sample of the individual with the cancer. Step S04: determining whether the individual with the cancer is suitable for being administered with the anti-cancer drug according to the CNV ratio and the amount of EB virus.

In this embodiment, step S03' is to detect an amount of Epstein-Barr virus (EB virus) from the in vitro sample of the individual with the cancer. For example, the individual with the cancer is a human. In this embodiment, in vitro sample is a cancer tissue sample or a blood sample, such as but not limited to a cell-free DNA (cfDNA) in the blood sample. For example, cancer tissue sample includes, but not limited to lymph, saliva, biopsy or any cancer tissue sample known to those of ordinary skill in the art. In this embodiment, an amount of Epstein-Barr virus (EB virus) from the in vitro sample is detected by Q-PCR. In particular, an in vitro sample could be detected by the methods include, but not limited to ELISA, western blot, PCR or any other methods which is used to detect the amount of virus and is known to those of ordinary skill in the art.

In this embodiment, step S04 is to determine whether the individual with the cancer is suitable for being administered with the anti-cancer drug. For example, step S04 is determined according to the CNV ratio and the amount of EB virus of step S03'. The individual with the cancer is determined to be suitable for being administered with the anti-cancer drug when the CNV ratio is above 4 and the amount of EB virus is above 5000 copies/ml. In detail, the difference between step S04 of the second embodiment and step S03 of the first embodiment is that whether the evaluation needs to be determined according to the amount of EB virus. Herein, the evaluation of the copy number variation ratio (CNV ratio) and the amount of EB virus could be different according the species of the anti-cancer drugs, the species or subspecies of the individual with the cancer. This embodiment herein is intended merely to better illuminate the invention and does not pose a limitation of the invention.

In addition, this invention also provide another embodiment which is a use of a biomarker in an in vitro sample of an individual with a cancer for manufacturing a diagnosis combination. The diagnosis combination is used for evaluating a possibility, and determining whether the individual with the cancer is suitable for being administered with an anti-cancer drug according to the possibility. The anti-cancer drug is a CDK inhibitor, wherein the biomarker includes a first gene and a second gene, the first gene encodes a cyclin and the second gene encodes a cyclin dependent kinase inhibitor (CDKN), a copy number of the first gene and a copy number of the second gene are detected to obtain a copy number variation (CNV) of the first gene and a copy number variation (CNV) of the second gene, a copy number variation ratio (CNV ratio) between the copy number variation (CNV) of the first gene and the copy number variation (CNV) of the second gene is calculated, and whether the individual with the cancer is suitable for being administered with CDK inhibitor is determined according to the CNV ratio.

The preferred examples of this embodiment, are substantially the same as those in the previous embodiments and are therefore omitted here.

In addition, this invention further provide another embodiment which is a method for treating an individual with a cancer. The method includes steps of: a step of evaluating whether the individual with the cancer is suitable for being administered with an anti-cancer drug, wherein the step of evaluating comprises: detecting a copy number of a first gene and a copy number of a second gene from an in vitro sample of the individual with the cancer to obtain a copy number variation (CNV) of the first gene and a copy number variation (CNV) of the second gene; calculating a copy number variation ratio (CNV ratio) between the copy number variation (CNV) of the first gene and the copy number variation (CNV) of the second gene, wherein the first gene encodes a cyclin and the second gene encodes a cyclin dependent kinase inhibitor (CDKN); and determining whether the individual with the cancer is suitable for being administered with the CDK inhibitor according to the CNV ratio; and a step of administering an effective amount of the CDK inhibitor when the individual with the cancer is determined to be suitable for being administered with the CDK inhibitor. The preferred examples of this embodiment, are substantially the same as those in the previous embodiments and are therefore omitted here.

To illustrate the biological characteristics and molecular mechanism according to the previous embodiments, there are several examples shown below.

The following examples indicate that plasma EBV DNA load is positively correlated with the CNV ratio of CCND1/CDKN2A. Hence, determination of the CNV ratio between cell-free CCND1 and CDKN2A as well as EBV DNA load in NPC plasma may provide valuable information that aids in the effective monitoring of NPC progression and recurrence. In addition, the cell-free CCND1/CDKN2A ratio may signify whether patients with NPC recurrence are suitable for cell cycle-dependent kinase inhibitor PAL treatment. From experience, when the EBV DNA load in patient plasma is greater than 5,000 copies/ml, the condition of the patient gradually deteriorates and thus more active medical measures should be employed. The cut-off value for the CNV CCND1/CDKN2A ratio was set to 4, which corresponds to EBV DNA load of ~5,000 copies/ml in plasma. These examples propose that this CNV ratio, in combination with EBV DNA load in plasma, may be effectively utilized as a guideline for individualizing treatments for NPC patients.

Materials and Methods

Drugs

Gemcitabine (GEM), GSK-126, and decitabine (DEC) were purchased from Sigma Chemical Co (St. Louis, Mo.). Palbociclib (PAL) was acquired from MedChem Express (Monmouth Junction, N.J.).

Cell Growth Assay and Animal Studies

NP69 (T antigen immortalized nasopharyngeal epithelial (NP) cells), C666-1 (NPC cell harboring EBV) and HK-1 (NPC cell without EBV) cells were maintained in RPMI containing 10% fetal bovine serum (FBS). Cell growth assay and animal studies were conducted as described in a previous report (Hsu C L, et al: Application of a patient-derived xenograft model in cytolytic viral activation therapy for nasopharyngeal carcinoma. Oncotarget 2015, 6(31):31323-31334.). All experiments involving laboratory animals followed the Guidelines for Animal Experiments of CGMH and were approved by the Animal Research CGMH.

Cell Cycle Analysis

Cells ($1\times10^6$) were seeded on a 10 cm dish in complete medium with 10% FBS for 24 h. The medium was replaced with basal medium devoid of FBS for a further 24 h. Next, cells were treated with complete medium containing 10% FBS plus 0-1 µM palbociclib for 24 h, trypsinized, and fixed in 70% ethanol at 4° C. for 30 min. Fixed cells were washed with PBS, treated with 100 µg/mL RNase and stained with 50 µg/mL Propidium Iodide. Following staining, cells were washed with PBS and analyzed using the Navios™ Flow Cytometer (Beckman Coulter). Data were evaluated using Kaluza Flow Cytometry Analysis Software.

Patient Participants

Seventeen biopsy-proven NPC patients with local recurrence or distant metastasis were enrolled between July 2013 and June 2016; one hundred thirty nine NPC patient biopsies/FFPE collected between 2002~2016 in Chang Gung Memorial Hospital (CGMH); and NPC patient had Palbociclib written informed consent, approved by the Institutional Review Board (IRB) of Chang Gung Memorial Hospital (CGMH).

Patient-Derived Xenograft (PDX)

PDX models were generated according to a previously reported procedure (Hsu C L, et al: Application of a patient-derived xenograft model in cytolytic viral activation therapy for nasopharyngeal carcinoma. Oncotarget 2015, 6(31): 31323-31334.). Briefly, NPC tumor samples were obtained from patients undergoing biopsy or surgical resection. Each sample was immediately cut into small sections, immersed in antibiotic-containing PBS and implanted subcutaneously in the flank regions of anesthetized NOD/SCID mice. After reaching a diameter of ~1 cm, the xenograft was excised and sub-implanted into subsequent passage mice. It took 2~4 months to passage PDX tumor in mice.

Drug Sensitivity Tests in the PDX Model

After tumors had been sub-implanted in NOD/SCID mice and xenografts had reached a volume of 50~150 $mm^3$, animals were randomized (3-5 mice with tumors on the flank per group) and administered with various drugs, intraperitoneal injection: gemcitabine, GSK-126, decitabine; and oral lavage: palbociclib. The following dose schedules were used: gemcitabine (2 mg/kg, 5 times/week), GSK-126 (2.5 mg/kg, 5 times/week), decitabine (2.5 mg/kg, 3 times/week), and palbociclib (150 mg/kg, 5 times/week). Gemcitabine, GSK-126, and decitabine were dissolved in DMSO and palbociclib was dissolved in distilled water. The EBV-positive cell line, C666-1, mice xenograft served as the control. Tumor dimensions were measured twice a week with calipers, and tumor volume was calculated with the formula, tumor volume ($mm^3$)=a (length, mm)×b2 (width, mm)×0.5. Tumors were harvested for further analysis. Three to five mice for each group were used. Mice were sacrificed ~1 month after chemical injection or earlier if tumors reached a size greater than 2000 $mm^3$, body weight loss exceeded 20%, mice were unable to maintain their normal food and water intake for 3 days, had micturition or defecation difficulties, or other conditions that would violate humane treatment regulations. Final tumor volumes were compared using two-way ANOVA adjusted for multiple comparisons.

Genomic DNA Extraction

Genomic DNA was extracted from PDX, FFPE, and plasma cell-free DNA using the QIAamp DNA mini kit, QIAamp DNA FFPE Tissue Kit (Qiagen), and QIAamp DNA blood mini kit (Qiagen), respectively, according to the manufacturer's instructions. Extracted DNA samples were quantified using a NanoDrop or Qubit™ dsDNA HS Assay Kit (Invitrogen). Genomic DNA integrity was determined with the Fragment Analyzer™ system (Advanced Analytical Technologies, Inc).

Quantitative Reverse Transcription PCR

10 µL of 2× SyBr (Bio-Rad BP170-8882AP), 0.6 µL of forward primer (10 µM), 0.6 µL of reverse primer (10 µM) and 8 µL cell-free DNA of plasma are added into a microtube for Q-PCR reaction. The Q-PCR reaction is performed in Roche LightCycler 96. After the reaction is completed, the Ct value of NLRP3 is converted as copy number 2. And Ct values of (1) CCND1, (2) CDKN2A and (3) RAD52 are compared with the Ct value of NLRP3 to calculate their copy number. The sequences of CCND1-forward primer (SEQ ID NO:1), CCND1-reverse primer (SEQ ID NO:2), CDKN2A-forward primer (SEQ ID NO:3), CDKN2A-reverse primer (SEQ ID NO:4), RAD52-forward primer (SEQ ID NO:5), and RAD52-reverse primer (SEQ ID NO:6) are listed in the sequence list.

Whole Exome Sequencing (WES)

Whole exome sequencing (WES) was performed on genomic DNA from NPC PDX tumors and their matched peripheral blood from the corresponding NPC patients (a) (NPC PDX-ST, -LN, -LG, -LV) (Macrogen, Korea, using SureSelectXT Lib. Prep. Kit, HiSeq 4000, Illumina) as well as (b) NPC PDX-Bone and PDX-LN (ACTgenomics, Taiwan).

Identification of Somatic Mutations from WES Data

Fastq files of WES obtained from Macrogen were filtered and (adaptor) trimmed. Sequencing reads from NPC PDX tumors (ST, LN, LG, LV) were aligned and filtered to the mouse reference genome, MM10, using the Burrows-Wheeler Aligner (BWA) tool. The remaining reads of PDX tumors and sequencing reads from matched patients' peripheral blood were aligned to the human reference genome, hg19, separately using BWA. Variants from both PDX tumor and normal samples were identified using the Genome Analysis Toolkit (GATK) pipeline. GATK Unified Genotyper was used to call SNVs and insertion/deletions (Indels) (Genomics, Taiwan).

ACTOnco Comprehensive Cancer Panel Sequencing (ACTgenomics)

Genomic DNA (80 ng) was amplified using four pools of 15992 primer pairs (Ion AmpliSeq Comprehensive Cancer Panel, Life Technologies) targeting all coding exons of the 409 cancer related genes. Amplicons were ligated with barcoded adaptors using the Ion Amplicon Library Kit (Life Technologies). Barcoded libraries were subsequently conjugated with sequencing beads via emulsion PCR and enriched using the Ion PI™ Hi-Q™ Chef Kit (Life Technologies). The quality and quantity of the amplified library were determined using fragment analyzer (AATI) and Qubit (Invitrogen). Sequencing was performed on the Ion Proton sequencer using the Ion PI™ Chip Kit v3 (Life Technologies) according to the manufacturer's protocol.

Analysis of Whole Exome Sequence Data

The library was constructed according to Ion AmpliSeq™ Exome RDY library preparation kit (ACTgenomics). Briefly, 50 ng genomic DNA was amplified using 12 pools of primer pairs (Ion AmpliSeq Exome RDY Kit, Life Technologies) to target all coding exons of 18,835 genes (about 57.7 Mb). Amplicons were ligated with barcoded adapters using the Ion Xpress™ barcode adapters kit (Life Technologies). Barcoded libraries were subsequently conjugated to sequencing beads via emulsion PCR and enriched with the Ion PI™ Hi-Q™ Chef Kit (Life Technologies). The quality and quantity of the amplified library were determined using the fragment analyzer (AATI) and Qubit (Invitrogen). Sequencing was performed on the Ion Proton sequencer using the Ion PI chip (Life Technologies) according to the manufacturer's protocol (ACT genomics). Raw reads generated by the sequencer were mapped to the hg19 reference genome using the Ion Torrent Suite (version 5.0) and coverage depth calculated using Torrent Coverage Analysis plug-in. Single nucleotide variants (SNVs) and short insertion/deletions (INDELs) were identified using the Torrent Variant Caller plug-in (version 5.0). Variant Effect Predictor (VEP) (version 77) was applied to annotate every variant with a database from COSMIC: v.70; dbSNP 138 and 1000 Genomes: phase 1. Variant coverage lower than 25 or frequency lower than 5% were filtered. Variants reported in the 1000 Genomes Project Phase 1 with >1% minor allele frequency (MAF) and those in the ACT Genomics in-house PBMC database were considered polymorphisms.

Copy Number Alteration Analysis

Amplicons of PDX-B and WBC-B with read counts in the lowest $5^{th}$ percentile of all detectable amplicons and those with coefficients of variation ≥0.3 were removed. The remaining amplicons from four different pools were normalized to correct the pool design bias. ONCOCNV was applied for normalization of total amplicon number, GC content, length, and technology-related bias, followed by segmentation of the sample with a gene-aware model. The method was additionally used for establishing the baseline of copy number variations from samples in the ACT genomics in-house PBMC database. Whole exome sequencing reads [Fastq format, NPC PDX and PBMC (-ST, -LN, -LG, -LV)] were mapped to the human reference genome, hg19, using the FANSe2 algorithm with 5% error tolerance. Uniquely mapped reads were employed for further analysis to avoid ambiguity. Read density was calculated for each gene and each sample as read count divided by exon length. The average read densities of normal karyotype WBC samples were used as the normalization standard. Read density of each gene and each sample was normalized against standard values (Changgong Biotech., Taiwan). Since all the samples were from male patients, normal copy numbers of autosomal chromosomes were set as 2 while those of sex chromosomes X and Y were set as 1. The copy number of each gene and sample was plotted accordingly.

RNA Sequence

RNA of PDX samples was extracted using TRIzol (Invitrogen) reagent following the manufacturer's protocol. The remaining DNA was eliminated by treatment with DNase I as recommended by the manufacturer. Intact PolyA+ mRNA was selected using the NEB Poly(A) mRNA Magnetic Isolation Module (New England Biolabs). mRNA libraries were constructed with the aid of the NEBNext Ultra RNA library prep kit for Illumina (New England Biolabs) following the manufacturer's protocol. Sequencing was performed on an Illumina HiSeq X Ten sequencer for 150 cycles. The high-quality reads that passed the Illumina filter were subjected to bioinformatics analyses (Changgong Biotech). Sequences were mapped to a combined reference sequence database containing human RefSeq-RNA, mouse RefSeq-RNA and EB virus sequences (NCBI accession: AY961628, DQ279927 and V01555) using the hyper-accurate mapping algorithm FANSe2 in the NGS analysis platform "Chi-Cloud" (http://www.chi-biotech.com). Reads mapped to the mouse reference sequences were discarded and splice variants merged. Gene expression levels were quantified using the RPKM method. Genes with at least 10 reads were considered quantifiable. Differentially expressed genes (DEG) were analyzed using the edgeR package (version 3.12.0) considering at least a 2-fold change and $p<0.05$. Gene ontology and pathway analyses of DEGs were performed using topGO (version 2.22.0) and KOBAS (version 2.0), respectively.

Antibodies

The western blot analysis is performed with 100 μg protein lysis/well. The antibodies used in this disclosure: RB1 (CusaBio PA003948), RB-P (Cell Signaling 9307), E2F1 (Santa Cruz SC-193), CDK2 (CusaBio PA001533), CDK4 (Santa Cruz SC-23896), CDK6 (Santa Cruz SC-8396), CCNE2 (Proteintech 11935-1-AP), CDKN2A (Prosci 4211), CDKN1A (Santa Cruz SC-6246), PCNA (Proteintech 10205-2-AP), and GAPDH (Santa Cruz FL-335).

Statistical Analysis

Cell line and tumor weight data are presented as means±SD. Final tumor volumes were compared using two-way analysis of variance (ANOVA). Correlations of CNV of RAD52, CCND1 and CCND2A with EBV DNA load were depicted via linear regression. Overall survival was calculated from the time of obtaining tissue for PDX to death, plotted via Kaplan-Meier curves, and compared using the log-rank test. In all analyses, p-values were two-tailed and data were considered statistically significant at p-values less than 0.05.

Figure 2A:
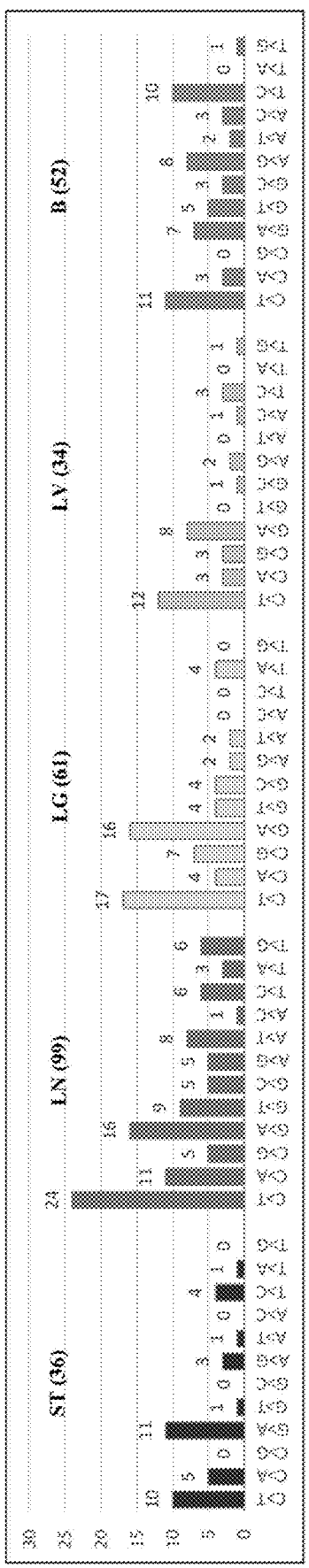
FIGS. 2A and 2B show single nucleotide variations (SNV) of five metastatic NPC-PDX tumors.
Figure 2B:
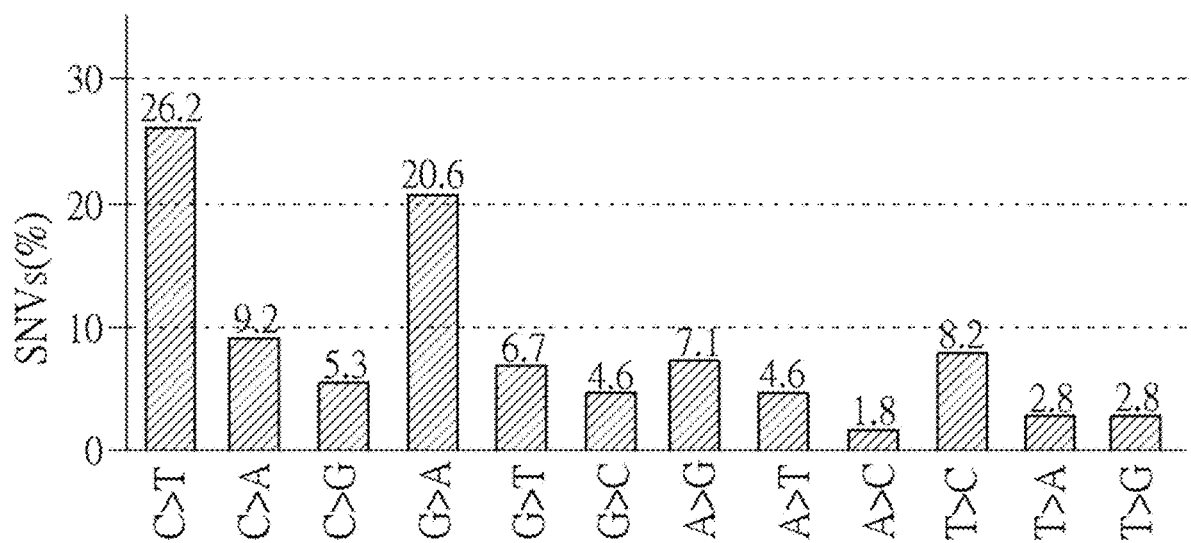
Figure 3A:
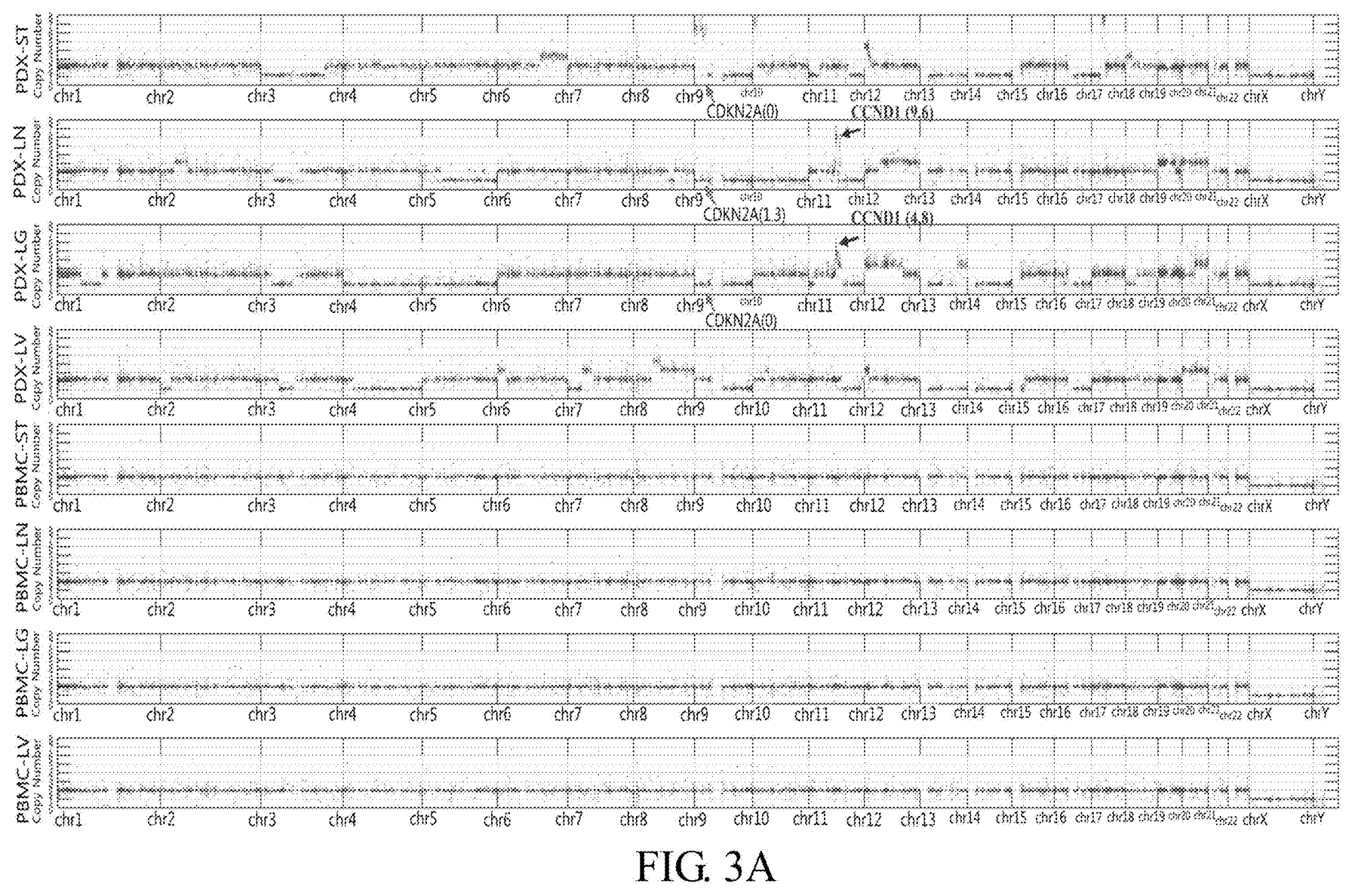

Example 1: Establishment of Six NPC-PDX Lines and Analysis of their Genomic Mutations Five NPC-PDX lines were successfully established from seventeen biopsy-proven NPC cases with local recurrence/metastasis between July 2013 and June 2016. The metastatic sites of the NPC-PDX parental tumors included soft tissue (ST), lymph node (LN), lung (LG), liver (LV) and bone. Tumor take rate for PDX-engraftment was about 30%. PDX engraftment positive patients had shorter survival than PDX engraftment-negative patients (p=0.033). It appears that oncogenic EBV, considered as potent mutation driver, accounts for relatively low mutation rate in NPC tumor. Consistent with previous results, we identified 34-99 single nucleotide variants (SNVs) for each tumor and a total 282 missense and splicing site somatic mutations (As shown in FIG. 2A) in five PDX tumors originated from metastasized NPC tumors when compared with the matched patient's peripheral blood mononuclear cells (PBMC). The predominant nucleotide changes were C to T (26.2%) and G to A (20%) transitions (As shown in FIG. 2B). In contrast to the limited somatic mutations in NPC PDX tumors, this example observed genome-wide CNV affecting thousands of genes (~5000 genes per PDX tumor). Several chromosome regions of PDX tumors showed arm-level aberrant amplification (CNV gain) or deletion (CNV loss) as shown in FIG. 3A. Interestingly, this example found that four out of five NPC-PDXs had CNV gain of cyclin D1, (CCND1, chr11-q13), and three NPC-PDXs had CNV loss of cyclin-dependent kinase inhibitor 2A, (CDKN2A, chr9-p21). CCND1 protein forms a complex with cyclin-dependent kinase (CDK)4/6 and subsequently phosphorylates retinoblastoma protein leading to entry of the S phase during cell cycle. CDKN2A protein, also known as p16, functions as a cell cycle inhibitor which binds to CDK4 and blocks the cyclin D1/CDK4/pRb axis by preventing cell cycle G1/S phase transition. Thus, amplification of CCND1 and deletion of CDKN2A are common alterations in NPC tumors, which may cooperatively contribute to rapid cell growth.

Example 2: PDX has High Genomic Fidelity to Parental Human NPC Tumors

Figure 3B:
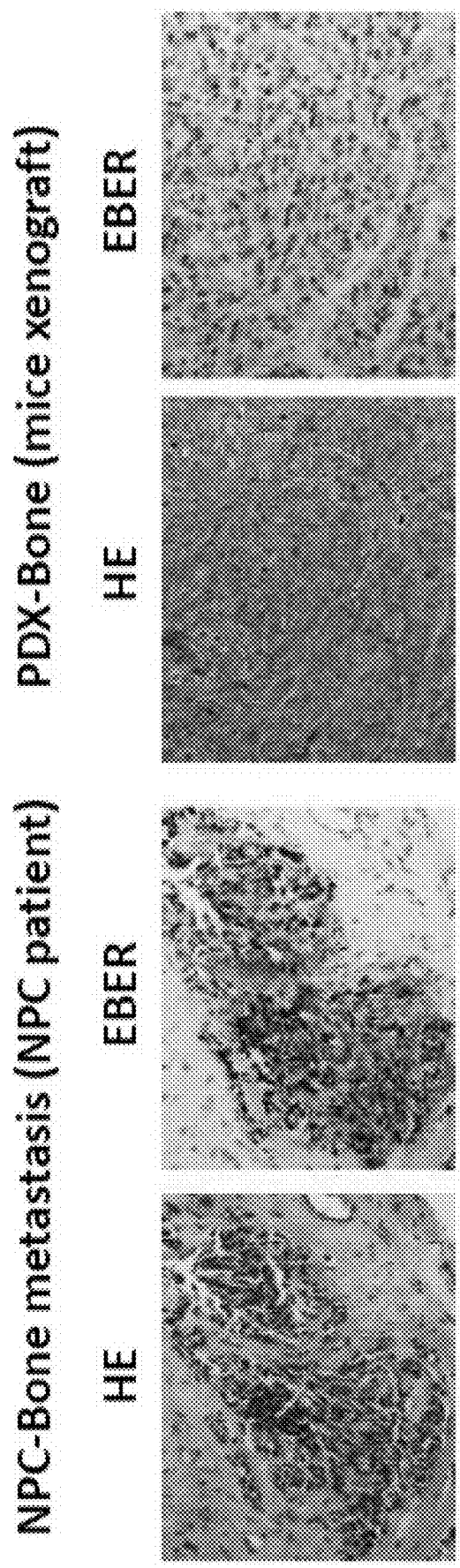
Figure 3C:
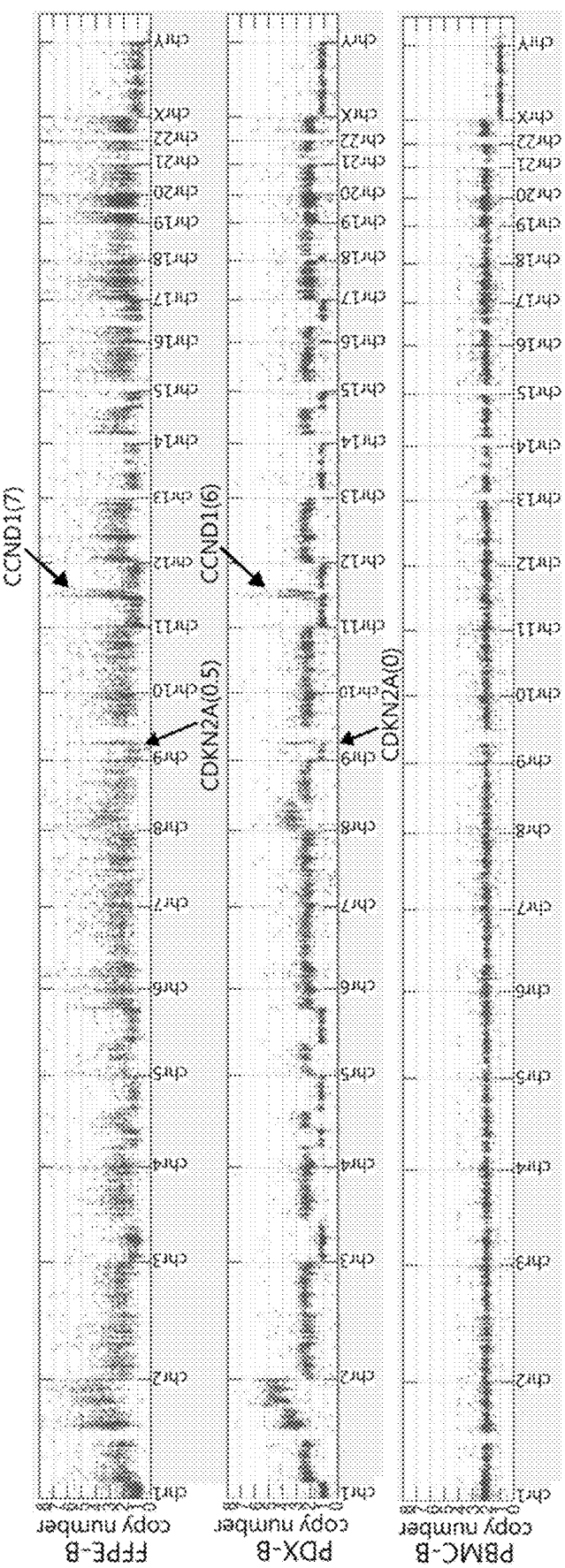
Figure 3D:
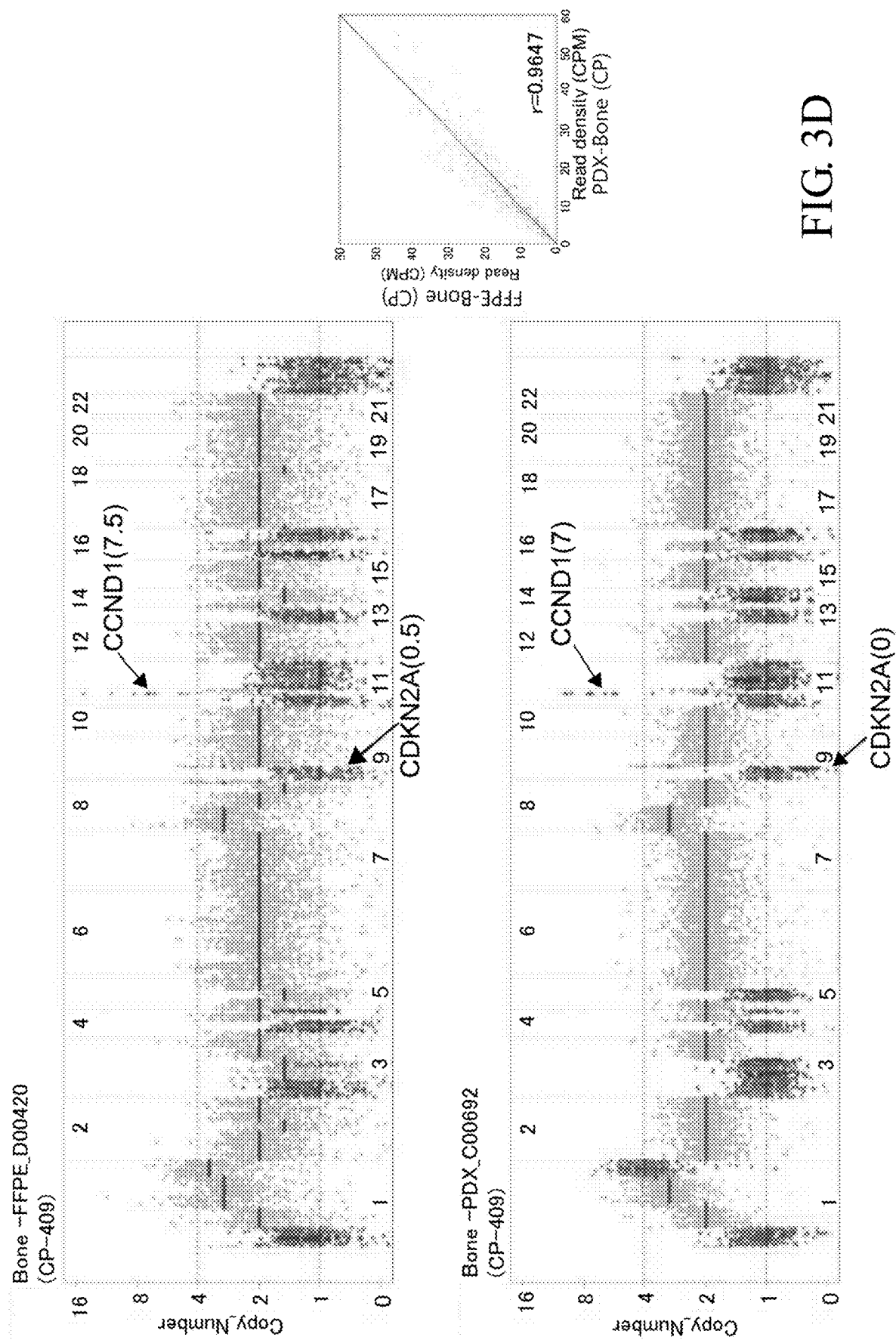
Figure 4A:
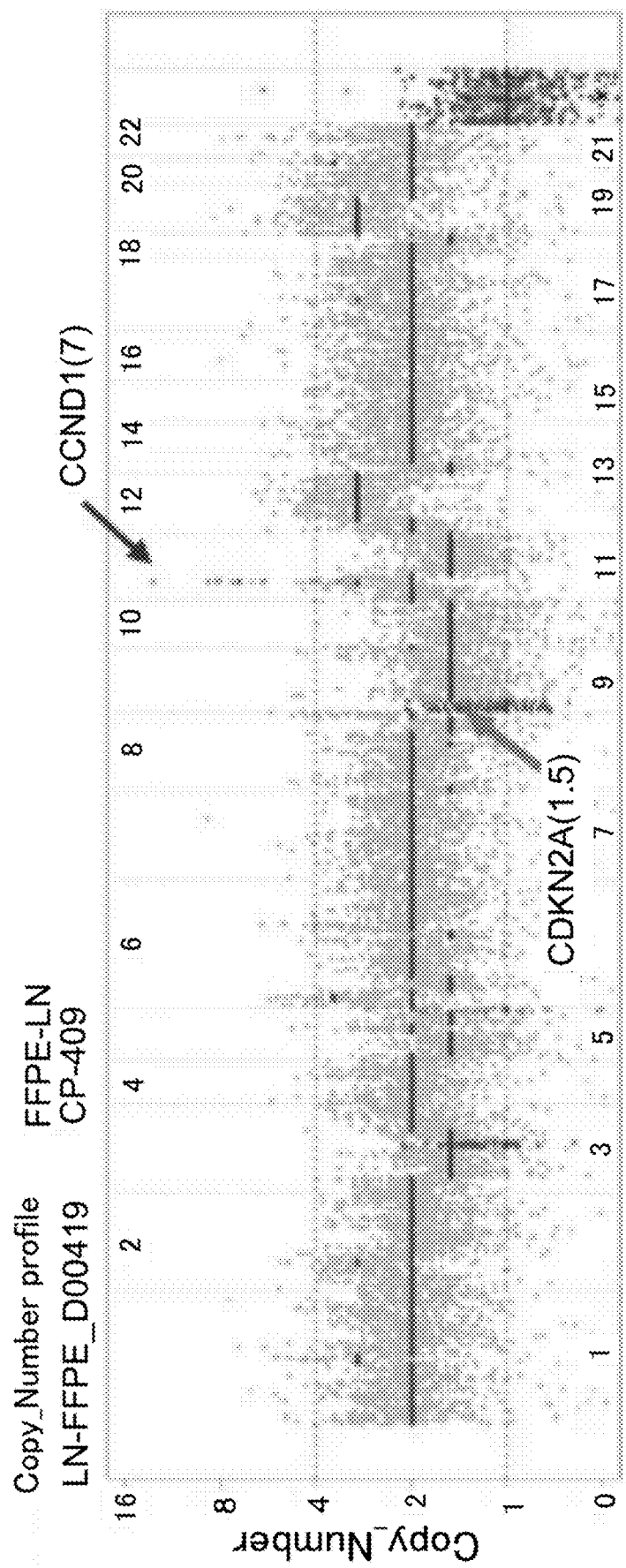
FIGS. 4A-4C show CNV profile comparison between CP-409, FFPE-LN and PDX-LN. CNV profiles of NPC FFPE-LN based on ultra-deep sequencing of CP-409 is shown in FIG. 4A. CNV profiles of PDX-LN based on ultra-deep sequencing of CP-409 is shown in FIG. 4B. Observed copy number for each evaluated position is shown on the y-axis as a log 2 scale. Genes associated with or without copy number alteration are indicated in different colors or in grey, respectively.
Figure 4B:
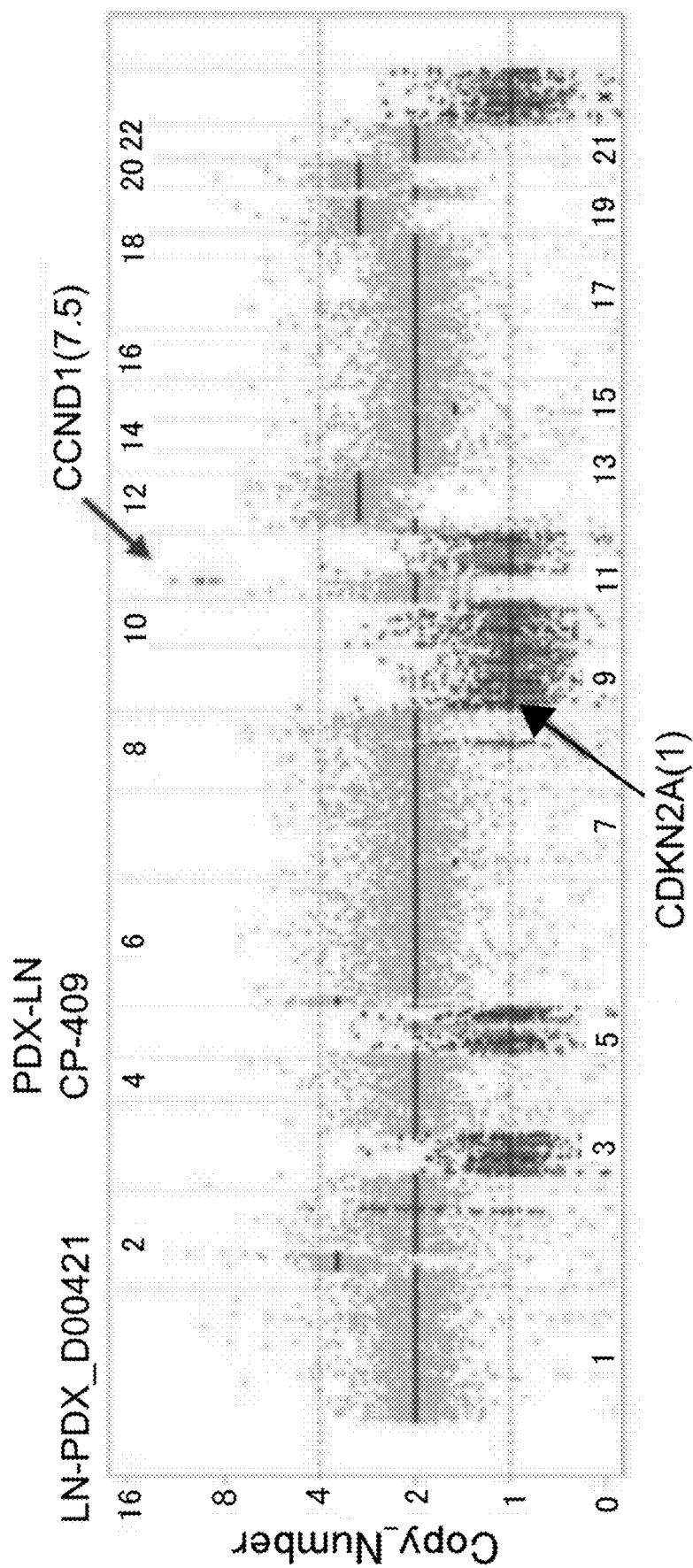
Figure 4C:
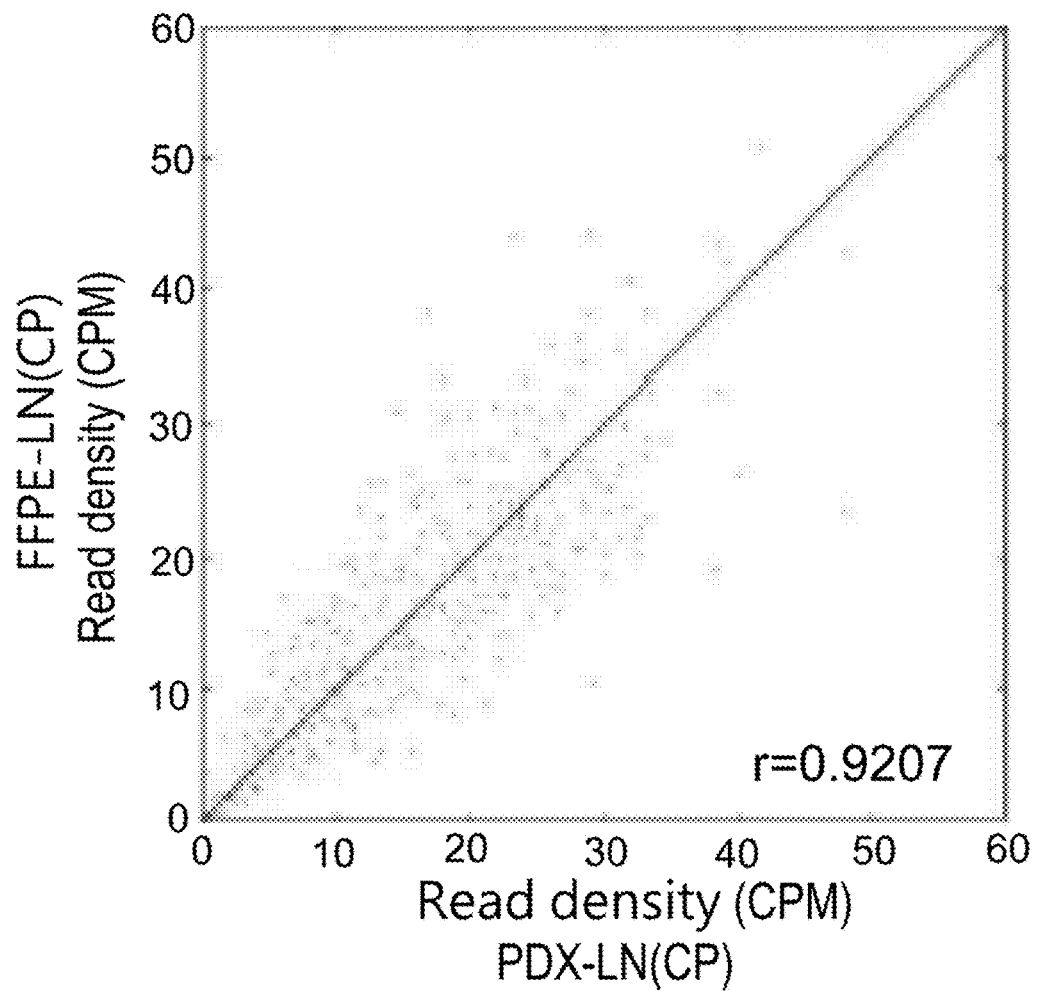

Both parental NPC metastatic tumors and PDX xenografts harbored EBV (with positive staining for Epstein-Barr encoding region, EBER), as shown in FIG. 3B. To determine whether the genetic compositions of PDX and original metastatic NPC tumors in patients (formalin-fixed, paraffin-embedded, FFPE) are similar, this example compared their copy number (CN) profiles obtained from whole exome sequencing (with 18,070 cellular genes) and Ultra-deep sequencing cancer panel 409 (ACTOnco CP-409, containing 409 selected oncogenes and tumor suppressor genes). Pair-wise comparisons revealed high correlation between the CN profiles of FFPE-Bone and PDX-Bone in both WES (Pearson correlation coefficient, r=0.62; FIG. 3C) and CP-409 (r=0.96; FIG. 3D). Comparable results were obtained when comparing the CN profiles of FFPE-LN and PDX-LN in CP-409 (r=0.92; FIGS. 4A to 4C). The high correlations between the CN profiles of FFPE samples and PDX tumors indicating that the PDX tumors retain the genetic composition of the parental NPC tumors. Due to the limited somatic mutations in each NPC-PDX tumor sample, this example incorporated all the SNVs identified in 282 genes as well as CCND1 and CDKN2A to perform pathway analysis (Metacore). The altered cancer-related pathways identified in the NPC PDX tumors are summarized in the following Table 1; and the most affected pathway was cell cycle. This findings signify that amplification and/or deletion of the specific cell cycle regulators CCND1 and CDKN2A are prominent abnormalities that may correlate with NPC tumorigenesis.

TABLE 1

The summary of the cancer-related somatic mutations and CCND1 CNV gain and CDKN2A CNV loss of the 5 NPC-PDX tumors.

| Pathway | Gene | PDX-ST 01 | PDX-LN 02 | PDX-LG 03 | PDX-LV 04 | PDX-B 13 |
|---|---|---|---|---|---|---|
| Cell cycle | CCND1 | | CNV gain 9.6 | CNV gain 4.8, missense | | CNV gain 6 |
| | CDKN2A | CNV loss 0 | CNV loss 1.3 missense | CNV loss 0 | | CNV loss 0 |
| | ANAPC7 | | | | | |
| | CCNB1 | | | | | missense |
| | CCNB3 | missense | | | | |
| | CDC7 | | | missense | | |
| Tumor Suppressor Genes | AIM1 | | | missense | | |
| | DLEU7 | | | | | missense |
| | ING1 | | | | missense | |
| | TIMP3 | | Splice site | | | |
| Immunity | HLA-A | | | | Stop gain | |
| | HLA-DQA2 | | missense | | | |
| | HLA-DRB5 | | | missense | | |
| | IL1R2 | | | | missense | |
| | TLR3 | | missense | | | |
| DNA repair | TP53 | | | | Stop gain | |
| | BRIP1 | | | | | missense |
| Epigenetic modifiers | TET3 | missense | | | | |
| | KDM2A | | | missense | | |
| Cytoskeleton | ARHGEF12 | Stop gain | | | | |
| | ARHGEF3 | | | | | missense |
| Drug Resistance | ABCG1 | | | | missense | |

Figure 5A:
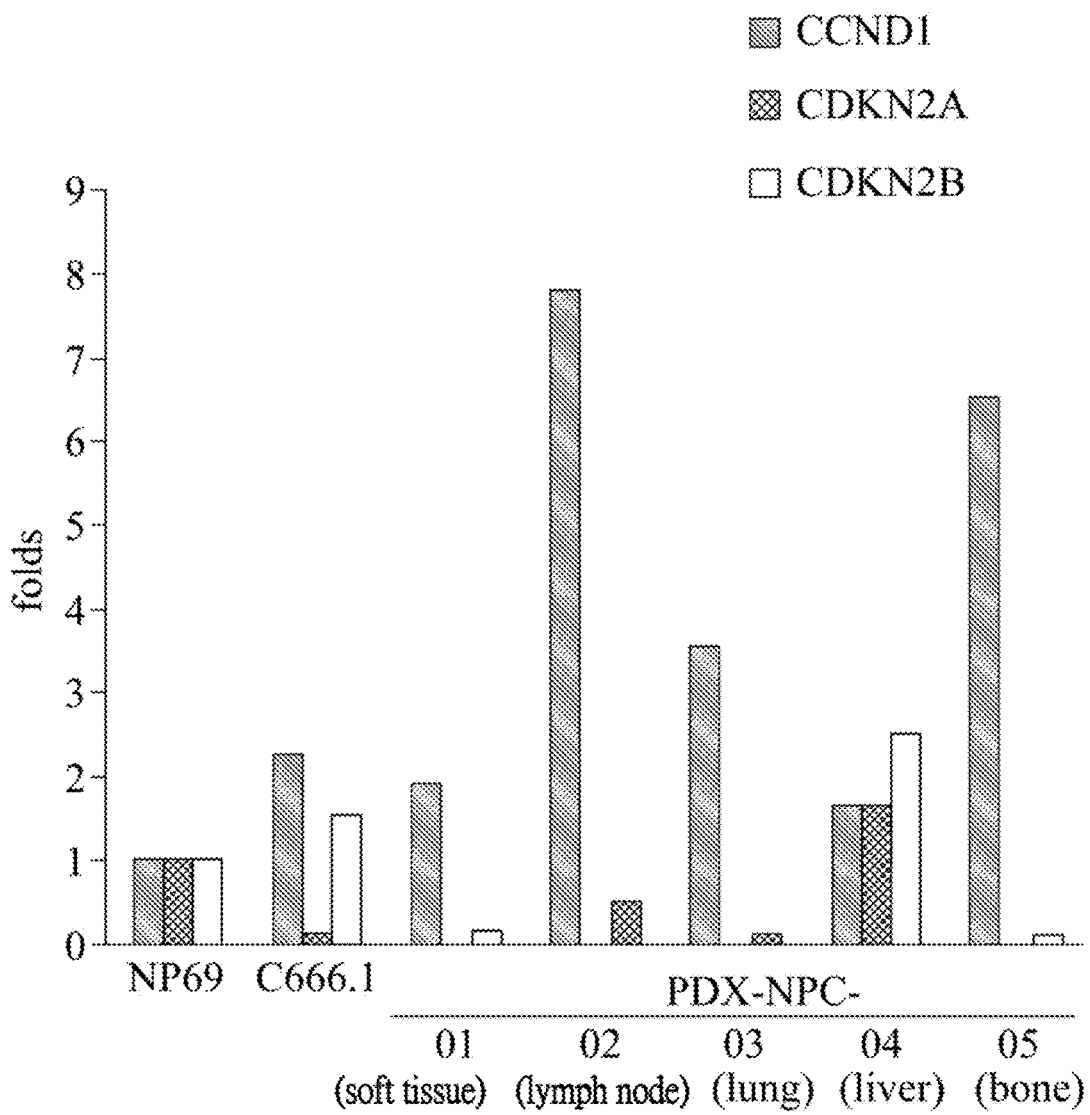
FIGS. 5A-5D show CCND1 mRNA expression and IHC staining in NPC patients and PDX tumors.
Figure 5B:
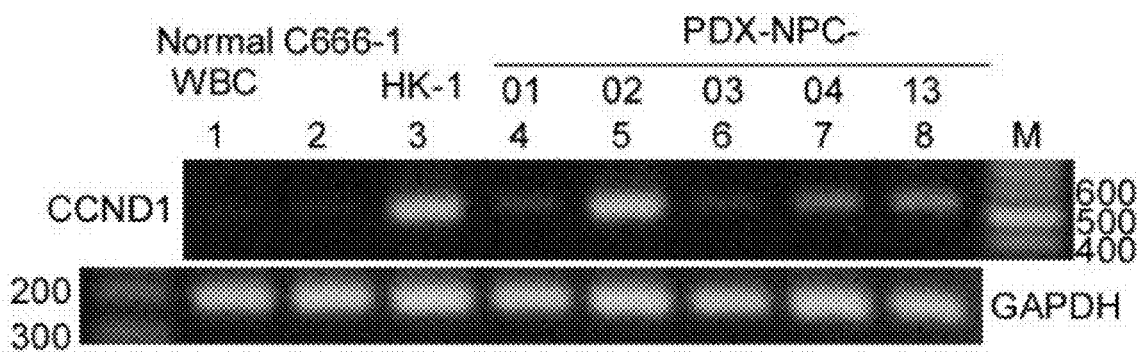
Figure 5C:
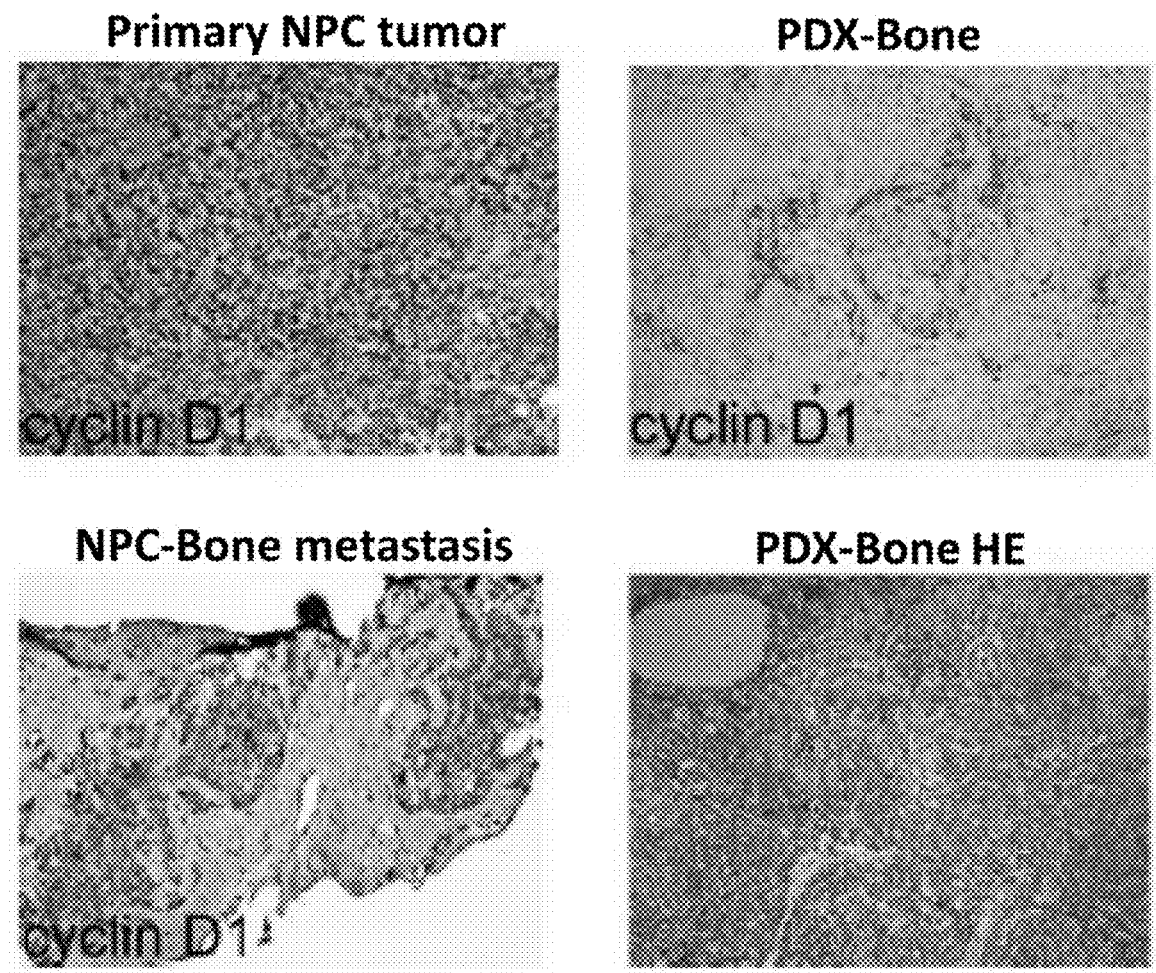
Figure 5D:
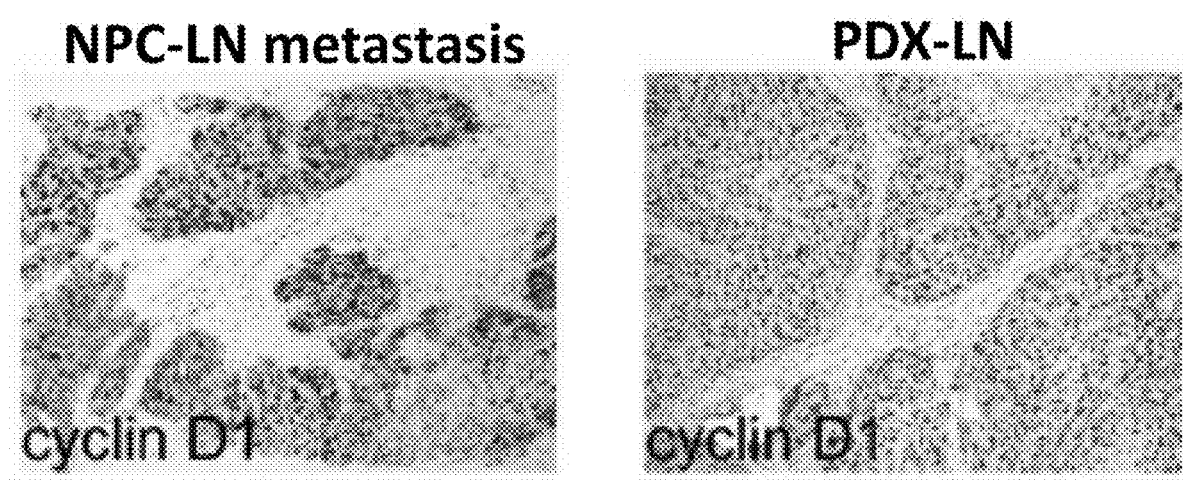

Example 3: Confirmation of CCND1 Overexpression Via WES and CNV Genetic Studies Microarray analyses confirmed cyclin D1 overexpression and silencing of CDKN2A and 2B in the four out of five PDXs, as shown in FIG. 5A. CCND1 mRNA overexpression (RT-PCR) was observed in NPC cell line (HK1) and five PDX tumors, (FIG. 5B). Immunohistochemical analyses further validated CCND1 protein overexpression in both parental metastatic NPC tumor and in PDXBone and PDX-LN, respectively (FIGS. 5C and 5D).

Example 4: NPC-PDXs Drug Screening

Figure 6A:
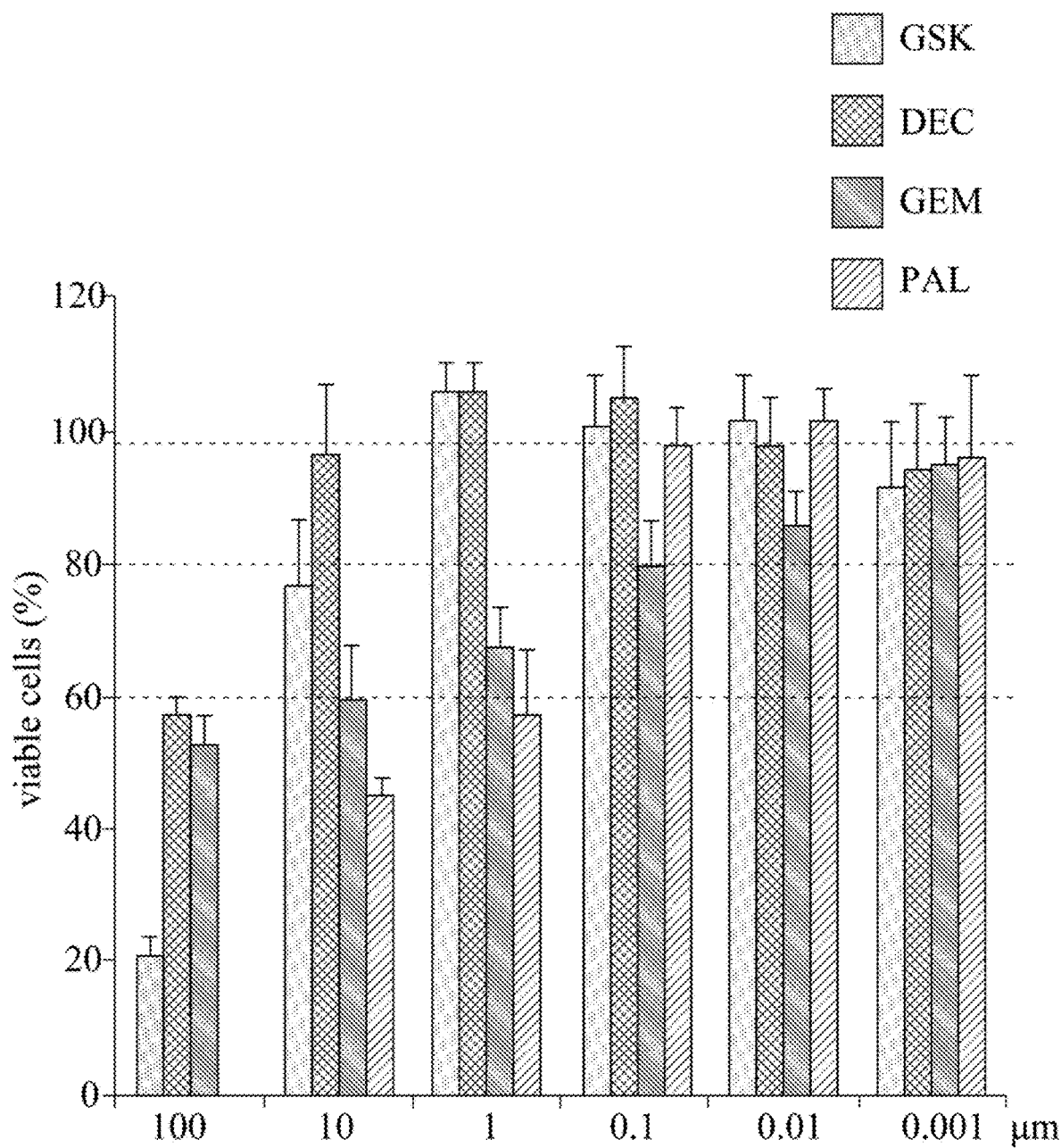
FIGS. 6A-6E: C666.1 cells and PDX-C666.1 xenograft drug screening.
Figure 6B:
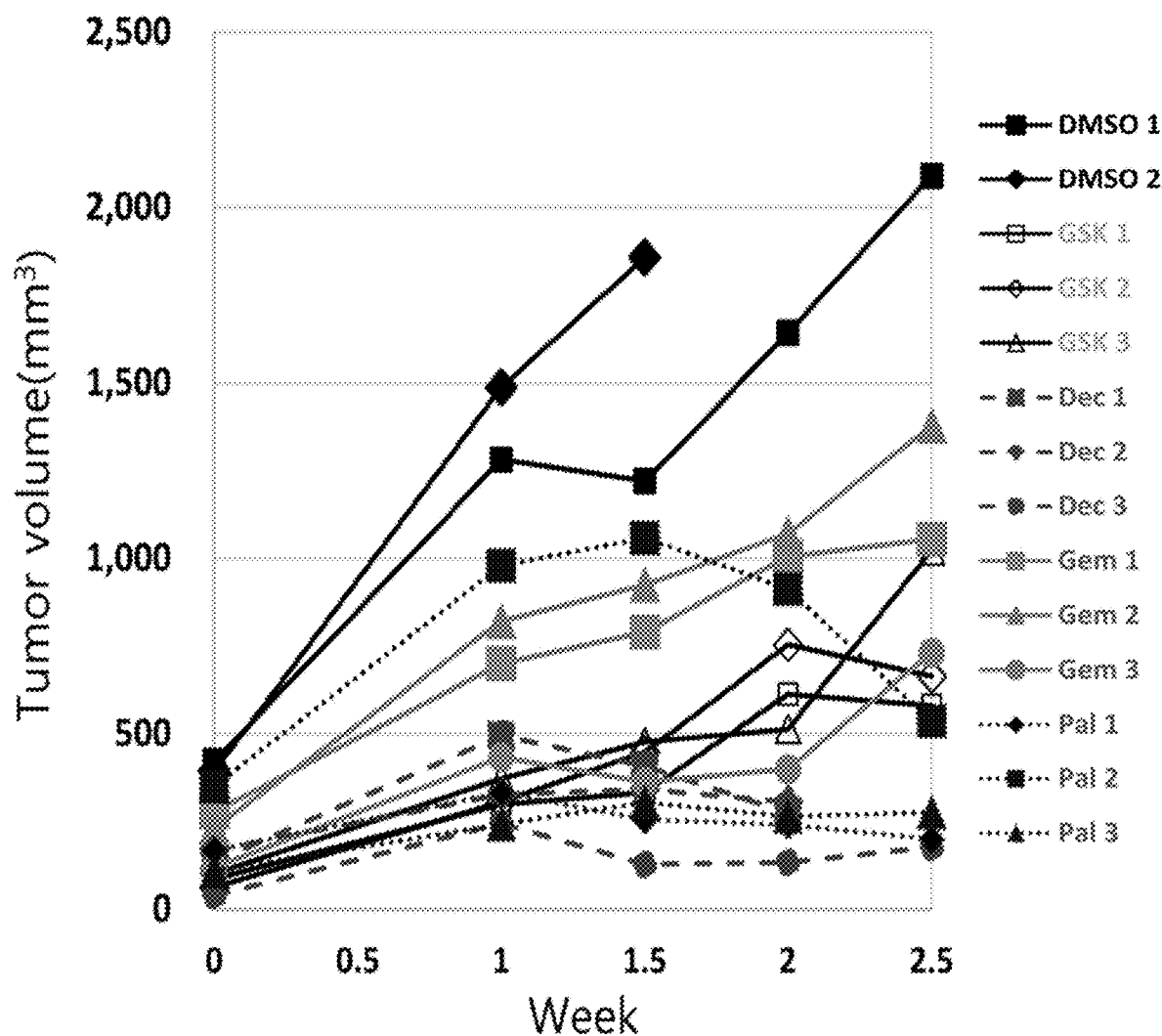
Figure 6C:
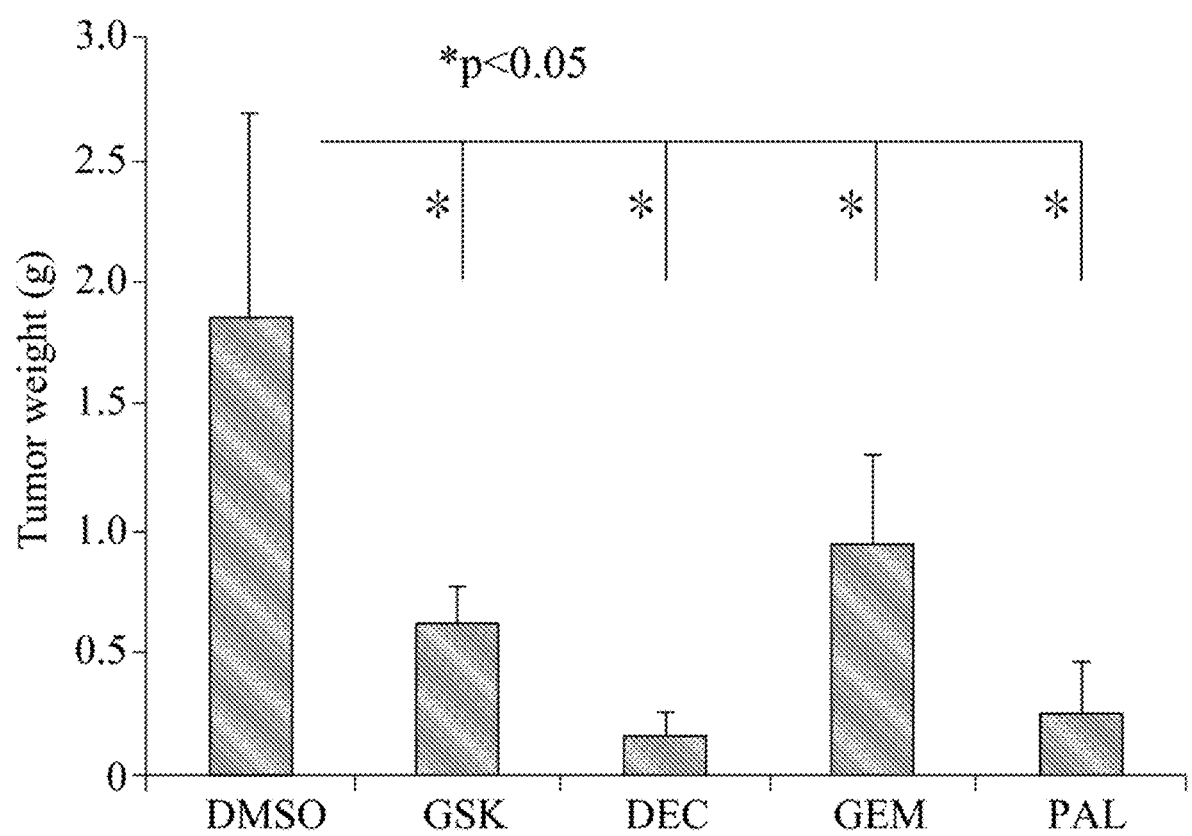
Figure 6D:
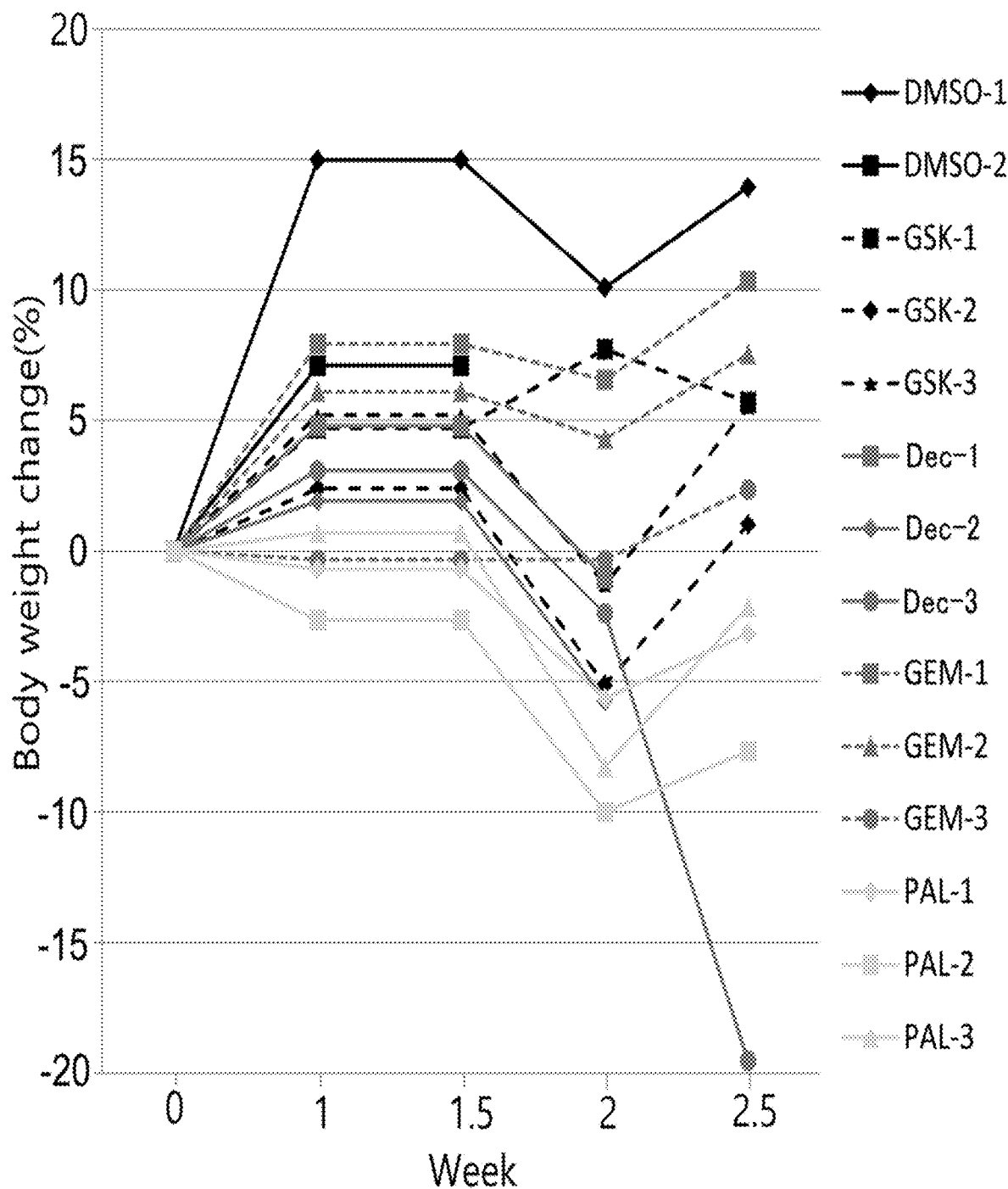
Figure 6E:
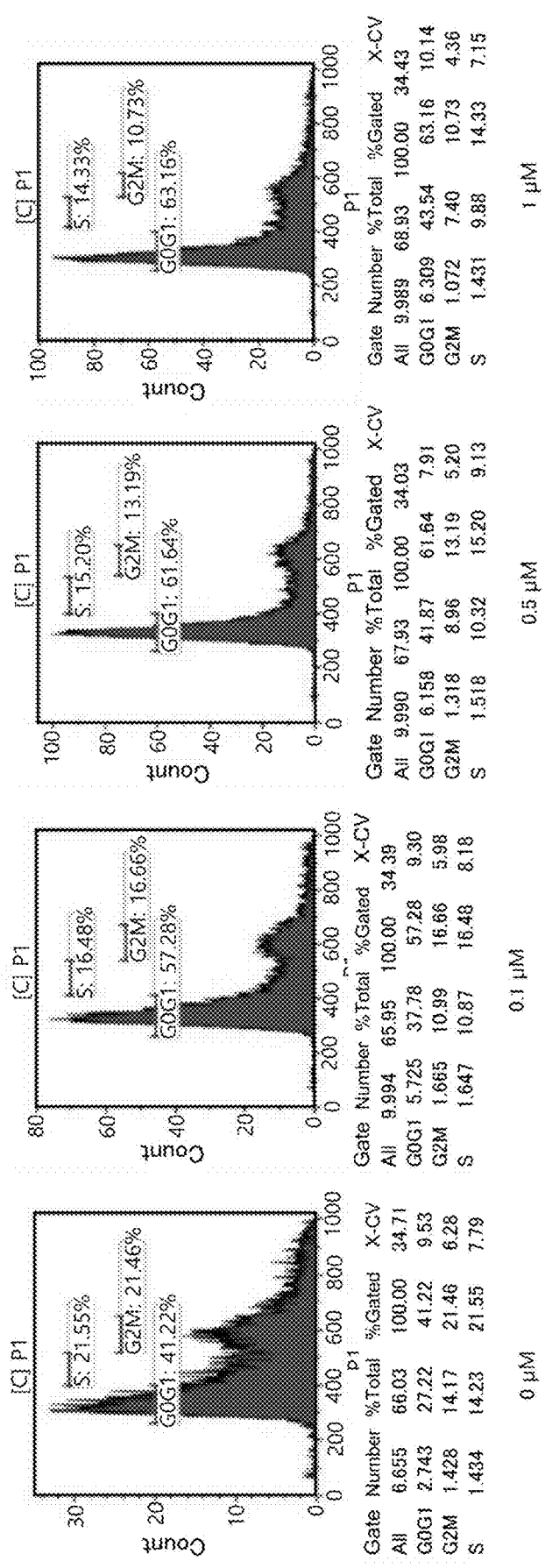
Figure 7A:
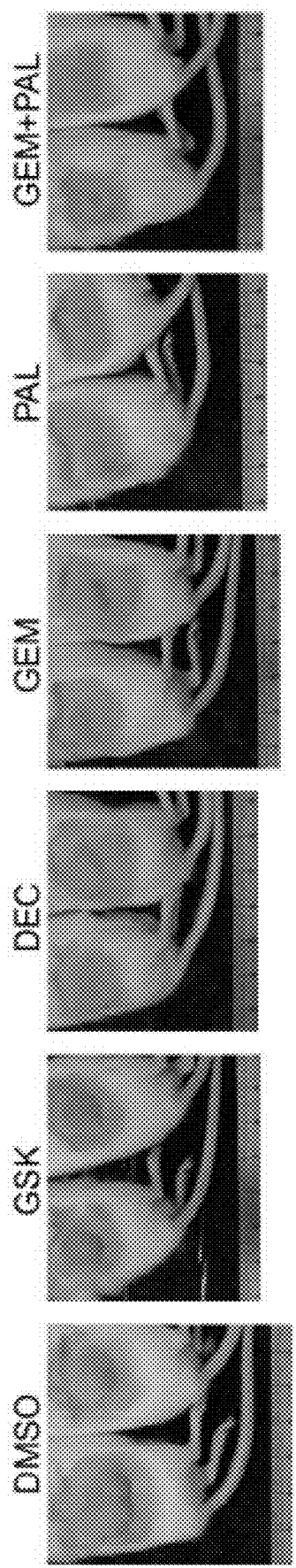
FIGS. 7A-7H: NPC-PDX drug screening.
Figure 7B:
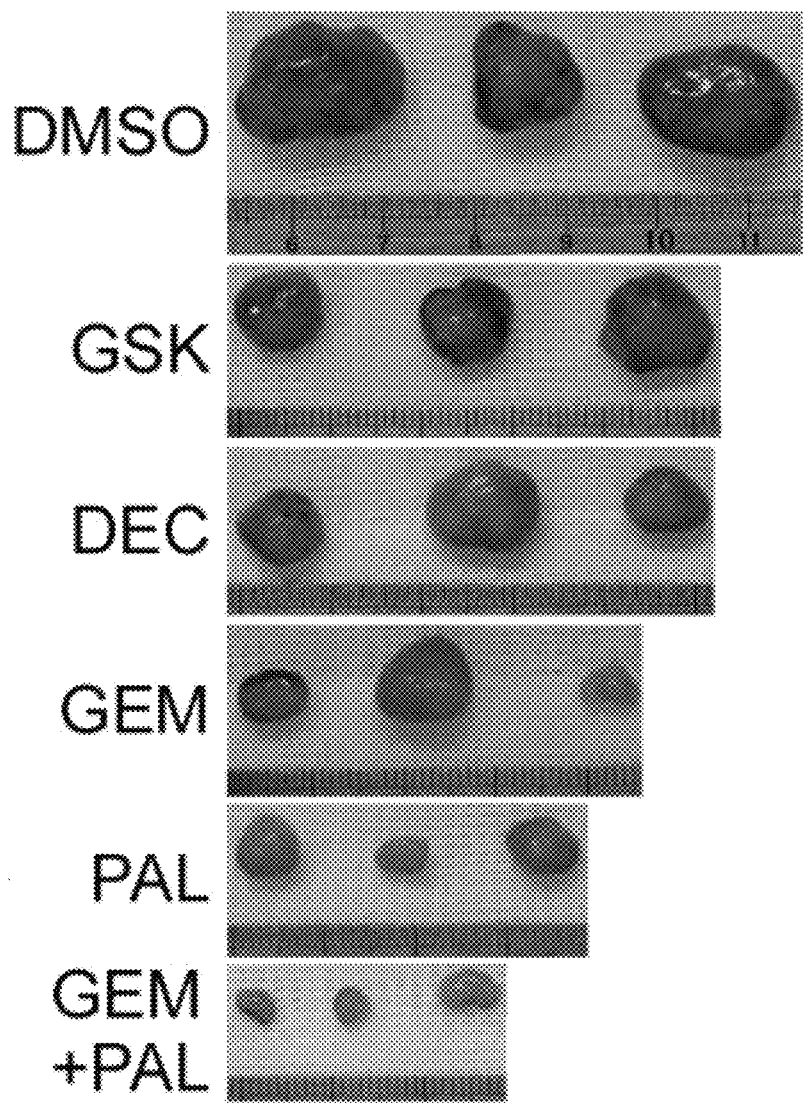
Figure 7C:
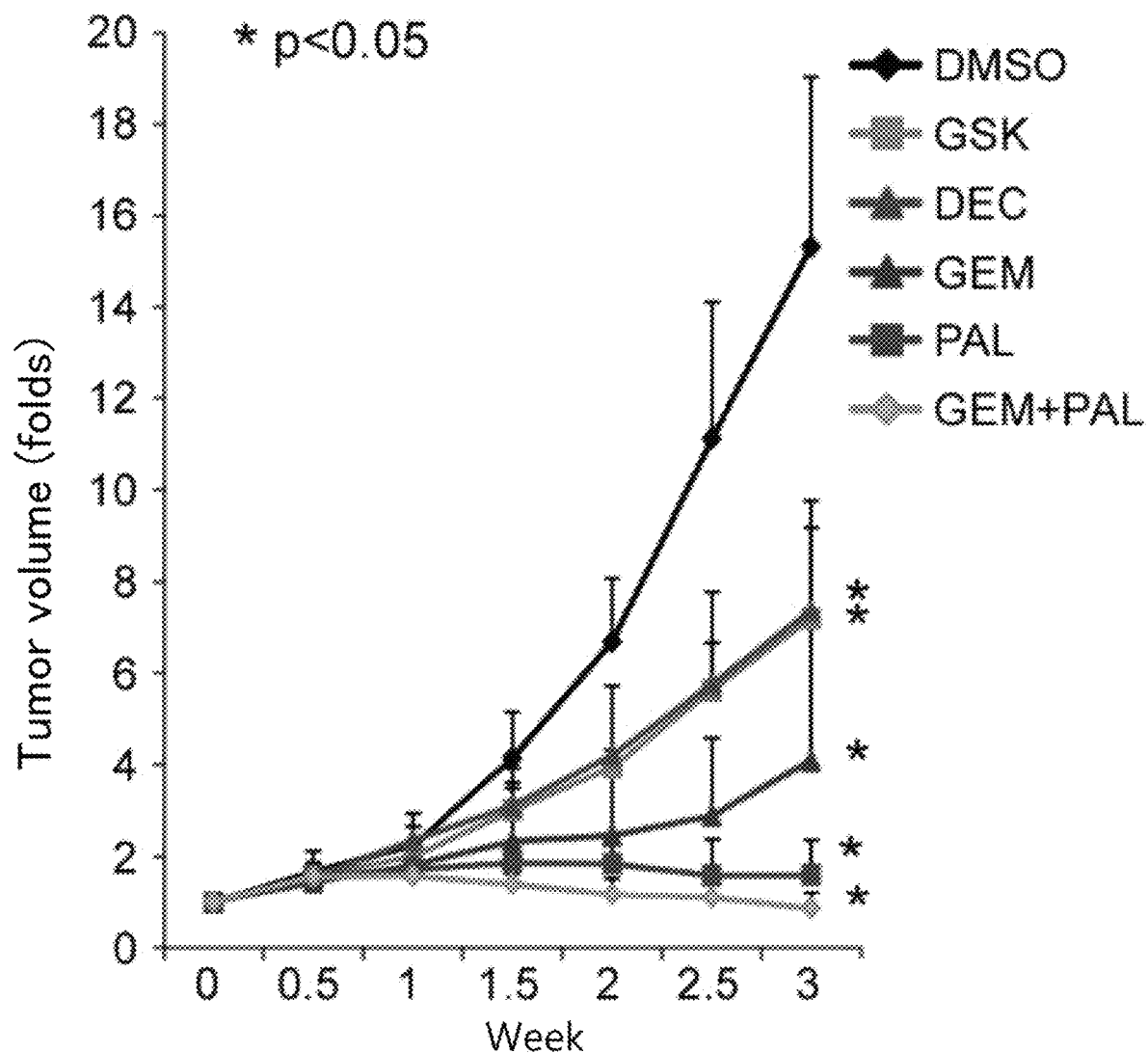
Figure 7D:
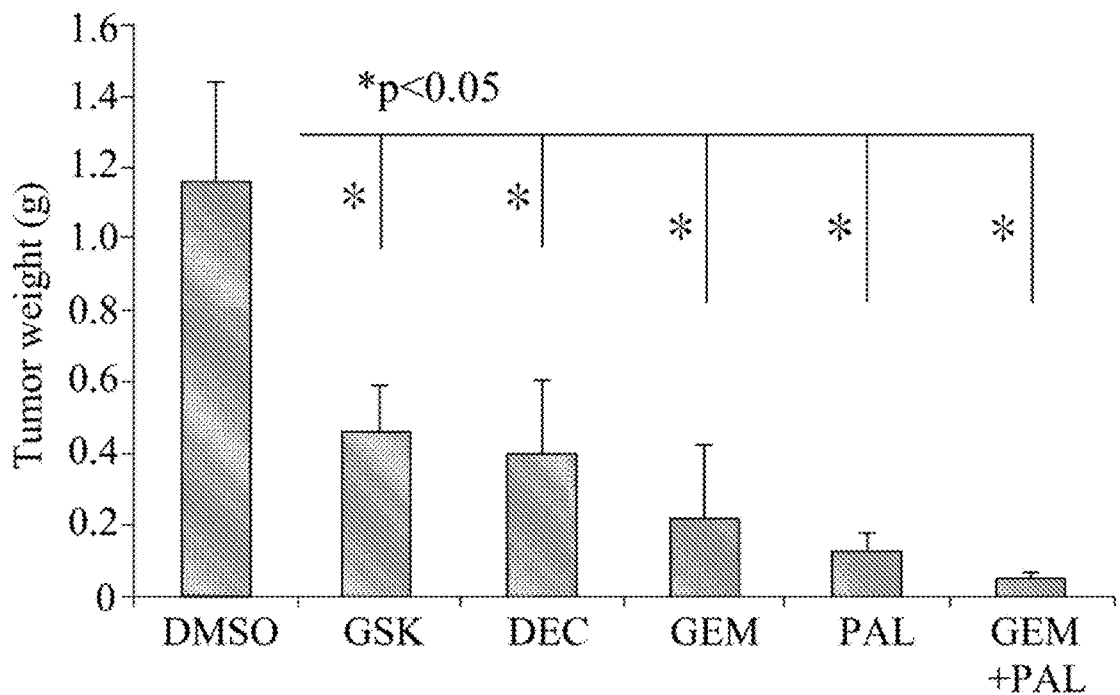
Figure 7E:
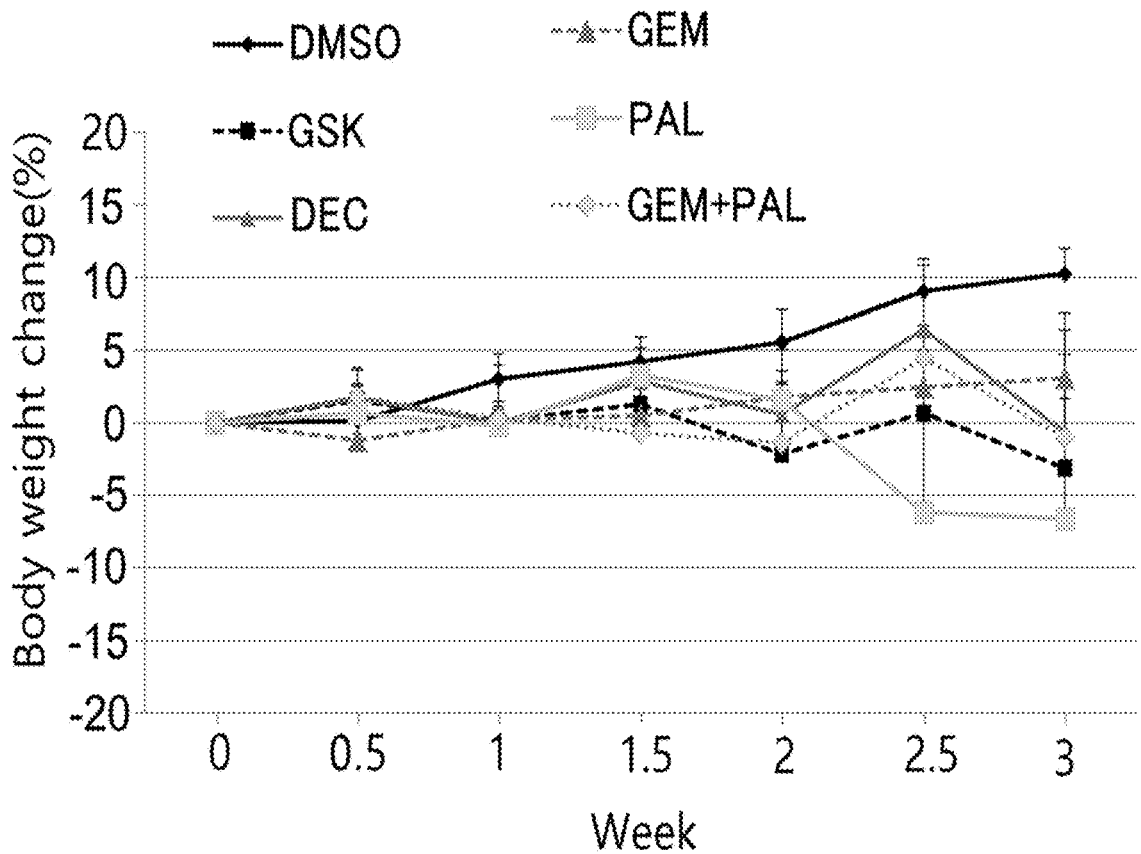
Figure 7F:
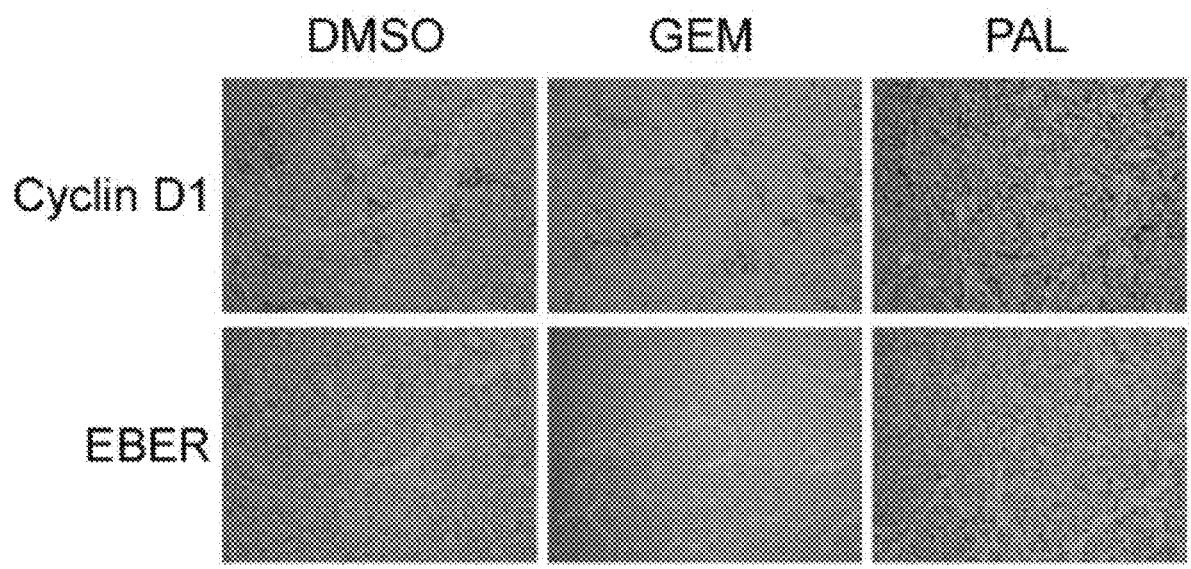
Figure 7G:
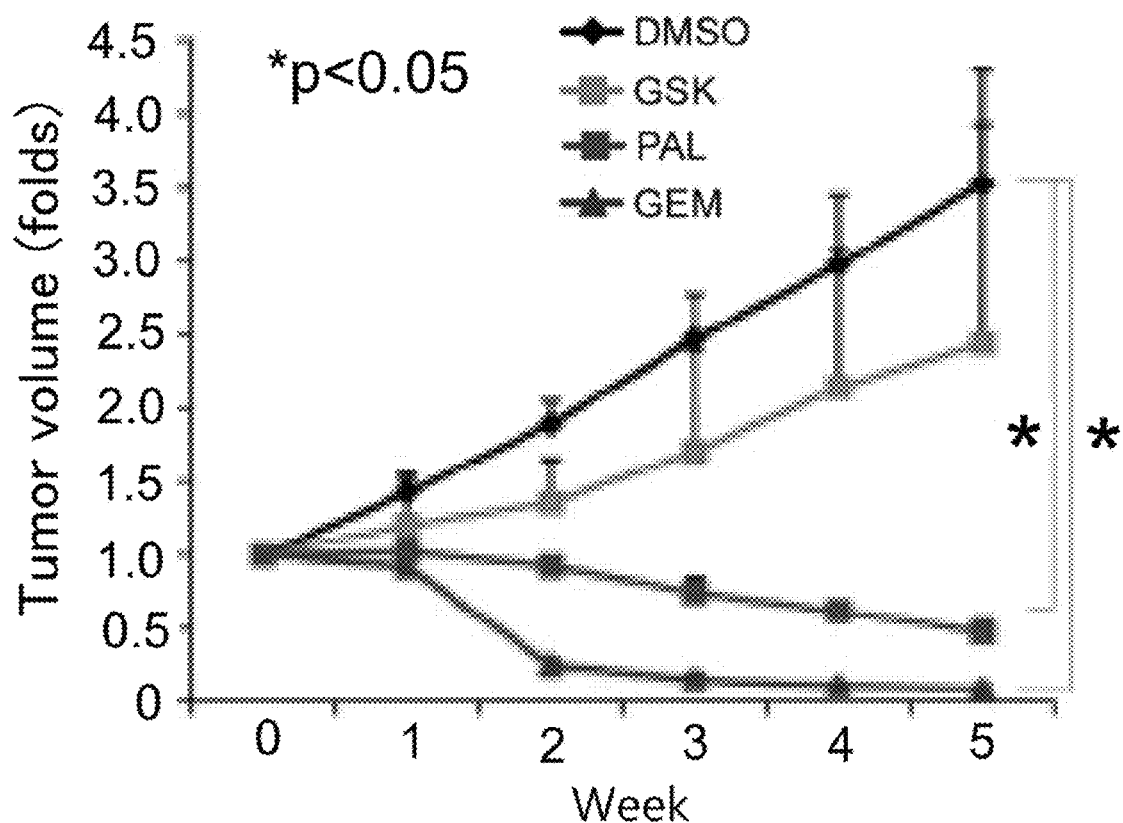
Figure 7H:
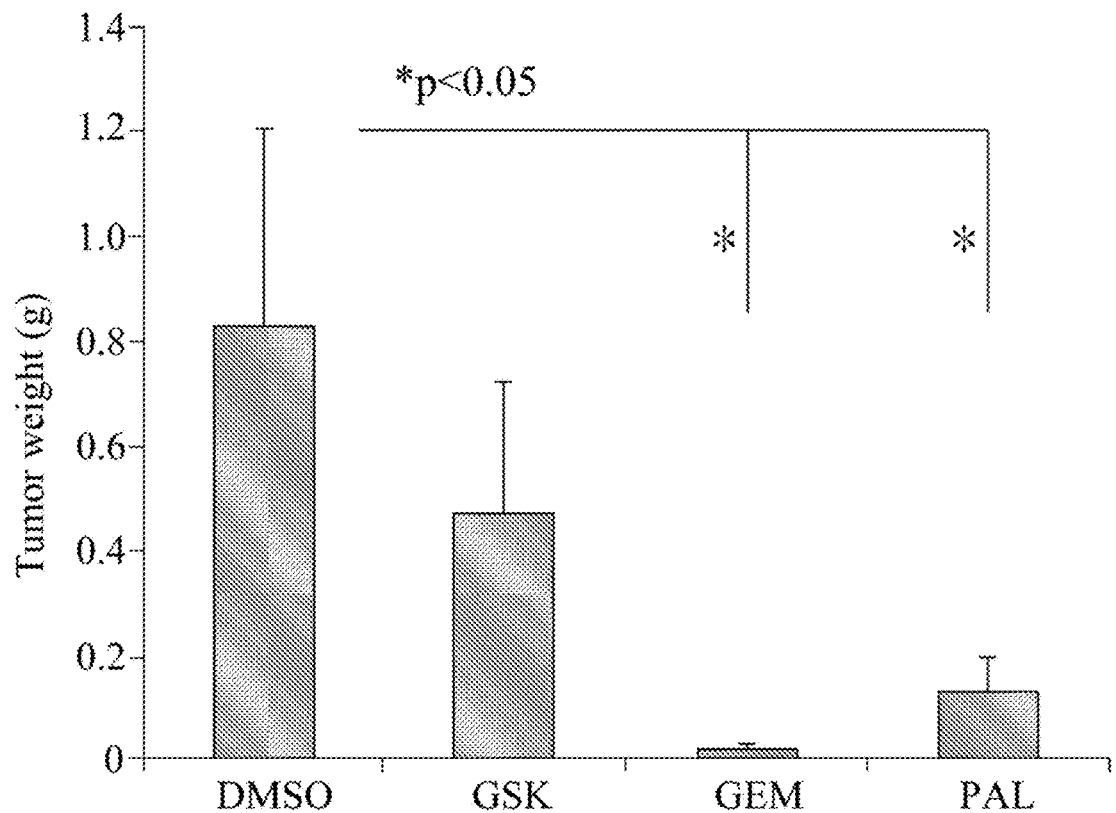
Figure 8A:
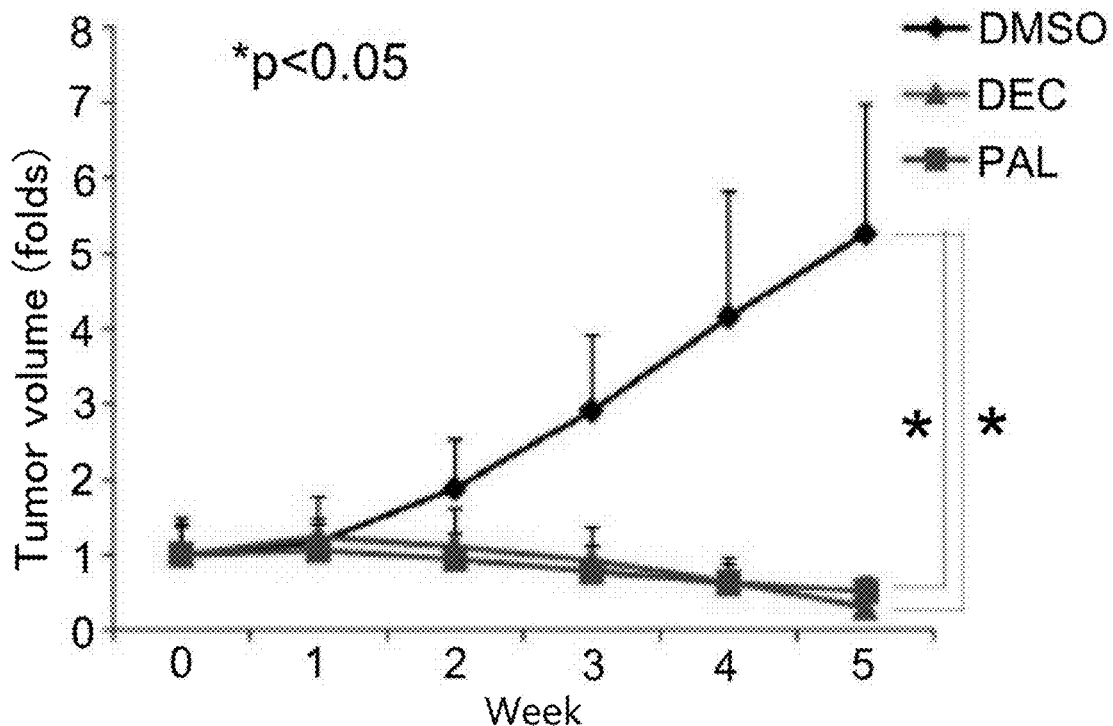
FIGS. 8A-8C: Drug screening in PDX-LN (NPC02F12). PDX-LN (FIG. 8A) tumor volume.
Figure 8B:
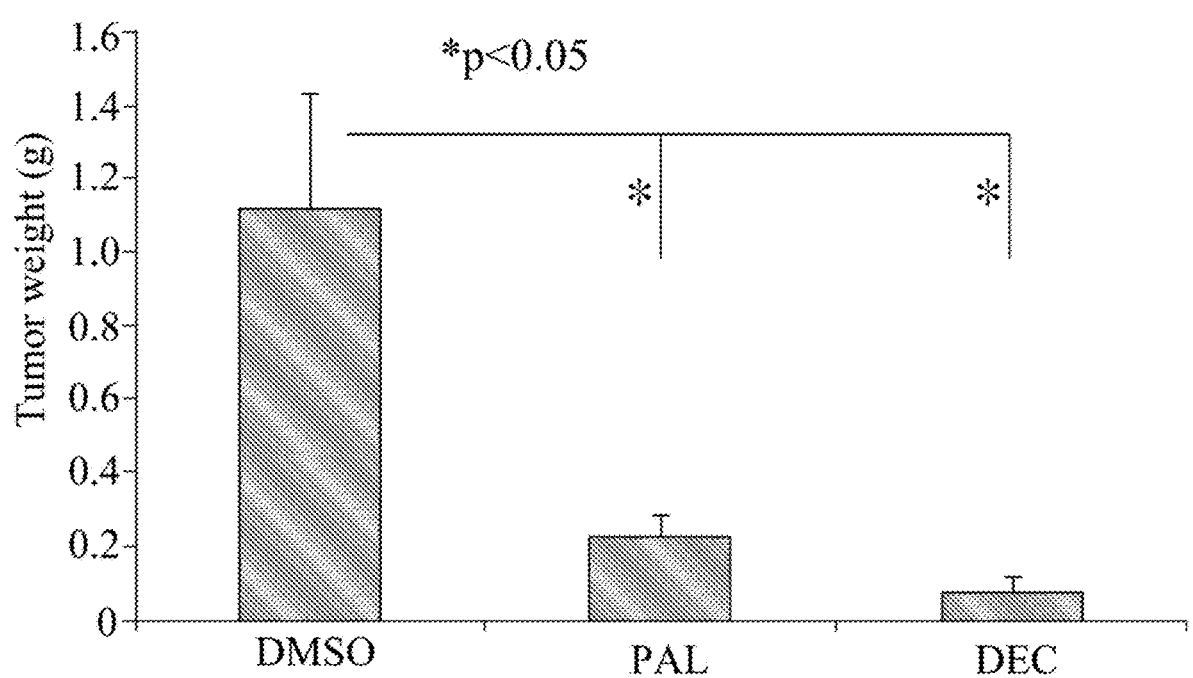
Figure 8C:
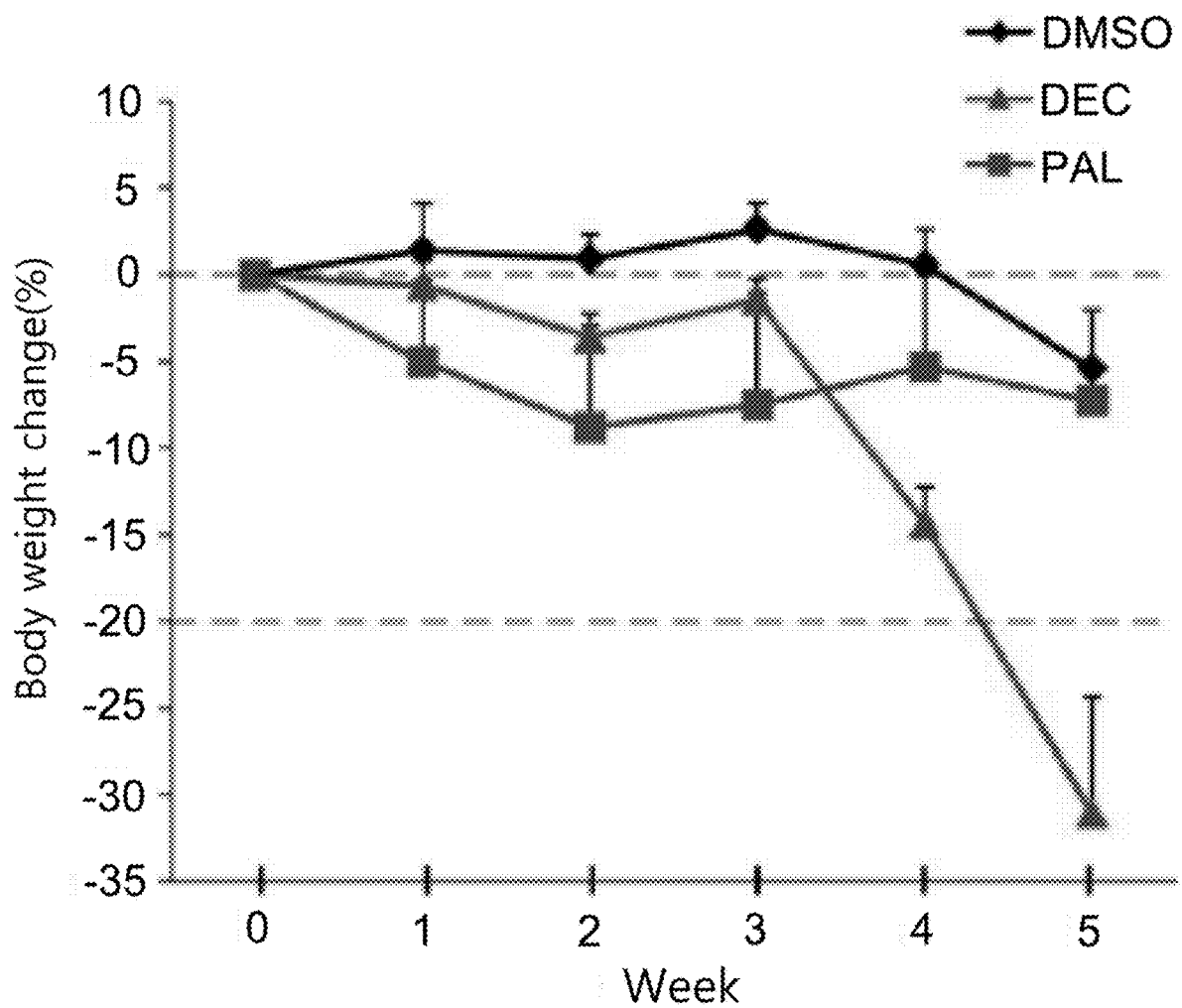

Based on the mutations discovered by integrated genomic analyses in NPC-PDXs, this example is to test whether cell cycle inhibitor may be used as anti-cancer drug in the NPC-PDX lines which is establish in example 1. This example selected a FDA approved cell cycle inhibitor "palbociclib" (PAL, CDK4/6 inhibitor) currently used in breast cancer. There are reports indicated that overexpression of epigenetics modifiers, Enhancer of Zeste homolog 2, protein methyltransferase, (EZH2) and DNA methyltransferase 1 (DNMT1) in NPC correlated with NPC tumorigenesis; thus, this example chose EZH2 inhibitor "GSK126" and DNA methylation inhibitor "decitabine" (a nucleotide analogue of DNMT1) in NPC-PDX drug screening model. As comparison, a conventional NPC chemo-drug "gemcitabine" (GEM, a nucleotide analogue) was also included. These four drugs (GEM, GSK, DEC, and PAL) were first tested in an EBV-positive cell line, C666-1. The IC50 value for PAL and GSK was in the range of 10-100 μM in the C666-1 cell (as shown in FIG. 6A). Then these four drugs were used in PDX-C666.1 xenograft, all four drugs exerted suppressive effects on C666-1 xenograft growth when compared with DMSO control (as shown in FIGS. 6B and 6C). Although DEC displayed toxicity to some extent, inducing body weight changes of >20% or death in mice during treatment (as shown in FIG. 6D). To confirm PAL can induce growth arrest at the $G_0G_1$ phase, C666-1 cells were treated with 0.1, 0.5 and 1 μM PAL for 48 h and followed by flow cytometry analysis. The percentage of cells at the $G_0G_1$ phase in the PAL-treated cells increased in a dose-dependent manner when compared with that of control (DMSO) (as shown in FIG. 6E), indicating PAL blocks NPC cells from entering S phase. In NPC-PDX-13-F4 (PDX-Bone passage 4) line, all four tested drugs significantly suppressed both the size (FIGS. 7A-7C) and gross weight of tumors in mice (FIG. 7D) relative to DMSO with tolerable body weight changes (FIG. 7E). Combination treatment with PAL and GEM induced an additive effect, compared to either GEM or PAL alone. CCND1 IHC staining after drug treatment revealed homogenous overexpression in the PAL-treated group (FIG. 7F), implying that the drug arrests the cell cycle of cancer cells at G1/S phase. In NPC-PDX-02-F11 (PDX-LN passage 11) line, both GEM and PAL exerted significant suppressive effects on xenograft growth, but not GSK (FIGS. 7G and 7H). Although DEC exerted anti-tumor growth in PDX-LN, it induced toxicity and led to >20% body loss (FIG. 8C). Thus, GEM and PAL had anti-tumor activity with little adverse effects in two NPC-PDX models (as shown in FIG. 8A-8B).

Example 5: Transcriptomic Analysis of NPC PDX-B with Various Drug Treatments

Figure 9A:
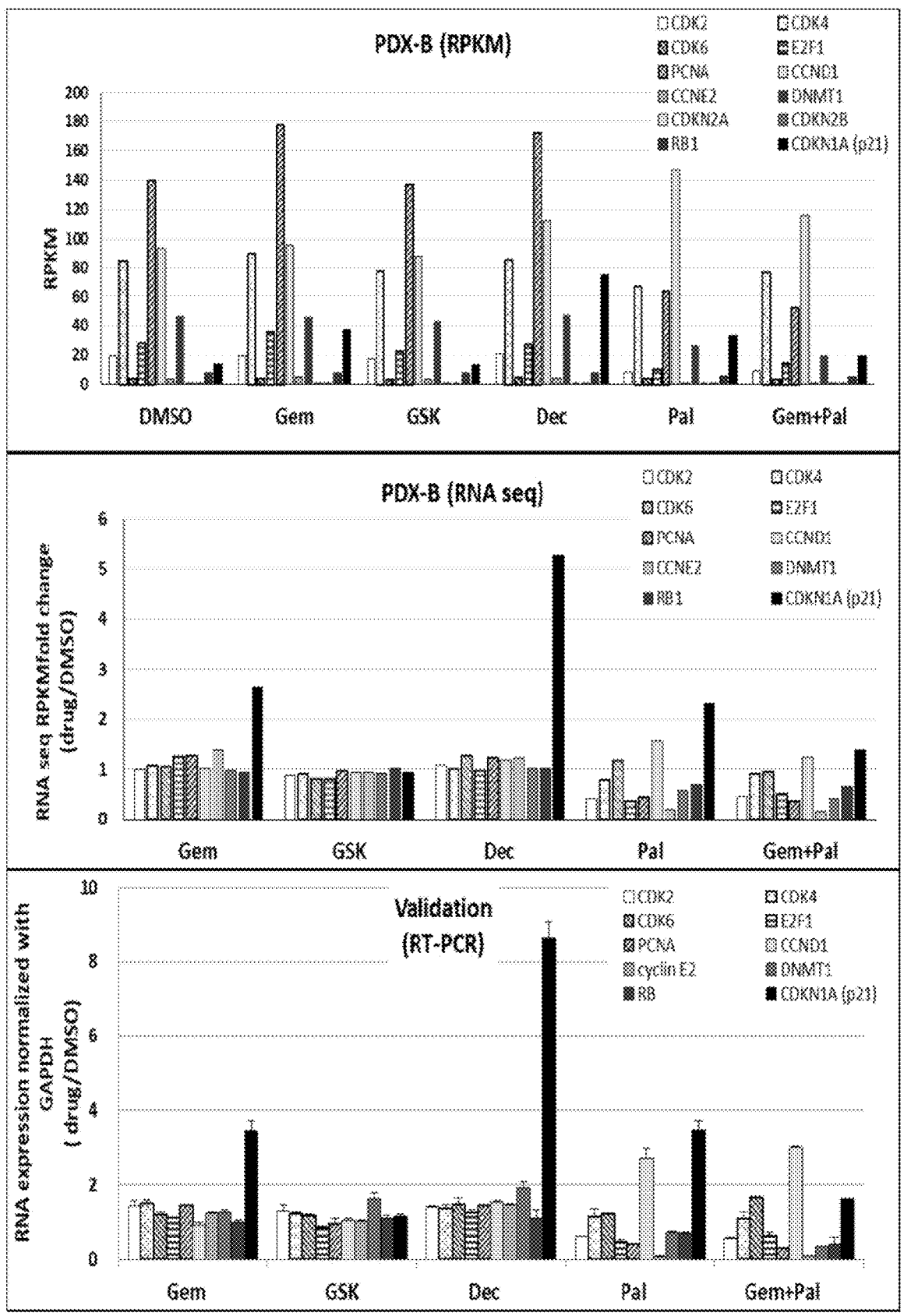
FIGS. 9A-9C: Gene expression in NPC PDX-B with different drug treatments.
Figure 9B:
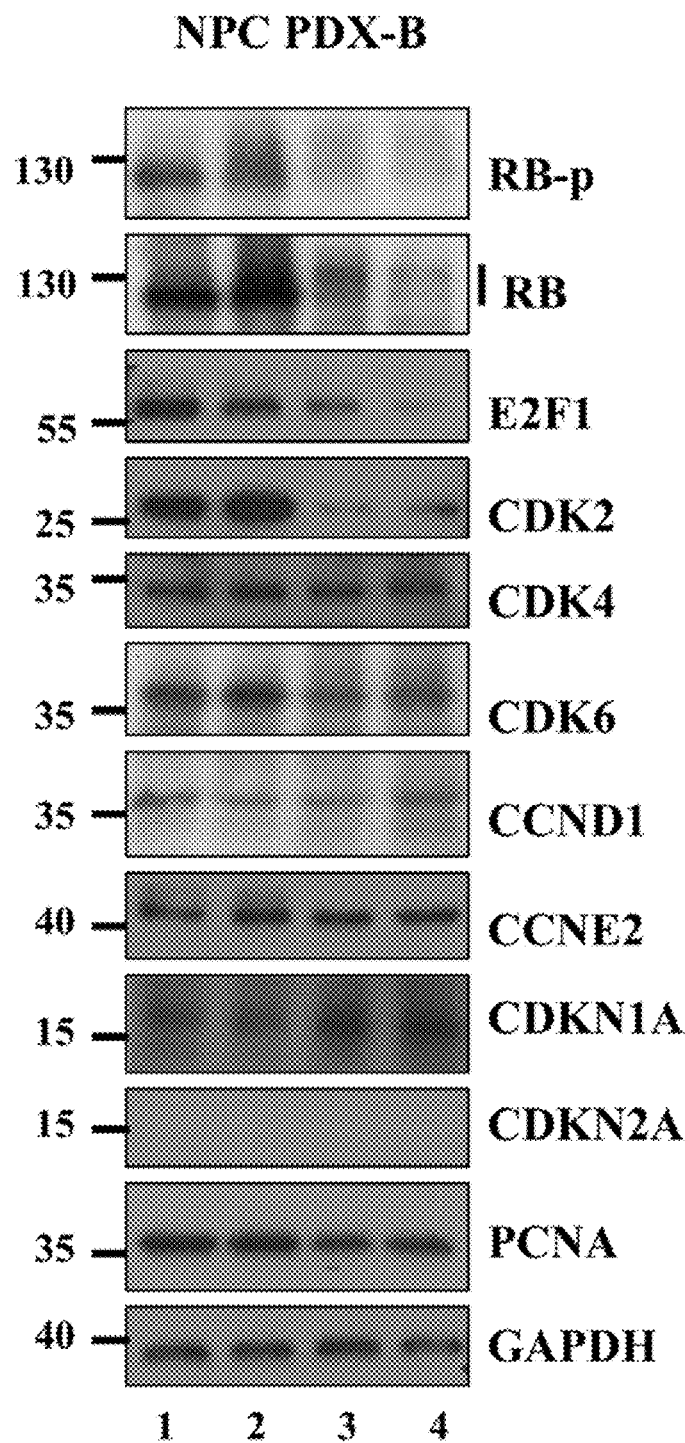
Figure 9C:
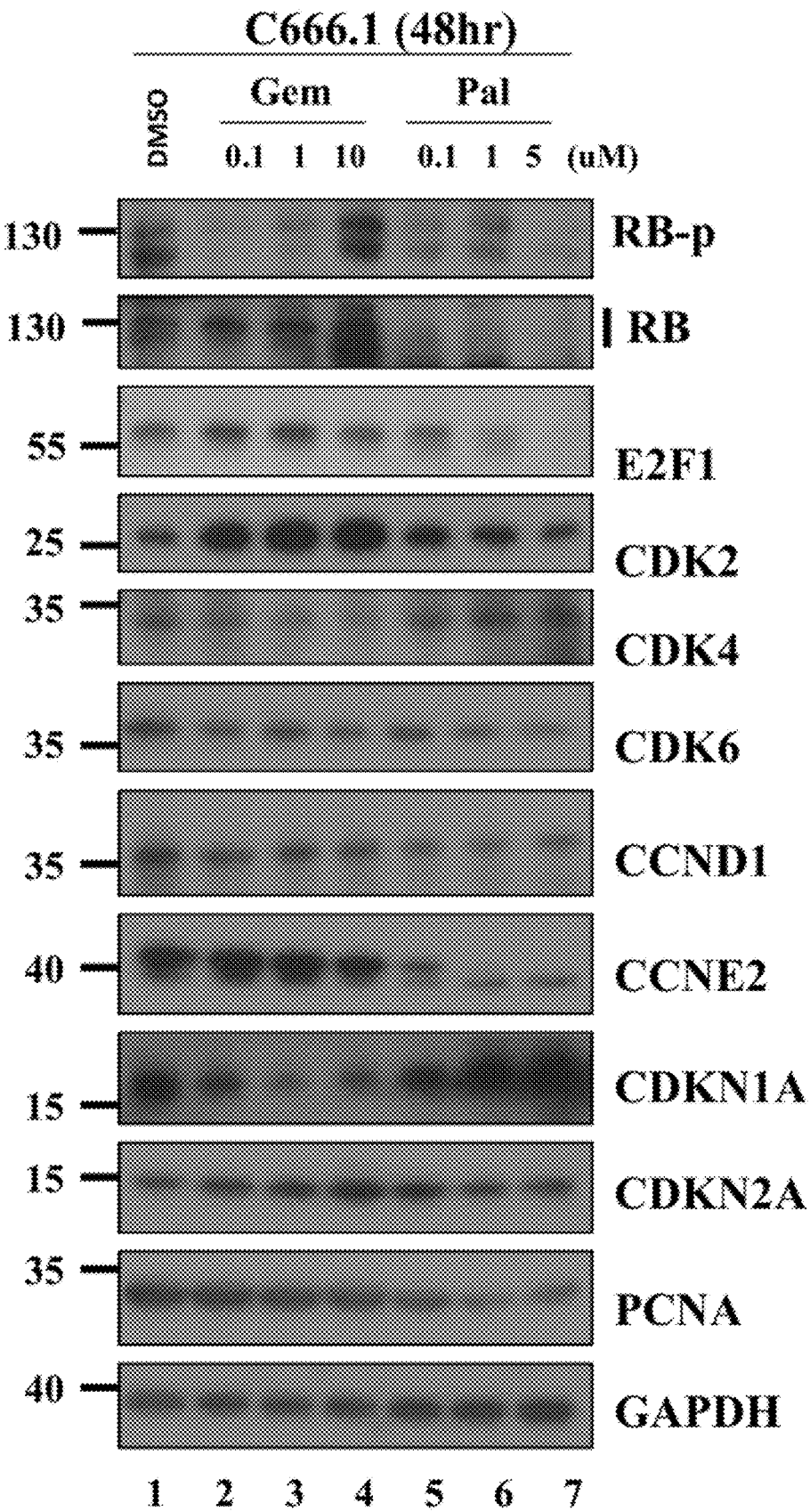

To compare the nine selected cell cycle-related genes before and after different drug treatments in PDX-Bone, normalized reads per kilobase million (RPKM; FIG. 9A, upper panel), fold change of normalized RPKM versus control (DMSO) (FIG. 9A, middle panel), and fold change of Q-RT-PCR RNA expression validation (FIG. 9A, lower panel) were determined. Since CDKN2A and 2B genes (grey bars) were deleted in NPC PDX-Bone, no RNA transcript was detected (FIG. 9A, upper panel). The gene expression fold changes following different drug treatments assayed by RNA-Seq were comparable to those assessed using Q-RT-PCR. This example observed no significant fold changes in the expression of the nine genes after GSK treatment, suggesting that the EZH2 inhibitor does not target the selected cell cycle genes. Treatment with GEM, DEC and PAL induced a 3 to 5-fold increase in expression of cell arrest marker CDKN1A (p21). In addition, after PAL or GEM+PAL treatment, both RNA-Seq and Q-RT-PCR data revealed 50% to 80% reduction in expression of the cell cycle activators CDK2, E2F1, PCNA, CCNE2, and RB1. As shown in FIG. 9B, consistent with WES and RNA expression data, this example observed no CDKN2A protein expression in the PDX-Bone tumor. Significant reduction in protein levels of cell cycle activators in PDX-Bone, including hyperphosphorylated RB (RB-p), total RB, E2F1 and CDK2, was evident after GEM and PAL treatment. CDK6 and PCNA protein levels were slightly decreased. On the other hand, protein expression of the cell arrest marker, CDKN1A (p21), was markedly increased. As shown in FIG. 9C, similar results were observed in C666-1 after 48 h treatment with the two drugs (FIG. 4C). The data of this example collectively indicate that PAL blocks CDK activities and simultaneously reduces the protein levels of several key cell cycle activators, leading to effective suppression of PDX-Bone tumor growth in vivo.

Example 6: Correlation of CNVs of CCND1 and CDKN2A with EBV DNA Load in NPC Patient Plasma Plasma EBV DNA load is used as a viral marker to monitor NPC tumor status; elevation of EBV DNA load in blood is usually associated with cancer recurrence/metastasis. It is likely that EBV DNA load is related to CNV gain of CCND1 and loss of CDKN2A. In this situation, PAL, may block the cell cycle effectively in NPC tumors with a CCND1 amplification and CDKN2A deletion genetic background. Detection of EBV DNA load and CNVs of both CCND1 and CDKN2A in liquid biopsy may have clinical value. A rapid PCR-based test was established to determine CNVs of the two cell cycle regulators in cell-free DNA. Prior to examination of plasma of NPC patients, this example used genomic DNA isolated from the five PDX tumors and matched patients' PBMC for Q-PCR amplification. Data obtained on CCND1, CDKN2A and RAD52 (control) correlated well with CNV results determined using WES. The correlation between the two methods was high at 0.89-0.95 (As shown in following Table 2), suggesting that the Q-PCR assay can be effectively employed to establish the copy numbers of cellular genes.

TABLE 2

Correlation between CNV detected by WES and Q-PCR

| | WES/CNV | | | | Q-PCR/CNV | | |
|---|---|---|---|---|---|---|---|
| | CCND1 | CDKN2A | RAD52 | | CCND1 | CDKN2A | RAD52 |
| PDX-ST | 1.99 | 0.00 | 4.55 | | 2.27 | 0.00 | 3.75 |
| WBC-ST | 1.97 | 2.06 | 2.11 | | 1.94 | 2.12 | 2.15 |
| PDX-LN | 9.63 | 1.35 | 2.97 | | 7.23 | 1.48 | 2.87 |
| WBC-LN | 2.04 | 2.03 | 1.99 | | 2.07 | 2.73 | 2.40 |
| PDX-LG | 4.82 | 0.00 | 3.08 | | 3.13 | 0.00 | 2.57 |
| WBC-LG | 2.02 | 1.88 | 2.04 | | 1.53 | 1.99 | 2.21 |
| PDX-LV | 2.25 | 2.36 | 3.05 | | 2.37 | 1.60 | 2.59 |
| WBC-LV | 1.97 | 2.03 | 1.86 | | 1.44 | 1.78 | 1.68 |
| PDX-B | 6.00 | 0.00 | 2.00 | | 3.13 | 0.00 | 1.22 |
| WBC-B | 2.00 | 2.00 | 2.00 | | 1.55 | 1.71 | 1.77 |
| | | | | Correlation coefficients (r) | 0.95 | 0.93 | 0.89 |

Figure 10A:
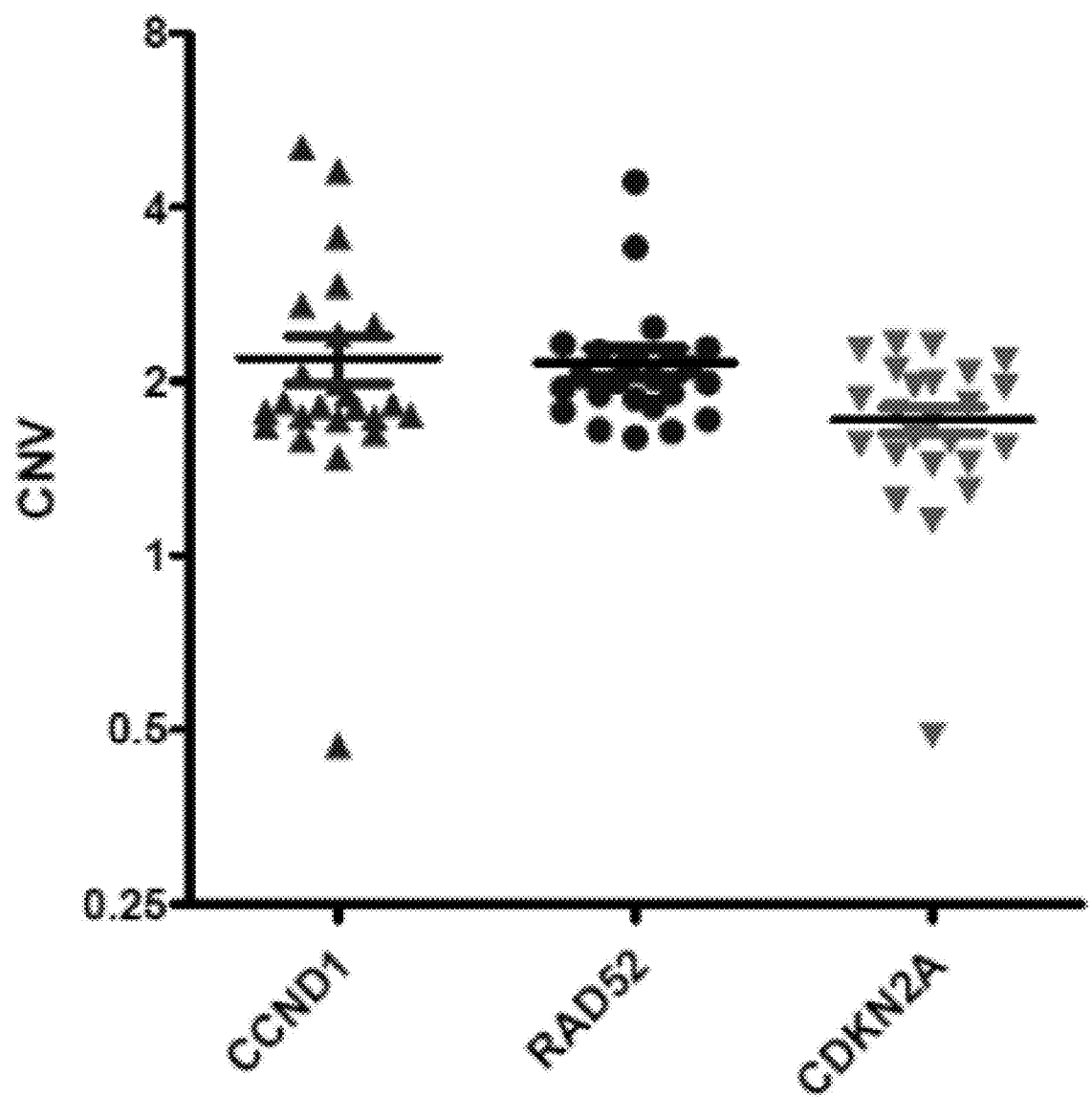
FIGS. 10A-10D: Correlation between CNV of cellular genes and low EBV copy number in NPC plasma.
Figure 10B:
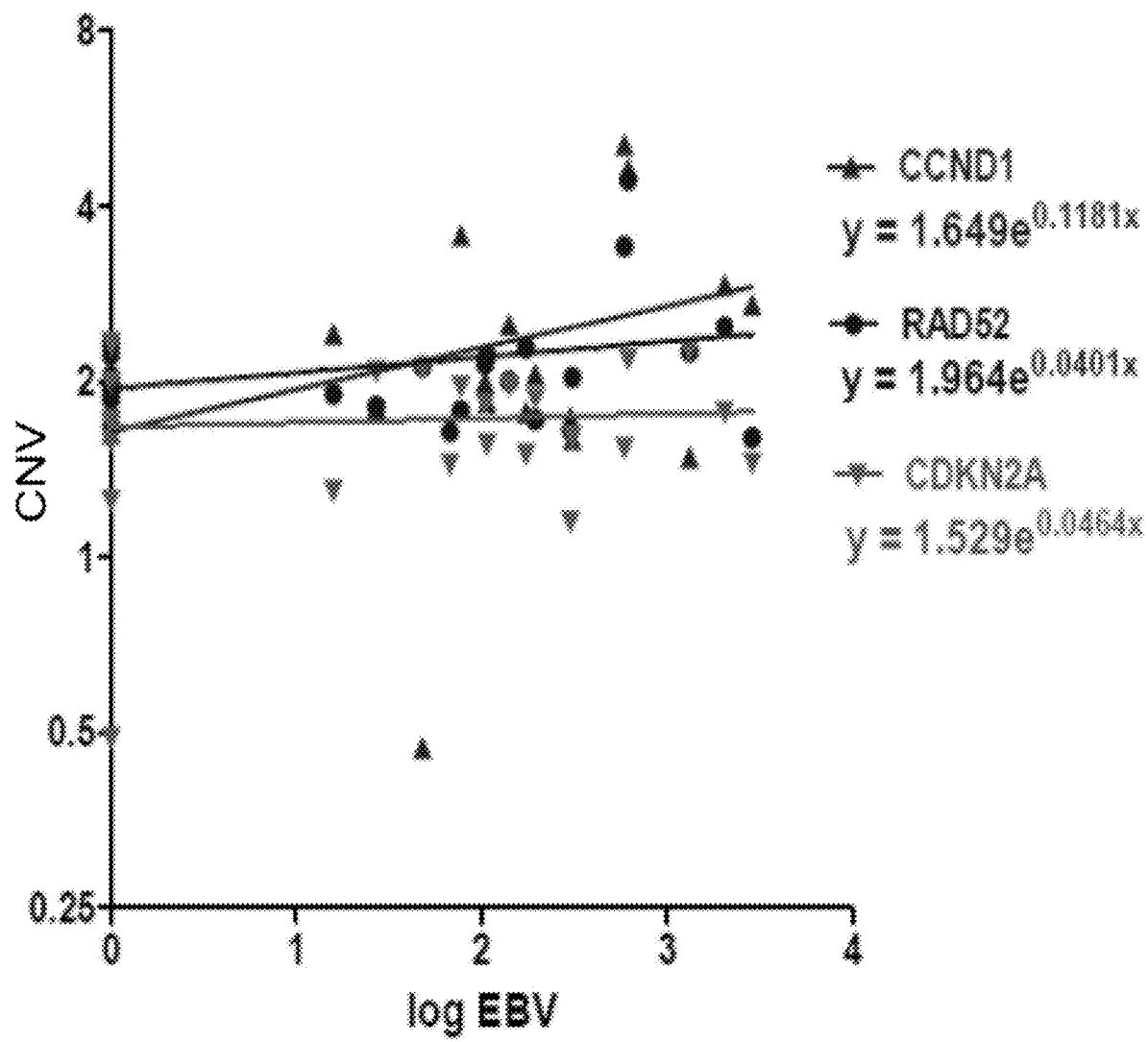
Figure 10C:
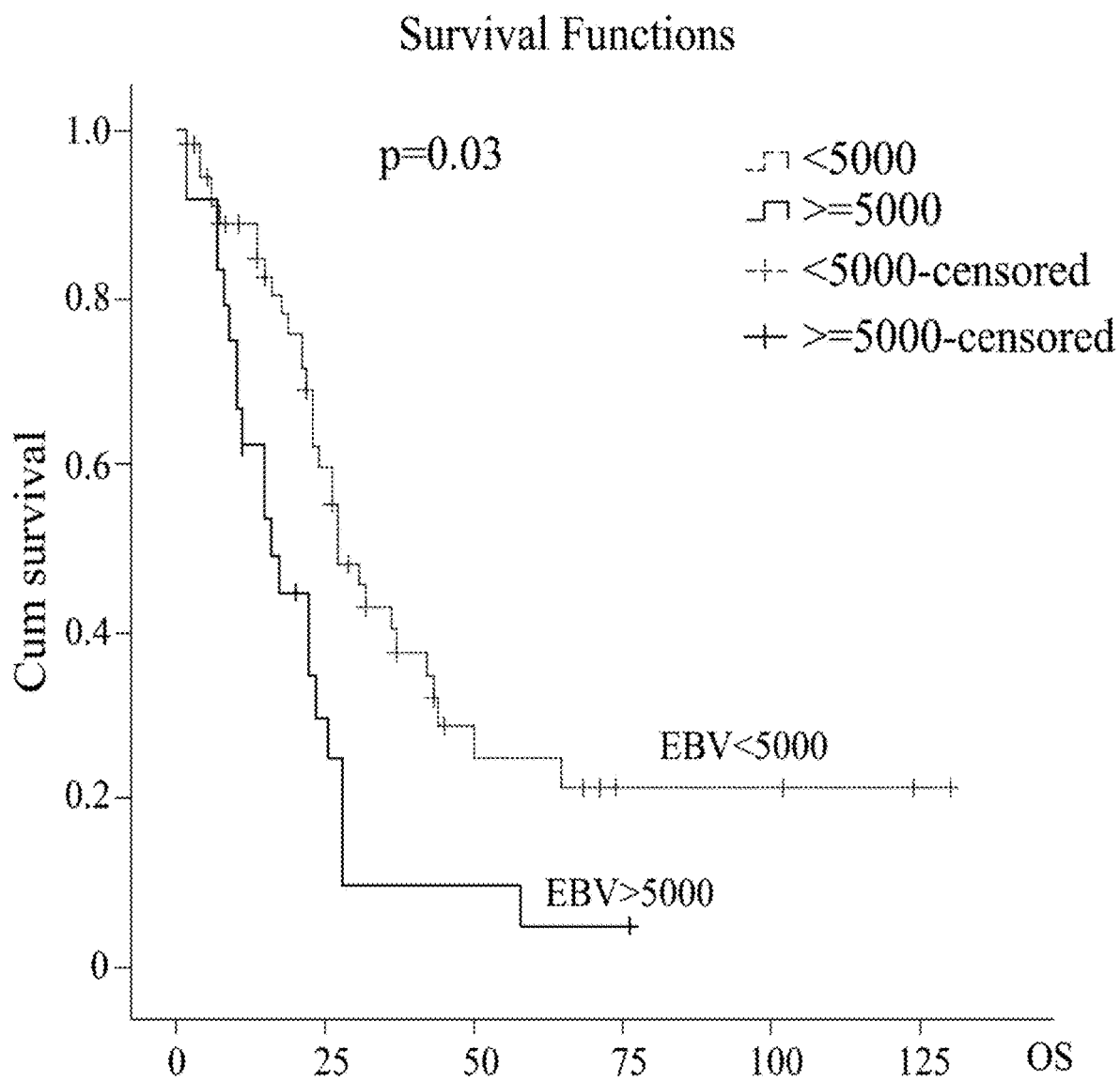
Figure 10D:
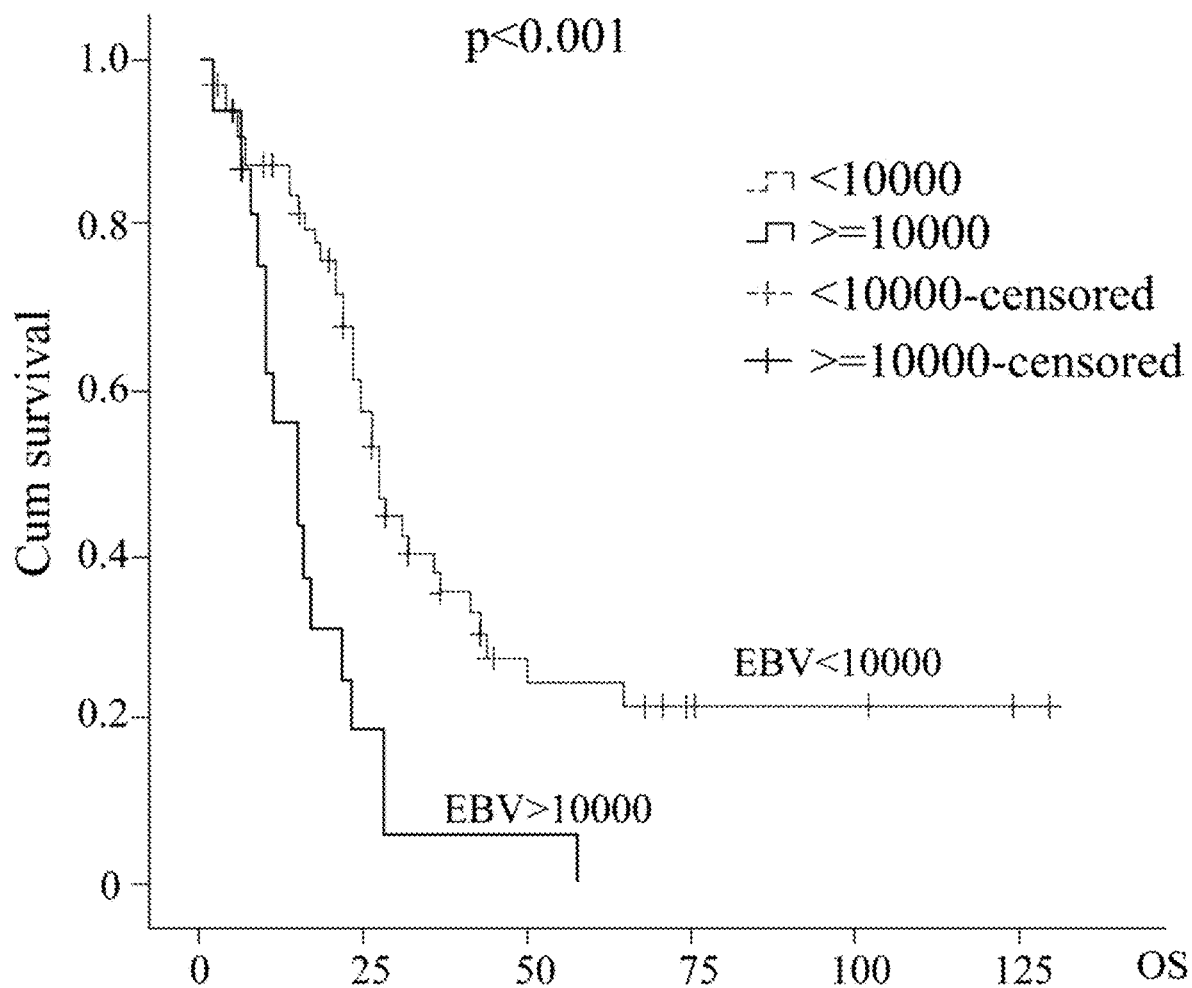
Figure 11A:
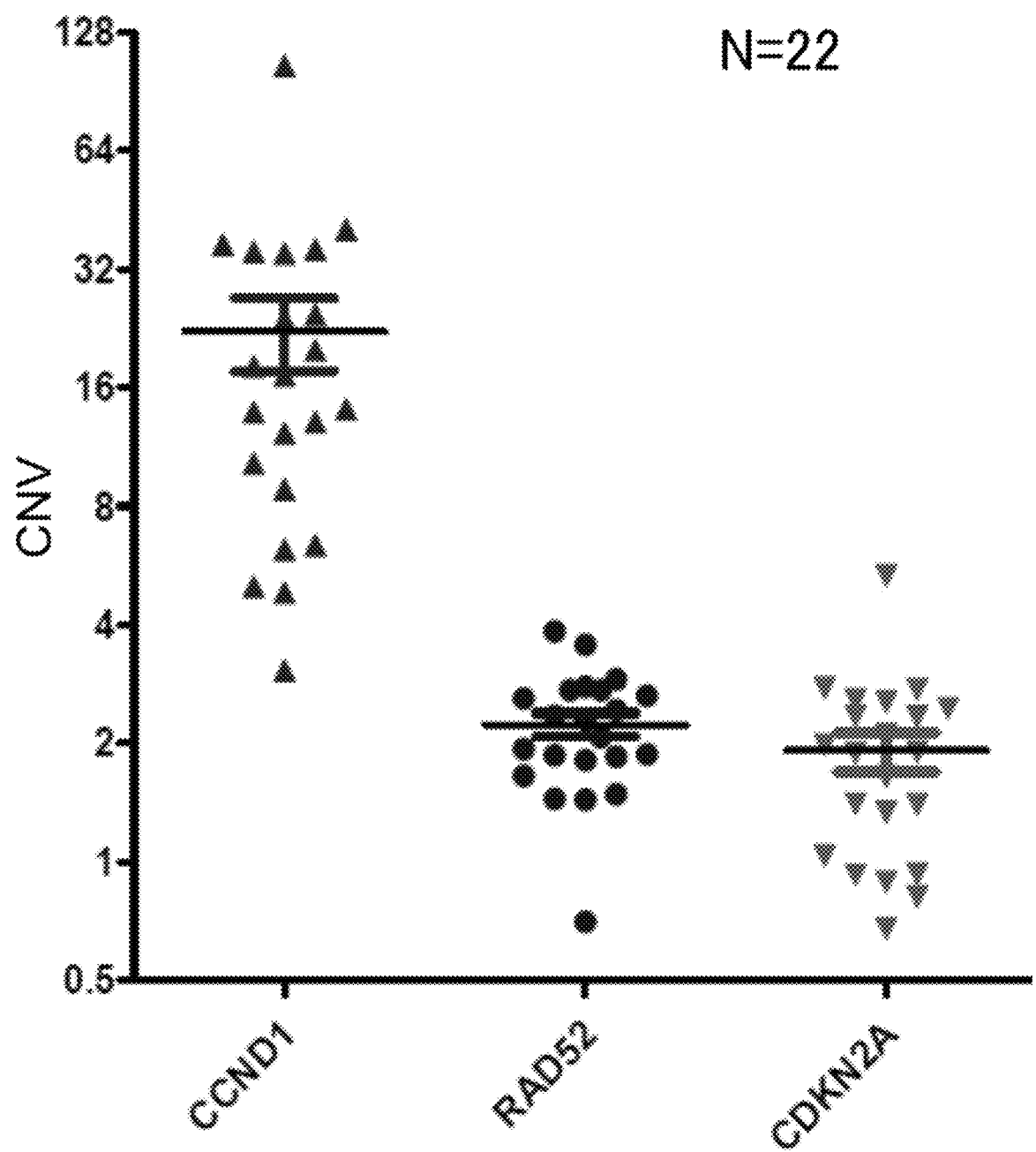
FIGS. 11A-11C: Correlation of CNV of CCND1, CDKN2A and RAD52 with high EBV copy number in 22 NPC plasma.
Figure 11B:
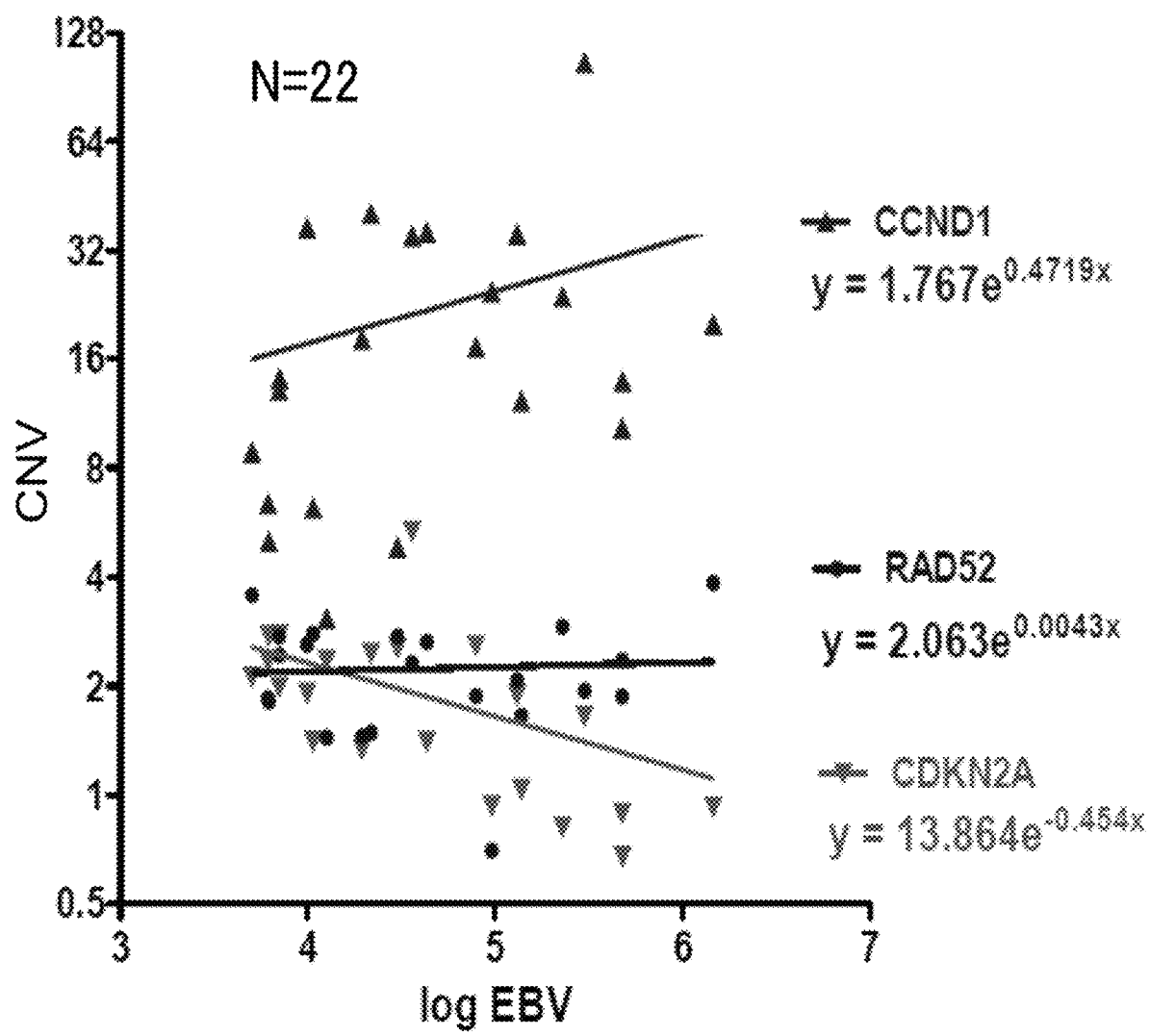
Figure 11C:
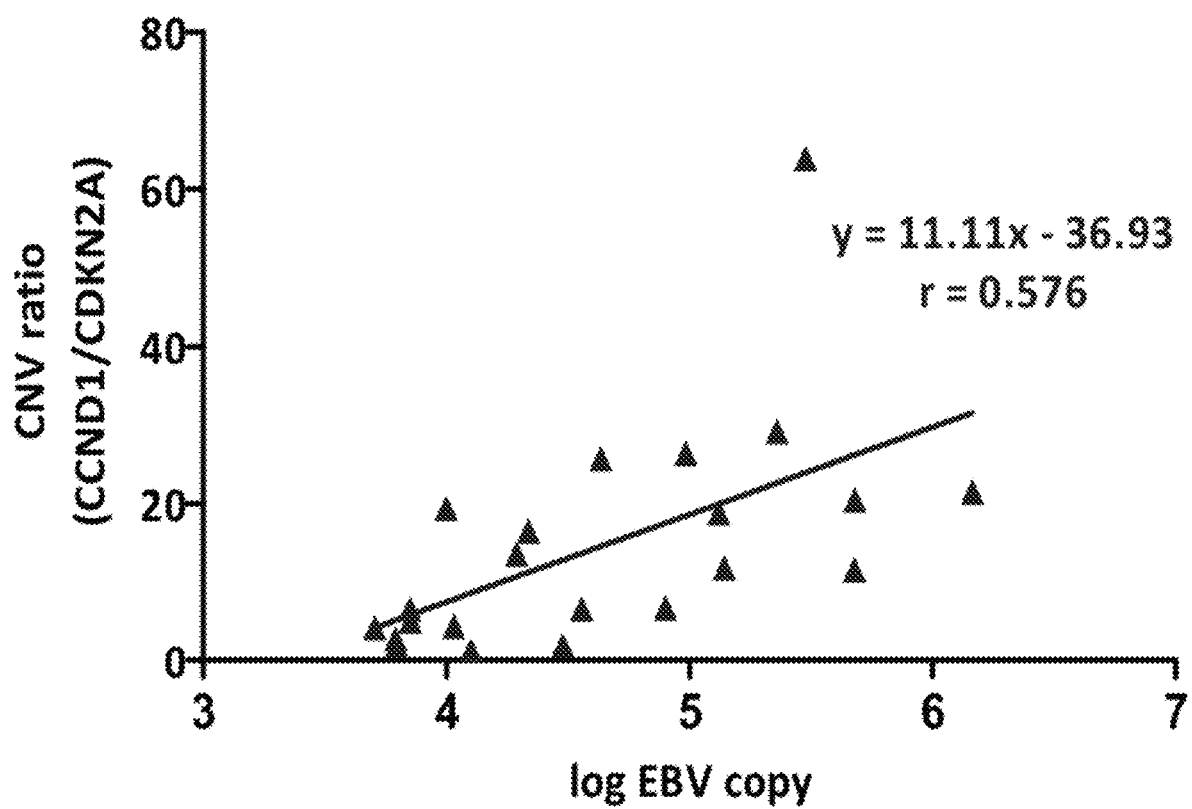

Subsequently, this example selected 22 plasma with high EBV DNA copy number (>5,000 copies/ml) collected at two different time-points from a group of 11 NPC patients and 24 plasma with low EBV DNA copy number (<5,000 copies/ml) collected from 24 NPC patients. Cell-free DNA isolated from plasma was used for Q-PCR analysis of CCND1, CDKN2A and RAD52. PCR results were normalized with those of healthy individual PBMC samples. For low EBV DNA load plasma (0-3,000 copies/ml), weak positive correlation (r=0.396) was observed between EBV DNA load and CNV of CCND1 but no correlation between EBV DNA load and CNV of (a) CDKN2A (r=0.082) and (b) RAD52 (r=0.25) (FIGS. 10A-10D). The average CNV of the three selected cellular genes was about 2 (FIG. 10A), indicating that when EBV DNA load was low in plasma (<5000 copies/ml), CNV for CDKN2A and RAD52 remained unchanged (about 2) but CNV for CCND1 began to increase (>2) even in low EBV copies. For high EBV DNA load plasma (>5,000 copies/ml), average CNV for RAD52 remained about 2, suggesting no correlation between EBV DNA load and CNV RAD52 (r=0.056) (As shown in following Table 3A-3B). However, this example observed CNV gain for CCND1 and slight CNV loss for CDKN2A in plasma with high EBV DNA load (FIG. 11A). Surprisingly, the average CCND1 CNV in the high EBV DNA load group was about 22. The correlation coefficients between EBV DNA load/ml (log) and CNVs of (a) CCND1 and (b) CDKN2A were r=0.325 (weak) and r=−0.488 (moderate) (As shown in following Table 3A-3B), respectively. At plasma EBV DNA loads >100,000 copies/ml, the chance for the cell-free DNA to lose one copy of CDKN2A was 70% (5 out of 7, Table 3A-3B). Interestingly, this example observed a better positive moderate correlation (r=0.576) with EBV DNA load in plasma using the CNV ratio of CCND1 and CDKN2A within the same sample instead of CNV of a single gene (FIG. 11B and Table 3A-3B). This new correlation plot showed that the risk of aberrant CNV of cell cycle regulators, CCND1 and CDKN2A, in NPC tumors depends on the increased EBV DNA load in the circulation. According to the linear regression equation, y=11.11x−36.93 (where x and y represent the log of EBV DNA load and CNV ratio of [CCND1/CDKN2A], respectively; FIG. 11B), in cases where EBV DNA load in plasma is 5,000 copies/ml, the CNV ratio is about 4, supporting amplification of CCND1 and/or deletion of CDKN2A. Thus, high EBV DNA load in the plasma is simultaneously associated with CNV gain in CCND1 (a cell cycle accelerator), loss in CDKN2A (a cell cycle brake), and uncontrollable cell growth in EBV-positive NPC tumors.

TABLE 3A

CNV of CCND1, p16 and RAD52 in the 11 NPC patients' plasma with high EBV copy number. (>5000/ml)

| NPC | Plasma | EBV (copy no./ml) | log EBV (High) | CCND1 | CDKN2A | RAD2 | Ratio of CCND1/CDKN2A |
|---|---|---|---|---|---|---|---|
| 1 | p7086 | 21,764 | 4.34 | 40.4 | 2.46 | 1.48 | 16.42 |
|   | p7333 | 477,336 | 5.68 | 10.28 | 0.89 | 1.87 | 11.55 |
| 2 | p4736 | 7,112 | 3.85 | 14.1 | 2.77 | 2.43 | 5.09 |
|   | p4837 | 131,652 | 5.12 | 35.46 | 1.89 | 2.08 | 18.76 |
| 3 | p4782 | 6,208 | 3.79 | 5.01 | 2.75 | 1.81 | 1.82 |
|   | p4831 | 36,140 | 4.56 | 35.06 | 5.35 | 2.31 | 6.55 |
| 4 | p5246 | 6,180 | 3.79 | 6.37 | 2.34 | 1.85 | 2.72 |
|   | p5359 | 138,748 | 5.14 | 12.25 | 1.04 | 1.66 | 11.78 |
| 5 | p4922 | 9,960 | 4.00 | 36.95 | 1.91 | 2.6 | 19.35 |
|   | p5034 | 19,508 | 4.29 | 18.14 | 1.34 | 1.45 | 13.54 |
| 6 | p5681 | 7,072 | 3.85 | 13.11 | 1.99 | 2.74 | 6.59 |
|   | p5772 | 79,508 | 4.90 | 17.22 | 2.58 | 1.88 | 6.67 |
| 7 | p5326 | 30,132 | 4.48 | 4.83 | 2.55 | 2.74 | 1.89 |
|   | p5733 | 300,128 | 5.48 | 105.31 | 1.65 | 1.94 | 63.82 |
| 8 | p6560 | 5,068 | 3.70 | 8.84 | 2.11 | 3.57 | 4.19 |
|   | p7314 | 96,324 | 4.98 | 24.51 | 0.93 | 0.7 | 26.35 |

TABLE 3A-continued

CNV of CCND1, p16 and RAD52 in the 11 NPC patients'
plasma with high EBV copy number. (>5000/ml)

| NPC | Plasma | EBV (copy no./ml) | log EBV (High) | CCND1 | CDKN2A | RAD2 | Ratio of CCND1/CDKN2A |
|---|---|---|---|---|---|---|---|
| 9 | p6678 | 12,656 | 4.10 | 3.07 | 2.35 | 1.44 | 1.31 |
|  | p7096 | 479,596 | 5.68 | 13.88 | 0.68 | 2.35 | 20.41 |
| 10 | p4366 | 10,688 | 4.03 | 6.21 | 1.41 | 2.78 | 4.40 |
|  | p4892 | 229,800 | 5.36 | 23.87 | 0.82 | 2.91 | 29.11 |
| 11 | p4434 | 43,108 | 4.63 | 35.89 | 1.4 | 2.64 | 25.64 |
|  | p5233 | 1,458,344 | 6.16 | 19.93 | 0.93 | 3.86 | 21.43 |
|  | Correlation coefficients (r) |  |  | 0.325 | −0.488 | 0.056 | 0.576 |

TABLE 3B

CNV of CCND1, p16 and RAD52 in the 24 NPC patients'
plasma with low EBV copy number. (<5000/ml)

| Plasma | EBV (copy no./ml) | log EBV (Low) | CCND1 | CDKN2A | RAD2 | Ratio of CCND1/CDKN2A |
|---|---|---|---|---|---|---|
| p5914 | — | — | 1.63 | 0.49 | 2.32 | 3.33 |
| p6640 | 1,308 | 3.12 | 1.48 | 2.27 | 2.25 | 0.65 |
| p7917 | 584 | 2.77 | 5.08 | 1.54 | 3.41 | 3.30 |
| p3435 | 27 | 1.43 | 1.8 | 2.08 | 1.81 | 0.87 |
| p3490 | 107 | 2.03 | 1.84 | 1.56 | 2.21 | 1.18 |
| p3619 | 613 | 2.79 | 4.62 | 2.18 | 4.43 | 2.12 |
| p3715 | 141 | 2.15 | 2.5 | 1.97 | 2 | 1.27 |
| p3686 | — | — | 1.75 | 2.32 | 1.87 | 0.75 |
| p6391 | 304 | 2.48 | 1.73 | 1.15 | 1.65 | 1.50 |
| p3787 | 175 | 2.24 | 1.77 | 1.5 | 2.28 | 1.18 |
| p3962 | 16 | 1.20 | 2.41 | 1.3 | 1.9 | 1.85 |
| p4012 | 2,024 | 3.31 | 2.93 | 1.77 | 2.48 | 1.66 |
| p4594 | 2,904 | 3.46 | 2.71 | 1.45 | 1.6 | 1.87 |
| p4315 | 193 | 2.29 | 2.05 | 1.87 | 1.72 | 1.10 |
| p4608 | — | — | 1.82 | 1.71 | 1.91 | 1.06 |
| p4780 | 48 | 1.68 | 0.47 | 2.1 | 2.12 | 0.22 |
| p4826 | 1 | 0 | 1.9 | 2.33 | 2.04 | 0.82 |
| p4317 | 78 | 1.89 | 3.56 | 1.96 | 1.78 | 1.82 |
| p4550 | — | — | 1.81 | 1.99 | 1.99 | 0.91 |
| p4924 | 312 | 2.49 | 1.59 | 1.61 | 2.03 | 0.99 |
| p5249 | — | — | 1.72 | 1.58 | 1.95 | 1.09 |
| p5646 | 104 | 2.02 | 1.99 | 1.83 | 2.14 | 1.09 |
| p6780 | — | — | 1.74 | 1.25 | 2.22 | 1.39 |
| p4974 | 68 | 1.83 | 1.68 | 1.44 | 1.64 | 1.17 |
| Correlation coefficients (r) |  |  | 0.396 | 0.082 | 0.25 | 0.145 |

Example 7: Elevated CCND1 Expression as Poor Prognostic Marker and Potential Treatment of PAL in NPC Tumors Assessment of CCND1 expression in 139 NPC FFPE samples from CGMH hospital (2002 to 2016) disclosed that only 9 samples (6.5%) had undetectable CCND1 while 130 samples (93.5%) had CCND1 overexpression. Among the CCND1 overexpressed samples, 116 samples (83.4%) showed strong CCND1 staining (2+ and 3+) (As shown in the following Table 4). Both expression density and percentage positivity of CCND1 cells were inversely correlated with survival with statistical significance, as shown in FIGS. 12B and 12C. Additionally, cyclin D1 was highly overexpressed in primary site tumor (87.9%) and local recurrent (93.3%) samples. Among the 91 metastatic NPC FFPE samples, 81 had matched plasma EBV DNA data. From these 81 samples whose cyclin D1 density grade correlated with mean EBV DNA load (p=0.046, as shown in the following Table 5). In addition, EBV DNA load with cutoff value of 5,000 or 10,000 copies/ml was a prognostic factor for overall survival in 81 metastatic NPC samples (FIGS. 10C and 10D). In general, the higher the EBV load, the higher the CCND1 expression and the lower the overall survival.

TABLE 4

Immnunohistochemical (IHC) staining of cyclin D1 in 139 NPC tissues from year 2002 to 2016. Primary site: 33 samples; distant metastasis: 91 samples; and local regional recurrence: 15 samples.

| | CCND1 | Primary site (n = 33) | Distant Metastasis(n = 91) | | | | Local regional recurrence (n = 15) T/N[2] |
|---|---|---|---|---|---|---|---|
| | | | Lung | Bone | Liver | LN[1] + soft tissue | |
| Total | n = 139 | 33 | 38 | 13 | 27 | 13 | 15 |
| Negative | (−) n = 9 | 4 | 2 | 1 | 0 | 1 | 1 |
| Positive | n = 130 | 29/33 (87.9%) | 36/38 (94.7%) | 12/13 (92.3%) | 27/27 (100%) | 12/13 (92.3%) | 14/15 (93.3%) |
| | +n = 14 | 1 (3.4%) | 4 (11.1%) | 4 (33.3%) | 4 (14.8%) | 0 (0%) | 1 (7.1%) |
| | ++n = 68 | 13 (44.8%) | 20 (55.6%) | 4 (33.3%) | 15 (55.56%) | 7 (58.3%) | 9 (64.3%) |
| | +++n = 48 | 15 (51.7%) | 12 (33.3%) | 4 (33.3%) | 8 (29.6%) | 5 (41.7%) | 4 (28.6%) |

1. IHC staining: Negative: grade ≤1 and cell population <5%; Positive: grade >1 and cell population ≥5%.
2. LN[1]: lymph node; T/N[2]: primary site or local regional lymph node recurrence

TABLE 5

Clinical characteristics of metastatic NPC patients with FFPE tissue cyclin D1 immnunohistochemical staining (2002-2016)

| | Total number (%) | CCND1density, number (%) | | | P-value |
|---|---|---|---|---|---|
| | | 1 (N = 16) | 2 (N = 46) | 3 (N = 29) | |
| Sex | | | | | |
| Male | 80 (87.9) | 16 (100) | 39 (84.8) | 25 (86.2) | 0.259 |
| Female | 11 (12.1) | 0 (0) | 7 (15.2) | 4 (13.8) | |
| Age | | | | | |
| Mean | 51.1 | 50.8 | 52.8 | 48.8 | 0.343 |
| Median | 51.0 | 50 | 52.5 | 48.0 | |
| Pathology | | | | | |
| Un-differentiated | 81 (89.0) | 15 (93.8) | 42 (91.3) | 24 (82.8) | 0.412 |
| Non-keratinising | 10 (11.0) | 1 (6.2) | 4 (8.7) | 5 (17.2) | |
| Metastatic site | | | | | |
| 1 | 63 (69.2) | 12 (75.0) | 34 (73.9) | 17 (58.6) | 0.542 |
| 2 | 23 (25.3) | 3 (18.8) | 11 (23.9) | 9 (31.0) | |
| 3 | 3 (3.3) | 1 (6.3) | 0 (0) | 2 (6.9) | |
| 4 | 2 (2.2) | 0 (0) | 1 (2.2) | 1 (3.4) | |
| Solitary | | | | | |
| 1 | 35 (38.5) | 8 (50.0) | 20 (43.5) | 7 (24.1) | 0.091 |
| ≥2 | 56 (61.5) | 8 (40.0) | 26 (56.5) | 22 (75.9) | |
| Chemotherapy | | | | | |
| ¥ G + P | 43 (47.3) | 9 (56.3) | 24 (52.2) | 10 (34.5) | 0.239 |
| # P/U/L + (B/M) | 48 (52.7) | 7 (43.8) | 22 (47.8) | 19 (65.5) | |
| Overall survival | | | | | |
| Month (median) | 24.0 | 52.0 | 26.0 | 15.0 | <0.001 |
| Month (95% CI) | 19.9-28.1 | 8.6-95.4 | 21.7-30.3 | 7.5-22.5 | |
| EBV* (copies/ml) mean | 23737 | 3221 (N = 13) | 10301 (N = 43) | 57515 (N = 23) | 0.046 |

¥ G + P: gemcitabine + cisplatin.
P/U/L + (B/M): cisplatin + UFT + calcium folinate + (bleomycin or mitomycin-c).
*Among 91 metastatic NPC patients only 81 had plasma EBV DNA (copies/ml) data (patient's blood was collected after receiving metastatic site tissue proof).

Figure 12A:
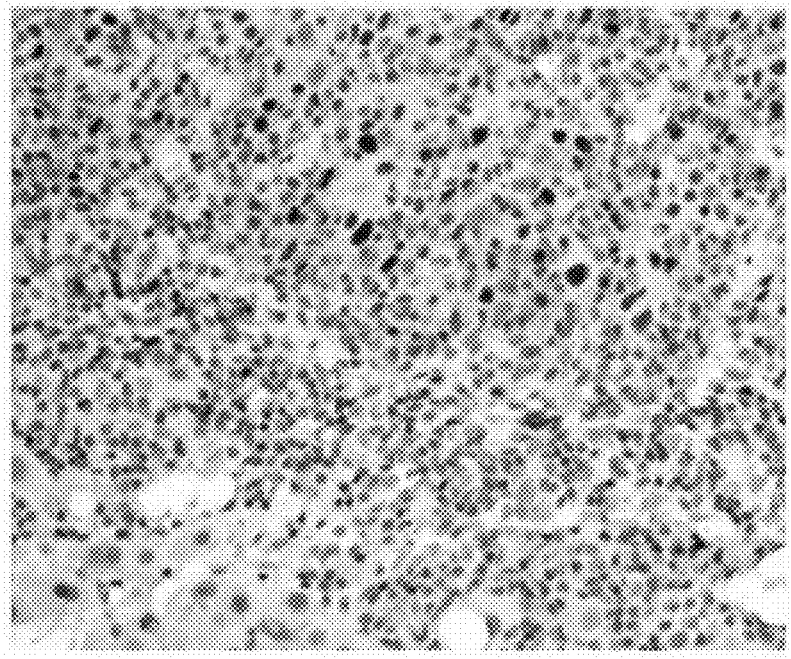
FIGS. 12A-12E: Cyclin D1 IHC in metastatic NPC clinical samples.
Figure 12A:
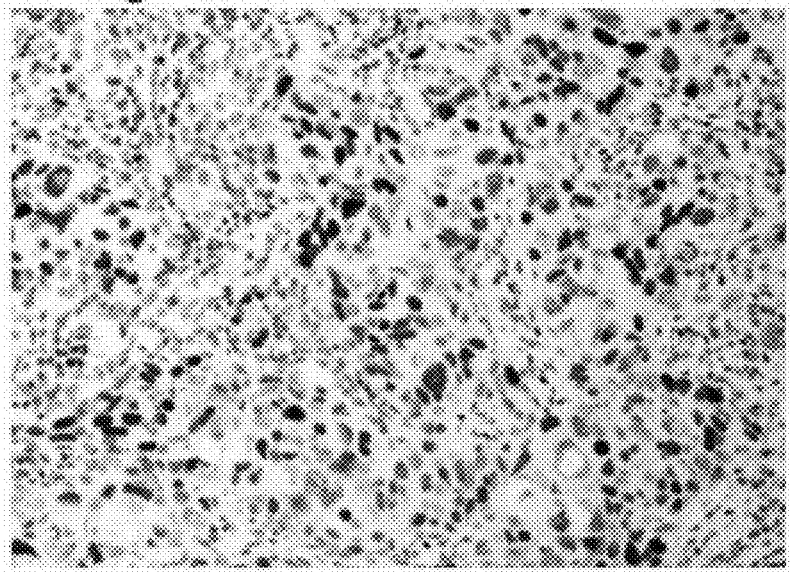
Figure 12B:
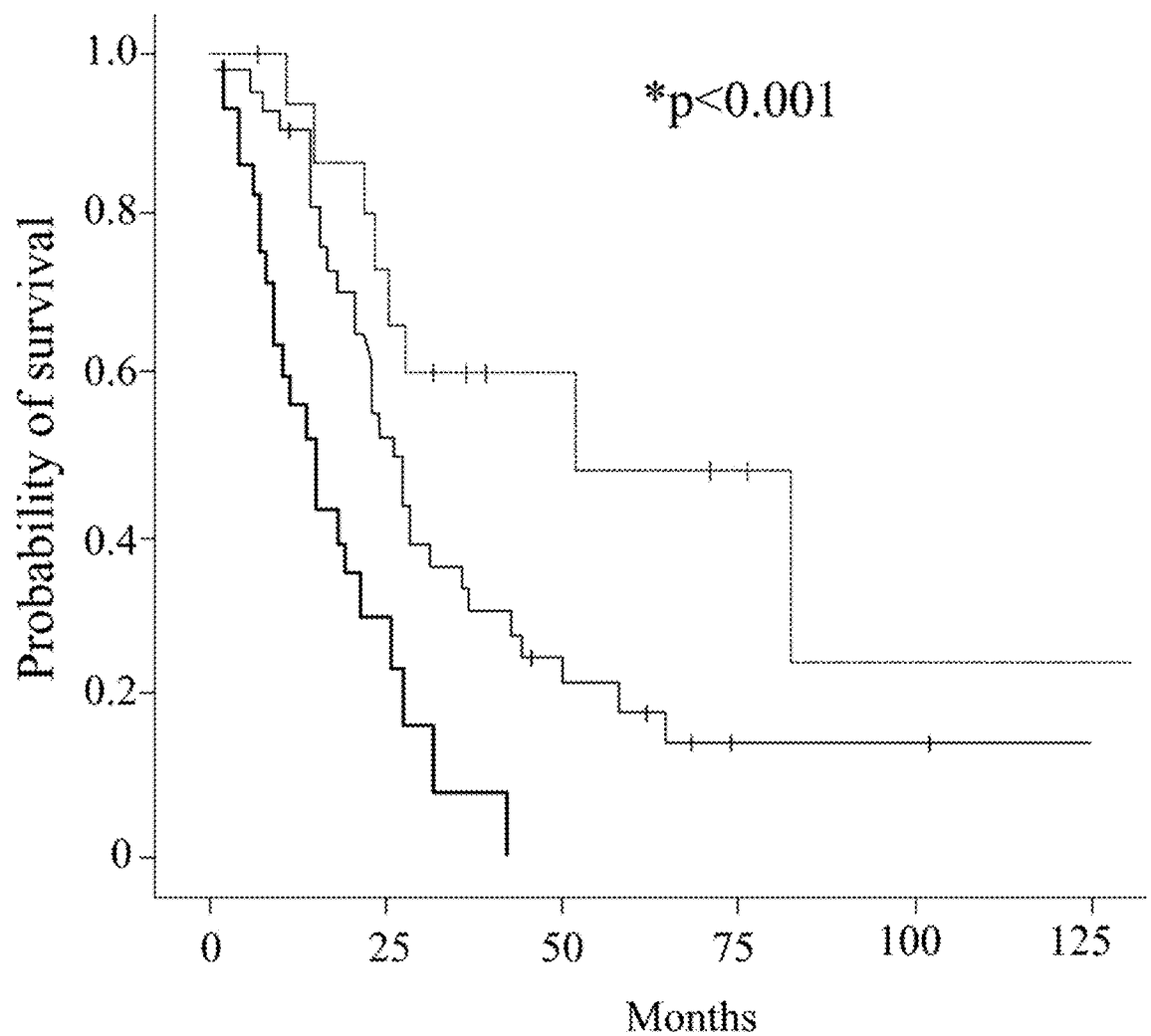
Figure 12C:
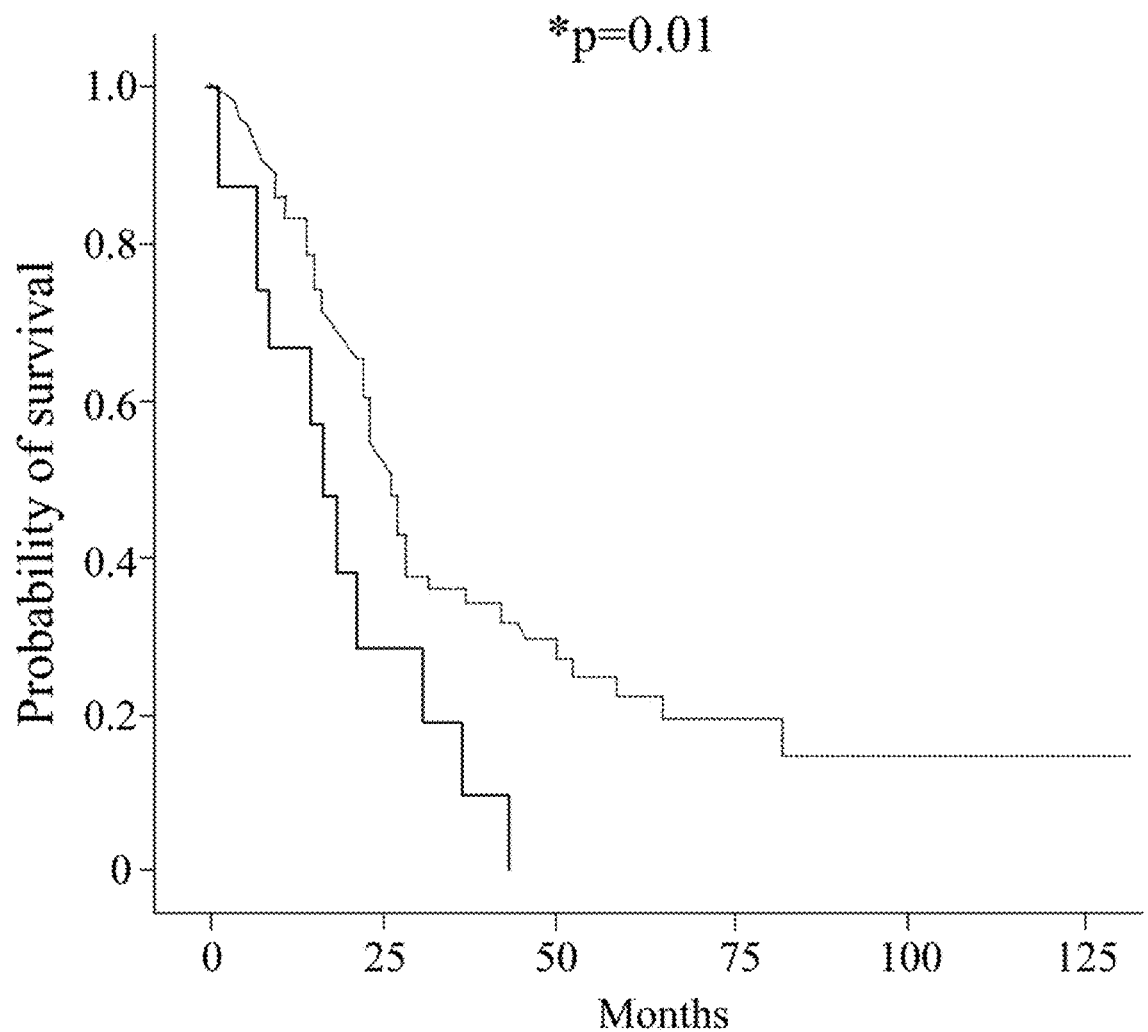
Figure 12D:
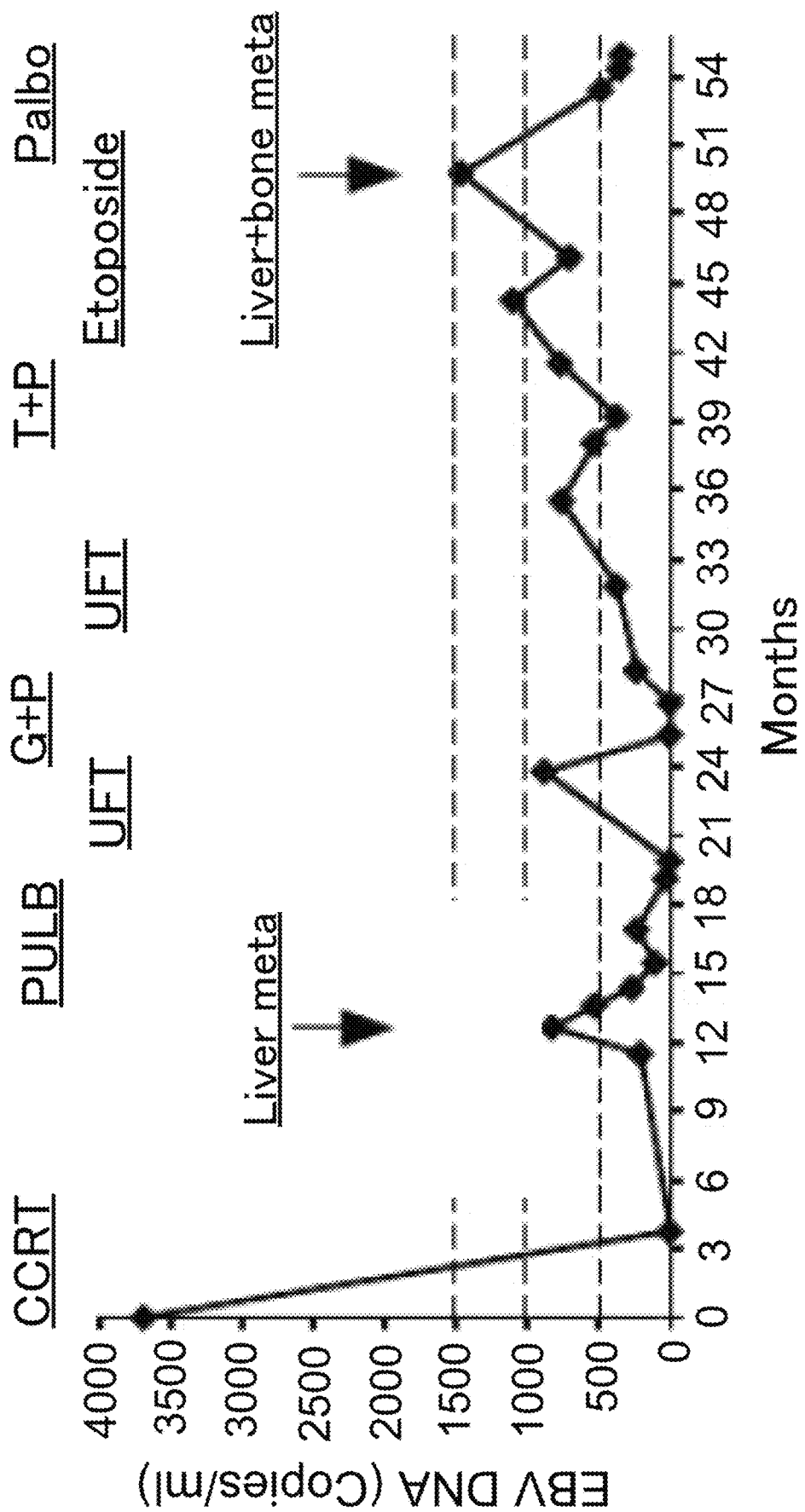
Figure 12E:
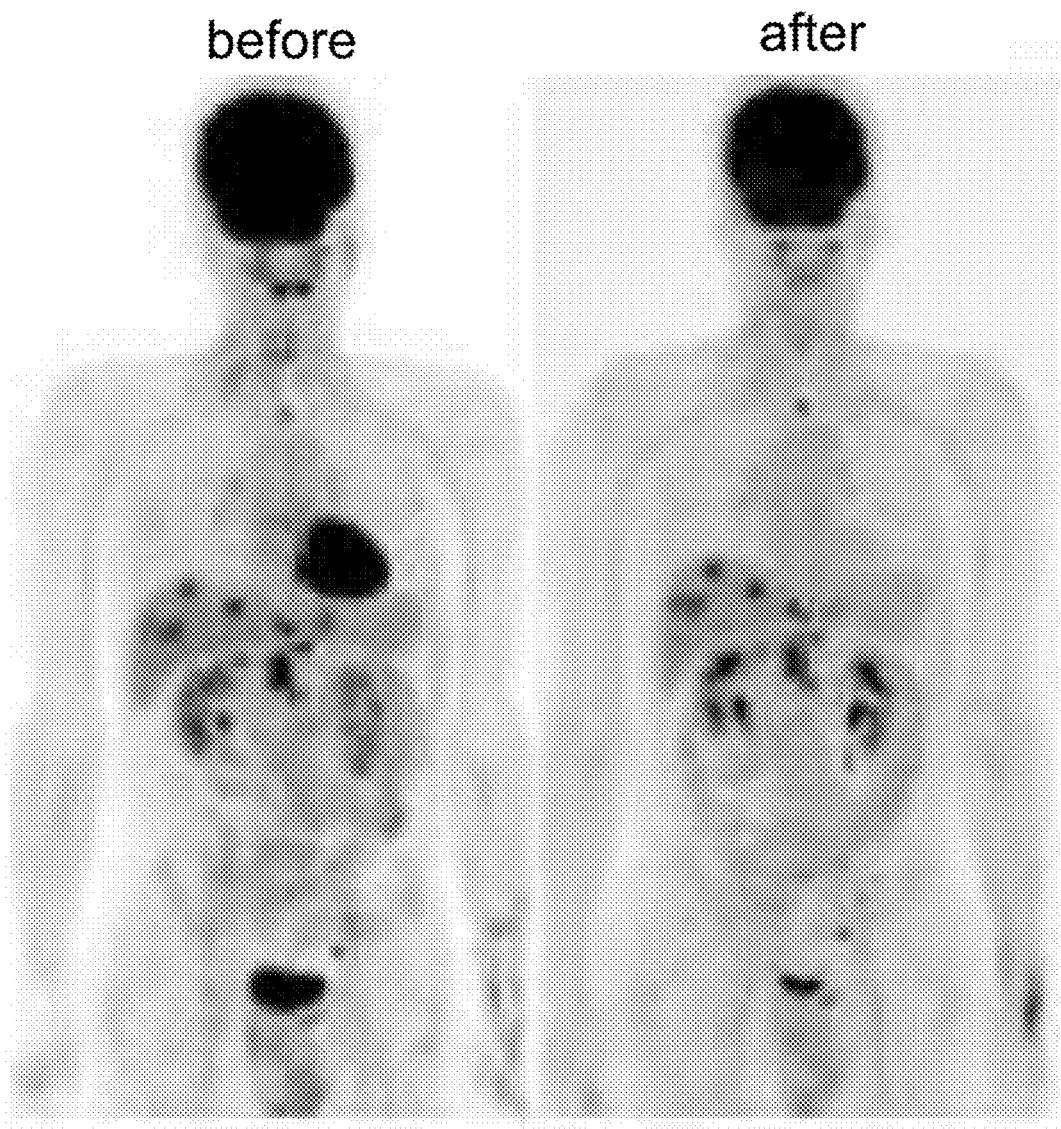

One NPC patient, subjected to local CCRT, developed liver, lung, and bone metastasis with high cyclin D1 expression (FIG. 12A). Although the patient received addition five lines of palliative chemotherapy, all of them failed to improve the condition. As the final attempt, the patient was further treated with two courses of PAL alone, and showed maximal grade 2 myelosuppression and decreased plasma EBV DNA load (FIG. 12D). A follow-up PET scan revealed stable disease (FIGS. 12D and 12E). The data of this example suggest that PAL as salvage treatment shows anti-cancer efficacy to some extent. Wherein PAL (codenamed PD-0332991, trade name: IBRANCE, purchased from Pfizer) is administered according to the following schedule. The dose range of IBRANCE is between 75 mg/day to 125 mg/day. The recommended dose of IBRANCE is 125 mg/day taken orally with food for 21 consecutive days followed by 7 days off treatment to comprise a complete cycle of 28 days.

As mentioned above, the method of this invention is for evaluating whether a patient with cancer is suitable for being administered with target drugs, a method for treating a patient and a use of a biomarker in an in vitro sample of an individual with cancer for manufacturing a diagnosis combination. This invention analysis the CNV ratio of the CCND1 gene and the CDKN2A gene from the in vitro sample. And the CNV ratio is used for accurate personal medication recommendations of CDK inhibitor drugs. Due to the cancer target drugs are very expensive, the doctors can select a suitable patient (such as high CNV ratio) by the method of this invention, and the CNV ratio could be a support for medication recommendation.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for treating nasopharyngeal cancer (NPC), comprising,
   a) obtaining a biological sample from a patient with NPC;
   b) detecting a copy number of CCND1 and CDKN2A in the biological sample;
   c) calculating a copy number variation ratio (CNV ratio) between the copy number of CCND1 and CDKN2A;
   d) measuring an amount of Epstein-Barr virus (EB virus) in the biological sample;
   e) diagnosing the patient as being suitable for treatment with palbociclib, ribociclib, or abemaciclib when the detected CNV ratio is above 4 and the amount of EB virus is above 5000 copies/ml; and
   f) administering an effective amount of palbociclib, ribociclib, or abemaciclib to the diagnosed patient.

2. A method for treating a cancer, comprising,
   a) obtaining a biological sample from a patient with cancer;
   b) detecting a copy number of CCND1 and CDKN2A in the biological sample;
   c) calculating a CNV ratio between the copy number of CCND1 and CDKN2A;
   d) diagnosing the patient as being suitable for treatment with palbociclib, ribociclib, or abemaciclib when the detected CNV ratio is above 4; and
   e) administering an effective amount of palbociclib, ribociclib, or abemaciclib to the diagnosed patient.

3. The method of claim 2, wherein the cancer is breast cancer, esophageal squamous-cell carcinoma (ESCC), hepatic carcinoma (HCC), pulmonary adenocarcinoma, melanoma, colon cancer, prostate cancer, ovary cancer, kidney cancer or leukemia.

4. The method of claim 1, wherein step f) is administering an effective amount of palbociclib to the diagnosed patient.

5. The method of claim 2, wherein step e) is administering an effective amount of palbociclib to the diagnosed patient.

* * * * *

UNITED STATES PATENT AND TRADEMARK OFFICE
CERTIFICATE OF CORRECTION

| | |
|---|---|
| PATENT NO. | : 11,761,044 B2 |
| APPLICATION NO. | : 16/451942 |
| DATED | : September 19, 2023 |
| INVENTOR(S) | : Hsin-Pai Li |

It is certified that error appears in the above-identified patent and that said Letters Patent is hereby corrected as shown below:

On the Title Page

Item [73], delete "CHANELUN INVERSITY, Taoyuan (TW)" and insert -- CHANG GUNG UNIVERSITY, Taoyuan (TW) --

Signed and Sealed this
Twenty-eighth Day of May, 2024

Katherine Kelly Vidal
*Director of the United States Patent and Trademark Office*